(12) United States Patent
Pederson et al.

(10) Patent No.: US 9,428,786 B2
(45) Date of Patent: Aug. 30, 2016

(54) BIOLOGICAL STERILIZATION INDICATOR METHOD

(71) Applicant: 3M INNOVATIVE PROPERTIES COMPANY, St. Paul, MN (US)

(72) Inventors: Jeffrey C. Pederson, Minneapolis, MN (US); Sailaja Chandrapati, Woodbury, MN (US); Bryan S. Behun, White Bear Lake, MN (US); Barry W. Robole, Woodville, WI (US); Leroy J. Longworth, Woodbury, MN (US)

(*) Notice: Subject to any disclaimer, the term of this patent is extended or adjusted under 35 U.S.C. 154(b) by 0 days.

(21) Appl. No.: 14/828,997

(22) Filed: Aug. 18, 2015

(65) Prior Publication Data

US 2015/0353984 A1 Dec. 10, 2015

Related U.S. Application Data

(63) Continuation of application No. 13/881,065, filed as application No. PCT/US2011/058259 on Oct. 28, 2011, now Pat. No. 9,145,573.

(60) Provisional application No. 61/408,997, filed on Nov. 1, 2010.

(51) Int. Cl.
*G01N 33/00* (2006.01)
*C12Q 1/02* (2006.01)
(Continued)

(52) U.S. Cl.
CPC ............... *C12Q 1/025* (2013.01); *A61L 2/28* (2013.01); *C12Q 1/22* (2013.01)

(58) Field of Classification Search
CPC ............ C12Q 1/025; C12Q 1/22; A61L 1/22
See application file for complete search history.

(56) References Cited

U.S. PATENT DOCUMENTS 5,073,488 A 12/1991 Matner
5,223,401 A 6/1993 Foltz
(Continued)

FOREIGN PATENT DOCUMENTS

WO WO 2004/000569 12/2003
WO WO 2007/070310 6/2007
(Continued)

OTHER PUBLICATIONS

3M™ Attest™ 1292S Biological Indicator for Steam 3M™ Attest™ Auto-readers; Jan. 1, 2007, pp. 1-16.
(Continued)

*Primary Examiner* — Sam P Siefke

(57) ABSTRACT

A biological sterilization indicator (BI) system and method. The system can include a BI and a reading apparatus comprising a well. The BI can include a housing, which can include a first portion, and a second portion movable between a first "unactivated" position and a second "activated" position. The BI can further include a frangible container containing a liquid and dimensioned to be positioned in the housing. The reading apparatus can be configured to detect activation of the biological sterilization indicator, for example, by detecting that the second portion is in the second position, and/or by detecting that the liquid from the frangible container is present in a specific chamber of the biological sterilization indicator. The method can include positioning the BI in the well of the reading apparatus and detecting activation, for example, by detecting one or more of the above conditions.

14 Claims, 8 Drawing Sheets

(51) Int. Cl.
*A61L 2/28* (2006.01)
*C12Q 1/22* (2006.01)

(56) References Cited

U.S. PATENT DOCUMENTS

| | | | |
|---|---|---|---|
| 5,334,841 | A | 8/1994 | Graessle |
| 5,418,167 | A | 5/1995 | Matner |
| 5,750,184 | A | 5/1998 | Imburgia |
| 5,863,790 | A | 1/1999 | Bolea |
| 5,872,004 | A | 2/1999 | Bolsen |
| 5,917,183 | A | 6/1999 | Sperling |
| 6,025,189 | A | 2/2000 | Bolea |
| 6,063,591 | A | 5/2000 | Bolea |
| 6,352,837 | B1 | 3/2002 | Witcher |
| 2003/0133830 | A1 | 7/2003 | Gonzalez |
| 2003/0235677 | A1 | 12/2003 | Hanschen |
| 2004/0197848 | A1 | 10/2004 | Behun |
| 2006/0263258 | A1 | 11/2006 | Harris |
| 2008/0261296 | A1 | 10/2008 | Justi |
| 2009/0141278 | A1 | 6/2009 | Tenney |

FOREIGN PATENT DOCUMENTS

| | | |
|---|---|---|
| WO | WO 2010/045138 | 4/2010 |
| WO | WO 2011/011189 | 1/2011 |
| WO | WO 2012/061212 | 5/2012 |
| WO | WO 2012/061213 | 5/2012 |
| WO | WO 2012/061226 | 5/2012 |
| WO | WO 2012/061227 | 5/2012 |
| WO | WO 2012/061229 | 5/2012 |

OTHER PUBLICATIONS

SGM Biotech®—Smart-Well™ Incubator for Smart-Read EZTest® Steam Self-Contained Biological Indicators; Model 1701, Dec. 1, 2010; 1 page.
SGM Biotech®—Smart-Read EZTest Biological Indicator Monitoring System, [retrieved from the internet on Jan. 27, 2012], <http://www.sgmbiotech.com/products/smart-read>.php, 3 pages.
VERIFY™ Wall Chart—Proper Procedure for Processing Verify Biological Indicators, STERIS® Corporation; (Jun. 2, 1999).
STERIS®, Technical Tip #5501, Color Reversion of Verify™ Self-Contained Biological Indicators; (Nov. 1999), 2 pages.
STERIS®, VERIFY® S3060/S3061 Self-Contained Biological Indicator for Steam and Ethylene Oxide; Technical Data, (Apr. 1, 2009) pp. 1-4.
M. Roth, Methods of Biochemical Analysis, vol. 17, D. Block, Ed., Interscience Publishers, New York, 1969, p. 89.
S. Udenfriend, Fluorescence Assay in Biology and Medicine, Academic Press, New York, 1962, p. 312.
D.J.R. Lawrence, Florescence Techniques for the Enzymologist, Methods in Enzymology, vol. 4, S. P. Colowick and N. O. Kaplan, Eds., Academic Press, New York, 1957, p. 174.
International Search Report PCT/US2011/058259 Sep. 3, 2012; 4 pgs.

BIOLOGICAL STERILIZATION INDICATOR METHOD

FIELD

The present disclosure generally relates to sterilization indicator systems and methods, and particularly, to biological sterilization indicator systems and methods.

BACKGROUND

In a variety of industries, such as the health care industry but also in other industrial applications, it can be necessary to monitor the effectiveness of processes used to sterilize equipment such as medical devices, instruments and other disposable and non-disposable articles. In these settings, sterilization is generally defined as the process of completely destroying all viable sources of biological activity, such as microorganisms, including structures such as viruses and spores. As a standard practice, hospitals include a sterility indicator with a batch of articles to assay the lethality of the sterilization process. Both biological and chemical sterility indicators have been used.

One standard type of biological sterility indicator includes a known quantity of test microorganisms, for example *Geobacillus stearothermophilus* (formerly *Bacillus stearothermophilus*) or *Bacillus atrophaeus* (formerly *Bacillus subtilis*) spores, which can be many times more resistant to particular sterilization processes than other contaminating organisms. After the indicator is exposed to the sterilization process, the sources of biological activity (e.g., spores) can be incubated in a nutrient medium to determine whether any of the sources survived the sterilization process, with source metabolism and/or growth indicating that the sterilization process was insufficient to destroy all of the sources of biological activity.

Available chemical sterility indicators can be read immediately at the end of the sterilization process. However, the results indicate only that a particular condition was present during the sterilization process, such as the presence of a particular chemical or a temperature, and potentially, that the condition was reached for a certain period of time. On the contrary, the response of sources of biological activity to all conditions actually present can be a more direct and reliable test for how effective a sterilization process is in achieving sterilization.

SUMMARY

Some aspects of the present disclosure provide a biological sterilization indicator system. The system can include a biological sterilization indicator and a reading apparatus. The biological sterilization indicator can include a housing including a first portion, and a second portion adapted to be coupled to the first portion, the second portion being movable with respect to the first portion, when coupled to the first portion, between a first position and a second position. The biological sterilization indicator can further include a container containing a liquid and being dimensioned to be positioned in the housing. At least a portion of the container can be frangible, and the container can have a first state in which the container is intact when the second portion of the housing is in the first position, and a second state in which the container is fractured when the second portion of the housing is in the second position. The biological sterilization indicator can further include a first chamber within the housing in which the container is positioned when the container is in the first state, and a second chamber within the housing in which the container and the liquid are not positioned when the container is in the first state, and into which the liquid moves when the container is in the second state. The second chamber can include at least one source of biological activity that is not in fluid communication with the liquid when the container is in the first state and that is in fluid communication with the liquid when the container is in the second state. The reading apparatus can include a well. The well can be dimensioned to receive at least a portion of the biological sterilization indicator. The reading apparatus can be configured to detect at least one of the following conditions: (i) when the biological sterilization indicator is positioned in the well with the second portion of the housing in the second position, and (ii) when the biological sterilization indicator is positioned in the well with the liquid being present in the second chamber.

Some aspects of the present disclosure provide a method for detecting an activation status of a biological sterilization indicator. The method can include providing a biological sterilization indicator and a reading apparatus. The biological sterilization indicator can include a housing including a first portion, and a second portion adapted to be coupled to the first portion, the second portion being movable with respect to the first portion between a first position and a second position. The biological sterilization indicator can further include a container containing a liquid and being dimensioned to be positioned in the housing. At least a portion of the container can be frangible, and the container can have a first state in which the container is intact when the second portion of the housing is in the first position, and a second state in which the container is fractured when the second portion of the housing is in the second position. The biological sterilization indicator can further include a first chamber within the housing in which the container is positioned when the container is in the first state, and a second chamber within the housing in which the container and the liquid are not positioned when the container is in the first state, and into which the liquid moves when the container is in the second state. The second chamber can include at least one source of biological activity that is not in fluid communication with the liquid when the container is in the first state and that is in fluid communication with the liquid when the container is in the second state. The reading apparatus can include a well dimensioned to receive at least a portion of the biological sterilization indicator. The method can further include detecting at least one of the following conditions: (i) when the biological sterilization indicator is positioned in the well with the second portion of the housing in the second position, and (ii) when the biological sterilization indicator is positioned in the well with the liquid being present in the second chamber.

Some aspects of the present disclosure provide a biological sterilization indicator system. The system can include a biological sterilization indicator and a reading apparatus. The biological sterilization indicator can include a housing, and a container containing a liquid and being dimensioned to be positioned in the housing. At least a portion of the container can be frangible, and the container can have a first state in which the container is intact and the liquid is not in fluid communication with an interior of the housing and a second state in which the container is fractured and the liquid is in fluid communication with the interior of the housing. The biological sterilization indicator can further include a first chamber within the housing in which the container is positioned when the container is in the first state, and a second chamber within the housing in which the container and the liquid are not positioned when the container is in the first state, and into which the liquid moves when the container is in the second state. The second chamber can include at least one source of biological activity that is not in fluid communication with the liquid when the container is in the first state and that is in fluid communication with the liquid when the container is in the second state. The reading apparatus can include a well that is dimensioned to receive at least a portion of the biological sterilization indicator. The reading apparatus can be configured to detect when the biological sterilization indicator is positioned in the well and the liquid is present in the second chamber.

Some aspects of the present disclosure provide a method for detecting an activation status of a biological sterilization indicator. The method can include providing a biological sterilization indicator and a reading apparatus. The biological sterilization indicator can include a housing, and a container containing a liquid and being dimensioned to be positioned in the housing. At least a portion of the container can be frangible, and the container can have a first state in which the container is intact and the liquid is not in fluid communication with an interior of the housing and a second state in which the container is fractured and the liquid is in fluid communication with the interior of the housing. The biological sterilization indicator can further include a first chamber within the housing in which the container is positioned when the container is in the first state, and a second chamber within the housing in which the container and the liquid are not positioned when the container is in the first state, and into which the liquid moves when the container is in the second state. The second chamber can include at least one source of biological activity that is not in fluid communication with the liquid when the container is in the first state and that is in fluid communication with the liquid when the container is in the second state. The reading apparatus can include a well dimensioned to receive at least a portion of the biological sterilization indicator. The method can further include detecting when the biological sterilization indicator is positioned in the well and the liquid is present in the second chamber.

Other features and aspects of the present disclosure will become apparent by consideration of the detailed description and accompanying drawings.

DETAILED DESCRIPTION

Figure 1:
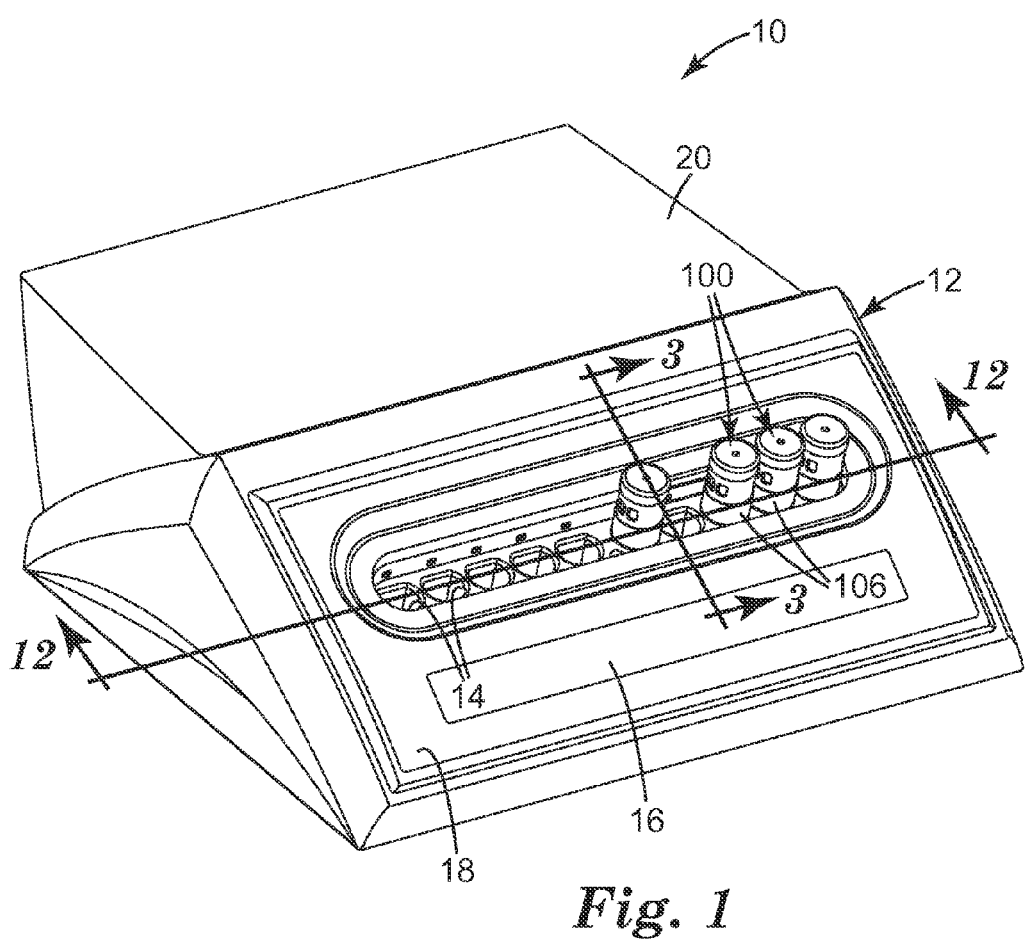
FIG. 1 is a perspective view of a biological sterilization indicator system according to one embodiment of the present disclosure, the biological sterilization indicator system comprising at least one biological sterilization indicator positioned in a reading apparatus.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports, and couplings.

Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to biological sterilization indicator systems and methods. A biological sterilization indicator is also sometimes referred to as a "biological sterility indicator," or simply, a "biological indicator." Some embodiments of the biological sterilization indicator systems and methods of the present disclosure include self-contained biological sterilization indicators that can be used to determine the lethality of a sterilizing process. A system can include the biological sterilization indicator as well as a reading apparatus or detector configured to assay the biological sterilization indicator and inform a user (e.g., visually, aurally, etc.) of the lethality of the sterilization process.

Pressurized steam or other common sterilants can be used to sterilize equipment and supplies used in healthcare environments. Small, self-contained indicators, such as biological sterilization indicators, can be used to verify the efficacy of the sterilization processes. These indicators can be biological and can contain sources of biological activity.

Nutrient medium used to nourish the sources of biological activity (e.g., spores) following a sterilization procedure can be present throughout the sterilization procedure but may not be accessible by the sources of biological activity until desired. For example, a frangible pouch or container (e.g., an ampoule, such as a glass ampoule) can house the medium 'on board' separately from the sources of biological activity, and the container can be fractured to put the sources of biological activity and medium in fluid communication with one another, when desired (e.g., after a sterilization process). Nutrients and nutrient media to facilitate the growth of microorganisms are known in the art and can be found, for example, in the "Handbook of Microbiological Media" by Ronald Atlas, published by CRC Press, Boca Raton, Fla. Matner et al. (U.S. Pat. No. 5,073,488), which is incorporated herein by reference in its entirety, describes a nutrient medium for the growth and detection of bacterial spores in a biological sterilization indicator that can be employed in biological sterilization indicators of the present disclosure.

Generally, sources of biological activity (e.g., microorganisms) are chosen to be used in a biological sterilization indicator that are resistant to a particular sterilization process. The biological sterilization indicators of the present disclosure include a viable quantity, or culture, of one or more known sources of biological activity (e.g., species of microorganism). Such sources of biological activity can be in the form of microbial spores. The test source in the biological sterilization indicator is either killed by a successful sterilization cycle, or survives if the sterilization cycle is not adequate for some reason. Bacterial spores, rather than the vegetative form of the organisms, are sometimes used at least partly because vegetative bacteria are known to be relatively easily killed by sterilizing processes. Spores can also have superior storage characteristics and can remain in their dormant state for years. As a result, in some embodiments, sterilization of an inoculum of a standardized spore strain can provide a high degree of confidence that inactivation of all microorganisms in a sterilizing chamber has occurred.

By way of example only, the present disclosure describes the one or more sources of biological activity used in the biological sterilization indicator as being "spores;" however, it should be understood that the type of source (e.g., spore) used in a particular embodiment of the biological sterilization indicator is selected for being highly resistant to the particular sterilization process contemplated. Accordingly, different embodiments of the present disclosure may use different sources of biological activity, depending on the sterilization process for which the particular embodiment is intended. The term "spores" is used throughout the present disclosure for simplicity, but it should be understood that other sources of biological activity, such as microorganisms (e.g., bacteria, fungi, viruses, etc.), spores (e.g., bacterial, fungal, etc.), enzymes, substrates for enzymatic activity, ATP, microbial metabolites, or a combination thereof, can be used in the biological sterilization indicator of the present disclosure instead.

The phrase "biological activity" generally refers to any specific catalytic process or groups of processes associated with a biological cell. Nonlimiting examples of biological activities include catabolic enzyme activities (e.g., carbohydrate fermentation pathways), anabolic enzyme activities (e.g., nucleic acid, amino acid, or protein synthesis), coupled reactions (e.g., a metabolic pathway), biomolecule-mediated redox reactions (e.g., electron transport systems), and bioluminescent reactions. "Predetermined" biological activity means that the method is directed toward the detection of a specific biological process (e.g., an enzyme reaction) or group of biological processes (e.g., a biochemical pathway). It will be appreciated by a person having ordinary skill in the art that certain predetermined biological activities may be associated with a particular type of cell (e.g., cancer cell or microorganism) or a pathological process.

Similarly, it should be understood that phrases used in the present disclosure that include the term "spore," such as "spore carrier," "spore reservoir," "spore region," "spore growth chamber," and the like, are used merely for simplicity, but that such components, elements or phrases equally apply to other sources of biological activity and are not intended to refer only to spores. For example, the above phrases can also be referred to as a "source carrier," a "source region," a "source reservoir," a "source growth chamber," and the like.

The process of bringing the spores and medium together can be referred to as "activation" of the biological sterilization indicator. That is, the term "activation" and variations thereof, when used with respect to a biological sterilization indicator, can generally refer to bringing spores of the biological sterilization indicator in fluid communication with a liquid or medium (e.g., an aqueous mixture comprising a nutrient medium for the spores). For example, when a frangible container within the biological sterilization indicator that contains the medium is at least partially fractured, punctured, pierced, crushed, cracked, or the like, such that the medium has been put in fluid communication with the spores, the biological sterilization indicator can be described as having been "activated." Said another way, a biological sterilization indicator has been activated when the spores have been exposed to the medium which was previously housed separately from the spores.

After a biological sterilization indicator has been exposed to a sterilization cycle, the sterilization load (e.g., including the items desired to be sterilized and the biological sterilization indicator) can be removed from the sterilizer. One of the first steps in processing the biological sterilization indicator can include activating the biological sterilization indicator. In some embodiments, activation can include closing the biological sterilization indicator, which can include moving a portion (e.g., a cap) of the biological sterilization indicator relative to another portion of the biological sterilization indicator (e.g., a tube, a base, a tubular body, etc.). In some embodiments, the interior of the biological sterilization indicator can remain in fluid communication with ambience during sterilization, but closed off from ambience after sterilization. For example, in some embodiments, the cap of the biological sterilization indicator can be coupled to the tube of the biological sterilization indicator during sterilization in a first position that maintains fluid communication between the interior of the biological sterilization indicator and ambience. After sterilization, the cap can be pressed further onto the tube (e.g., to a second position in which the interior of the biological sterilization indicator is no longer in fluid communication with ambience) to maintain sterility and reduce the evaporation rate of a medium (e.g., a liquid) used to support the metabolic activity and/or growth of the spores (i.e., if still viable). The medium can be contained during sterilization and released into the interior of the biological sterilization indicator after sterilization. For example, the medium can be separately housed from the spores during sterilization in a frangible container that can be at least partially fractured after sterilization (e.g., in response to moving the cap relative to the tube or base of the biological sterilization indicator) to bring the medium into fluid communication with the spores to ensure proper nutrition of the spores.

In some embodiments of the present disclosure, closing the biological sterilization indicator (e.g., moving a portion relative to another portion to seal the interior) can include or cause fracturing of a frangible container containing the medium, such that closing the biological sterilization indicator causes activation of the biological sterilization indicator.

The present disclosure generally relates further to systems and methods for confirming activation of a biological sterilization indicator. For example, in some embodiments, "activation" can be confirmed by determining that a portion of the biological sterilization indicator has been moved a sufficient amount relative to another portion of the biological sterilization indicator to cause the frangible container to fracture, and/or by determining that liquid that was previously contained (e.g., during sterilization) has moved to a region within the biological sterilization indicator where it can come into contact with any source of biological activity, for example, that may have survived the sterilization procedure. That is, some embodiments of the systems and methods of the present disclosure can be used to detect and/or confirm "cap closure." In addition, or alternatively, in some embodiments, the systems and methods of the present disclosure can be used to detect and/or confirm the presence of liquid (e.g., growth medium) in a specific chamber of the biological sterilization indicator.

In some embodiments, the systems and methods of the present disclosure can be used to detect whether the biological sterilization indicator has been activated and the medium and spores are in fluid communication with one another. For example, in some embodiments, the position of the cap of the biological sterilization indicator relative to another portion of the biological sterilization indicator can be detected to determine whether the frangible container is intact or broken, and such information can indicate whether the medium and the spores are in fluid communication with one another. As a result, some embodiments of the present disclosure can reliably assay the position of one portion of the biological sterilization indicator relative to another portion to determine whether the biological sterilization indicator has been activated. In some embodiments, alternatively or additionally, activation of the biological sterilization indicator can be confirmed by detecting the presence of liquid (e.g., a growth medium) in a spore growth chamber or detection chamber of the biological sterilization indicator.

Confirmation of the activation of the biological sterilization indicator can be important, because if the liquid or medium is not made available to the spores, the biological sterilization indicator may not function properly, which may compromise the efficacy result of a given sterilization process.

The biological sterilization indicator of the present disclosure can be used with a variety of sterilization processes including, but not limited to, exposure to steam (e.g., pressurized steam, dry heat, gaseous or liquid agents (e.g., ethylene oxide, hydrogen peroxide, peracetic acid, ozone, or combinations thereof), radiation, or combinations thereof. In at least some of the sterilization processes, an elevated temperature, for example, 50° C., 100° C., 121° C., 132° C., 134° C., or the like, is included or may be encountered in the process. In addition, elevated pressures and/or a vacuum may be encountered, for example, 15 psi ($1 \times 10^5$ Pa)

The spores used in a particular system are selected according to the sterilization process used. For example, for a steam sterilization process, *Geobacillus stearothermophilus* or *Bacillus stearothermophilus* can be used. In another example, for an ethylene oxide sterilization process, *Bacillus atrophaeus* (formerly *Bacillus subtilis*) can be used. In some embodiments, the sterilization process resistant spores can include, but are not limited to, at least one of *Geobacillus stearothermophilus, Bacillus stearothermophilus, Bacillus subtilis, Bacillus atrophaeus, Bacillus megaterium, Bacillus coagulans, Clostridium sporogenes, Bacillus pumilus*, or combinations thereof.

Enzymes and substrates that can be suitable for use in the biological sterilization indicator of the present disclosure are identified in U.S. Pat. No. 5,073,488 (Matner et al), U.S. Pat. No. 5,418,167 (Matner et al.), and U.S. Pat. No. 5,223,401 (Foltz et al.), which are incorporated herein by reference for all they disclose.

Suitable enzymes can include hydrolytic enzymes and/or enzymes derived from spore-forming microorganisms, such as *Bacillus stearothermophilus* and *Bacillus subtilis*. Enzymes from spore-forming microorganisms that can be useful in the biological sterilization indicators of the present disclosure can include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase and fatty acid esterases.

Some embodiments of the biological sterilization indicator can include chromogenic and/or fluorogenic substrates that react with enzymes to form detectable products (M. Roth, *Methods of Biochemical Analysis*, Vol. 17, D. Block, Ed., Interscience Publishers, New York, 1969, p. 89, incorporated herein by reference; S. Udenfriend, *Fluorescence Assay in Biology and Medicine*, Academic Press, New York, 1962, p. 312; and D. J. R. Lawrence, *Fluorescence Techniques for the Enzymologist*, Methods in Enzymology, Vol. 4, S. P. Colowick and N. O. Kaplan, Eds., Academic Press, New York, 1957, p. 174). These substrates may be classified in two groups based on the manner in which they create a visually detectable signal. The substrates in the first group react with enzymes to form enzyme-modified products that are themselves chromogenic or fluorescent. Substrates in the second group form enzyme-modified products that must react further with an additional compound, or compounds, to generate a color or fluorescent signal.

As a result, the phrase "detectable product" can refer to any molecule, compound, substance, substrate, or the like, or combinations thereof, that can be detected by any of the detection methods or processes described below. For example, such detectable products can be a sign of the viability of a source of biological activity, and detection of such products can generally indicate the failure or inadequacy of a sterilization process.

In some embodiments, the source of active enzyme can be (1) the purified, isolated enzyme derived from an appropriate microorganism; (2) a microorganism to which the enzyme is indigenous or added by genetic engineering; and/or (3) a microorganism to which the enzyme has been added during sporulation or growth, such that the enzyme is incorporated or associated with the microorganism, e.g., an enzyme added to a spore during sporulation which becomes incorporated within the spore. In some embodiments, the microorganisms which may be utilized as the source of an enzyme include bacteria or fungi in either the spore or vegetative state. In some embodiments, the enzyme source includes *Bacillus, Clostridium, Neurospora, Candida*, or a combination of such species of microorganisms.

The enzyme alpha-D-glucosidase has been identified in spores of *Bacillus stearothermophilus*, such as those commercially available as "ATCC 8005" and "ATCC 7953" from American Type Culture Collection, Rockville, Md. The enzyme beta-D-glucosidase has been found in *B. subtilis* (e.g., commercially available as "ATCC 9372" from American Type Culture Collection).

In the event that an isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. In such a case, the method of the present disclosure may include the step of incubating any viable microorganism remaining after the sterilization cycle with an aqueous nutrient medium to confirm the sterilization efficacy.

In general, monitoring the effectiveness of the sterilization process can include placing the biological sterilization indicator of the present disclosure in a sterilizer. In some embodiments, the sterilizer includes a sterilization chamber that can be sized to accommodate a plurality of articles to be sterilized, and can be equipped with a means of evacuating air and/or other gases from the chamber and a means for adding a sterilant to the chamber. The biological sterilization indicator of the present disclosure can be positioned in areas of the sterilizer that are most difficult to sterilize (e.g., above the drain). Alternately, the biological sterilization indicator of the present disclosure can be positioned adjacent (or in the general proximity of) an article to be sterilized when the biological sterilization indicator is positioned in the sterilization chamber. In addition, the biological sterilization indicator can be positioned in process challenge devices that can be used in sterilizers.

The sterilization process can further include exposing the article(s) to be sterilized and the biological sterilization indicator to a sterilant. In some embodiments, the sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological sterilization indicator.

In general, after the biological sterilization indicator has been exposed to a sterilization cycle, a liquid (e.g., a growth media, water that can be mixed with a solid growth media, etc., or combinations thereof) can be introduced to the spores. As mentioned above, the step in which the liquid is introduced to the spores can be referred to the "activation step." If the spores have survived the sterilization cycle, the liquid will facilitate metabolic activity and/or growth of the spores, and such activity and/or growth can be investigated. If growth is observed, the sterilization cycle is generally deemed ineffective.

FIGS. 1-4 illustrate a biological sterilization indicator system 10 according to one embodiment of the present disclosure. The biological sterilization indicator system 10 includes a reading apparatus 12 (also sometimes referred to as a "detector", a "reader," an "assaying device", or the like) and one or more biological sterilization indicators 100. Particularly, as shown in FIG. 1, the reading apparatus 12 can include one or more wells or recesses 14. Each well 14 can be dimensioned to receive at least a portion of a biological sterilization indicator 100. Each well 14 can have any desired shape, size or configuration necessary to hold and/or retain at least a portion of a biological sterilization indicator 100. In some embodiments, as shown in FIG. 1, each well 14 of the reading apparatus 12 can be dimensioned to receive one biological sterilization indicator 100, and each well 14 can be configured to assay, and output results for, one biological sterilization indicator 100 at a time. Examples of various features that may be employed in the reading apparatus 12 are described in U.S. Pat. No. 6,025,189 (Bolea et al.), which is incorporated herein by reference.

As further shown in FIG. 1, the reading apparatus 12 can further include a display and/or user interface 16, which can visually display various outputs from the reading apparatus 12 and/or which can receive input from a user (e.g., via a multi-button membrane switch). Various outputs that can be displayed can include, but are not limited to, errors or error codes, assay or lethality results, the presence of a biological sterilization indicator 100 in a given well 14, other suitable outputs, or combinations thereof. In some embodiments, as shown in FIG. 1, the reading apparatus 12 can include a front face 18 that includes the display and/or user interface 16 and which can be angled to facilitate access to the wells 14 and/or to facilitate viewing the display 16, or other items on the face 18. Furthermore, in some embodiments, the reading apparatus 12 can include a substantially horizontal or flat top wall 20 that can facilitate stacking of multiple reading apparatuses 12 on top of one another, such that multiple reading apparatuses 12 can be operated and read simultaneously, as desired. The reading apparatus 12 and operation of the biological sterilization indicator system 10 will be described in greater detail below, with reference to FIGS. 3-5. First, the biological sterilization indicator 100 will be described in detail, with reference to FIGS. 2-4.

Biological Sterilization Indicator

Figure 2:
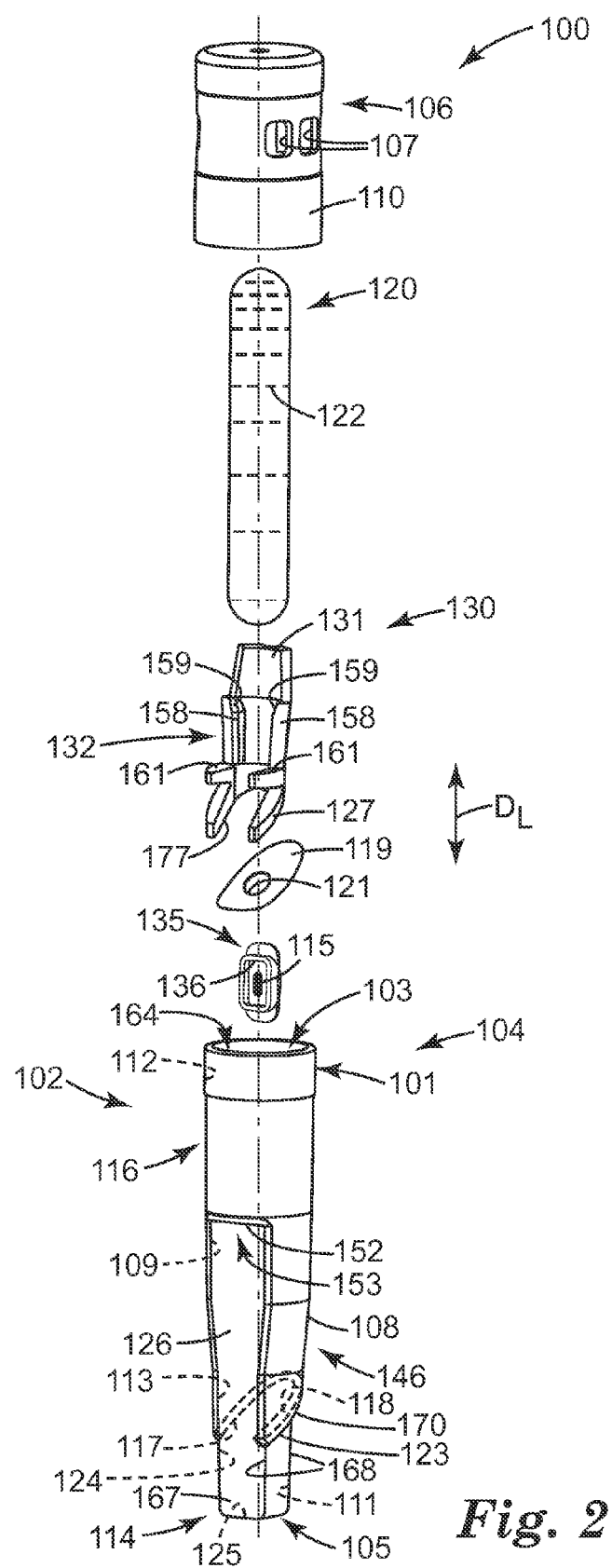
FIG. 2 is an exploded perspective view of a biological sterilization indicator of FIG. 1, the biological sterilization indicator including a housing comprising a first portion and a second portion.
Figure 3:
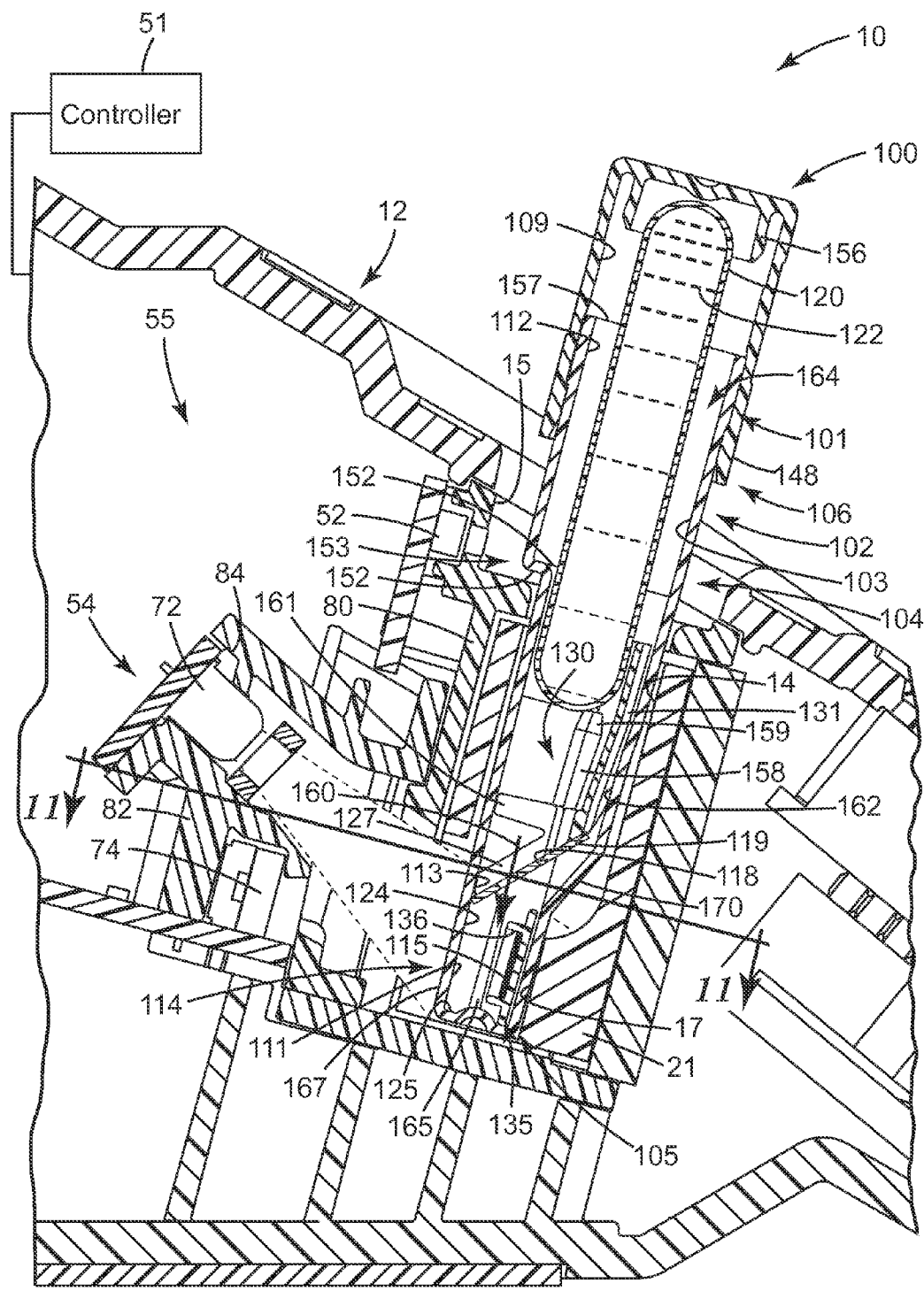
FIG. 3 is a cross-sectional side view of the biological sterilization indicator system of FIG. 1, taken along line 3-3 of FIG. 1, the biological sterilization indicator shown in a first state, and the second portion of the housing of the biological sterilization indicator shown in a first position.
Figure 4:
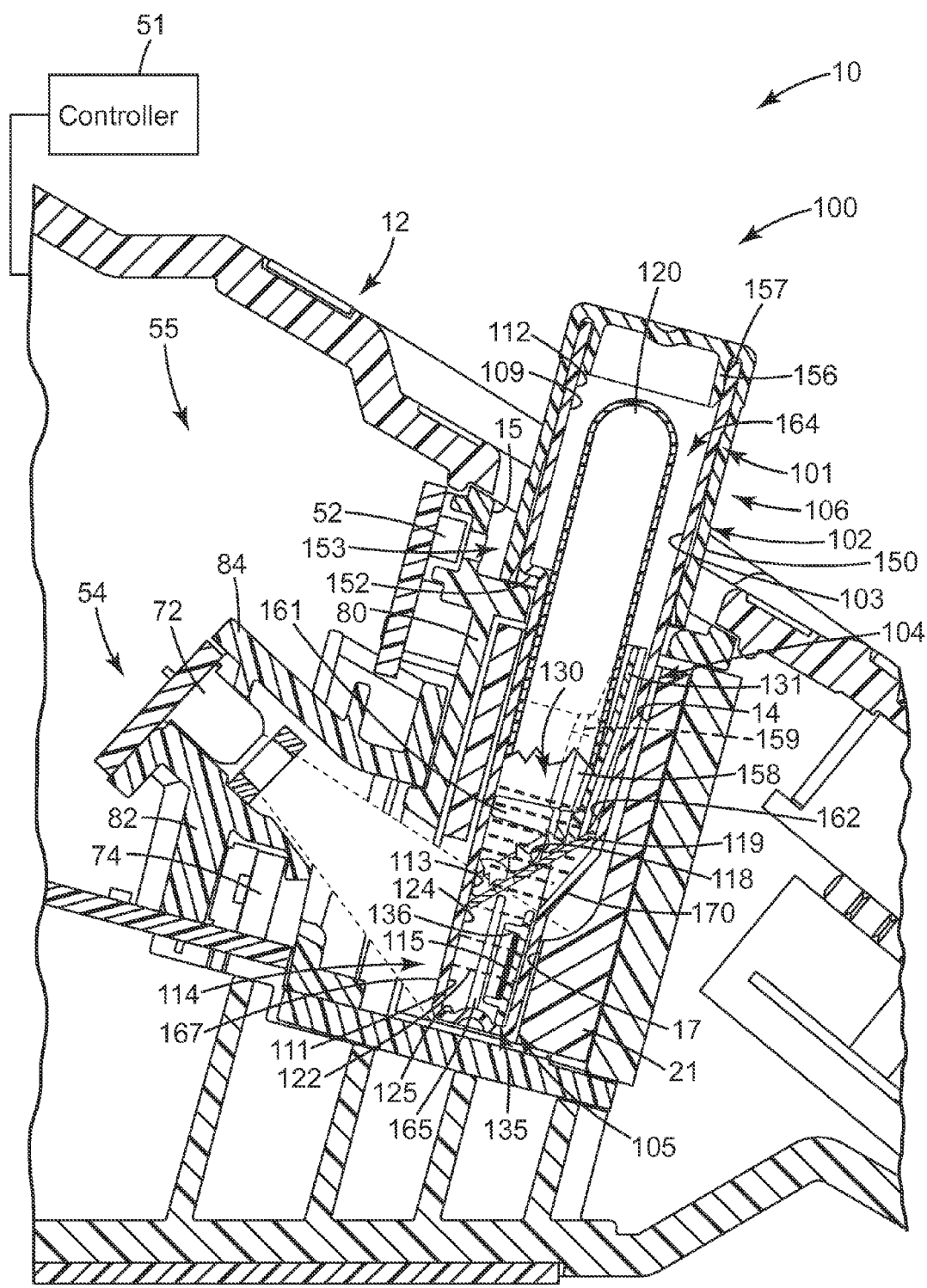
FIG. 4 is a cross-sectional side view of the biological sterilization indicator system of FIGS. 1-3, the biological sterilization indicator system shown in a second state, and the second portion of the housing of the biological sterilization indicator shown in a second position.

FIGS. 2-4 illustrate the biological sterilization indicator 100 in greater detail. Other suitable embodiments of biological sterilization indicators are described in PCT Publication Nos. WO2011/011189, entitled "Biological Sterilization Indicator and Method of Using Same"; WO2012/061229, entitled "Biological Sterilization Indicator System and Method"; WO2012/061226, entitled "Biological Sterilization Indicator and Method of Using Same"; and WO2012/061227, entitled "Biological Sterilization Indicator"; each of which is incorporated herein by reference in its entirety.

The biological sterilization indicator 100 can include a housing 102, which can include a first portion 104 and a second portion 106 (e.g., a cap) adapted to be coupled together to provide a self-contained biological sterilization indicator. In some embodiments, the first portion 104 and second portion 106 can be formed of the same materials, and in some embodiments, the first portion 104 and the second portion 106 can be formed of different materials. The housing 102 can define a reservoir 103 of the biological sterilization indicator 100 in which other components can be positioned and into which a sterilant can be directed during a sterilization process.

The housing 102 can be defined by at least one liquid impermeable wall, such as a wall 108 of the first portion 104 and/or a wall 110 of the second portion 106. It should be understood that a one-part unitary housing 102 may also be employed or that the first and second portions 104 and 106 can take on other shapes, dimensions, or relative structures without departing from the spirit and scope of the present disclosure. Suitable materials for the housing 102 (e.g., the walls 108 and 110) can include, but are not limited to, a glass, a metal (e.g., foil), a polymer (e.g., polycarbonate (PC), polypropylene (PP), polyphenylene (PPE), polythyene, polystyrene (PS), polyester (e.g., polyethylene terephthalate (PET)), polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

In some embodiments, the biological sterilization indicator 100 can further include a frangible container 120 that contains a liquid (e.g., an aqueous mixture) 122, and which is dimensioned to be received within the biological sterilization indicator 100, for example, within at least a portion of the housing 102 (e.g., at least within the first portion 104 of the housing 102). The frangible container 120 can be formed of a variety of materials, including, but not limited to, one or more of metal (e.g., foil), a polymer (e.g., any of the polymers listed above with respect to the housing 102), glass (e.g., a glass ampoule), and combinations thereof. In some embodiments, only a portion of the container 120 is frangible, for example, the container 120 can include a frangible portion or cover (e.g., a frangible barrier, film, membrane, or the like). The frangible container 120 can have a first state in which it is intact and the liquid 122 is contained therein, and a second state in which at least a portion of the container 120 is fractured. In the second state of the container 120, the liquid 122 can be in fluid communication with the reservoir 103 of the biological sterilization indicator 100, e.g., when the container 120 is positioned in the biological sterilization indicator 100.

As shown in the illustrated embodiment, the container 120 can be held in place within the biological sterilization indicator 100 and/or fractured by an insert 130, which is described in greater detail below.

The first portion 104 of the housing 102 can be adapted to house a majority of the components of the biological sterilization indicator 100, and can be referred to as a "tube," "tubular body," "base," or the like. The housing 102 can include a reservoir 103 that can be defined by one or both of the first portion 104 and the second portion 106 of the housing 102. The biological sterilization indicator 100 can further include spores or another source(s) of biological activity 115 (or a locus of spores) positioned in fluid communication with the reservoir 103. As shown in FIG. 2, the second portion 106 of the housing 102 can include one or more apertures 107 to provide fluid communication between the interior of the housing 102 (e.g., the reservoir 103) and ambience. For example, the one or more apertures 107 can provide fluid communication between the spores 115 and ambience during a sterilization process, and can serve as an inlet into the biological sterilization indicator 100 and as an inlet of a sterilant path 164 (described in greater detail below). In some embodiments, the second portion 106 of the housing 102 can be coupled to a first (e.g., open) end 101 of the first portion 104 of the housing 102, and the spores 115 can be positioned at a second (e.g., closed) end 105, opposite the first end 101, of the first portion 104 of the housing 102.

In some embodiments, a barrier or filter (e.g., a sterile barrier; not shown) can be positioned in the sterilant path 164 (e.g., at the inlet formed by the aperture 107) to inhibit contaminating or foreign organisms, objects or materials from entering the biological sterilization indicator 100. Such a barrier can include a gas-transmissive, microorganism-impermeable material, and can be coupled to the housing 102 by a variety of coupling means, including, but not limited to, an adhesive, a heat seal, sonic welding, or the like. Alternatively, the barrier can be coupled to the sterilant path 164 via a support structure (such as the second portion 106) that is coupled to the first portion 104 of the housing 102 (e.g., in a snap-fit engagement, a screw-fit engagement, a press-fit engagement, or a combination thereof). During exposure to a sterilant, the sterilant can pass through the barrier into the sterilant path 164 and into contact with the spores 115.

In some embodiments, as shown in FIG. 2, the housing 102 can include a lower portion 114 and an upper portion 116, which can be at least partially separated by an inner wall (or partial wall) 118, ledge, partition, flange, or the like, in which can be formed an opening 117 that provides fluid communication between the lower portion 114 and the upper portion 116. In some embodiments, the lower portion 114 of the first portion 104 of the housing 102 (sometimes referred to as simply "the lower portion 114" or the "the lower portion 114 of the housing 102") can be adapted to house the spores 115 or a locus of spores. In some embodiments, the lower portion 114 can be referred to as the "detection portion" or "detection region" of the housing 102, because at least a portion of the lower portion 114 can be interrogated for signs of spore growth. In addition, in some embodiments, the upper portion 116 of the first portion 104 of the housing 102 (sometimes referred to as "the upper portion 116" or the "the upper portion 116 of the housing 102" for simplicity) can be adapted to house at least a portion of the frangible container 120, particularly before activation.

In some embodiments, as shown in FIGS. 2-4, the portion of the reservoir 103 that is defined at least partially by the upper portion 116 of the housing 102 can be referred to as a first chamber (or reservoir, zone, region, or volume) 109 and the portion of the reservoir 103 that is defined at least partially by the lower portion 114 of the housing 102 can be referred to as a second chamber (or reservoir, zone, region, or volume) 111. In some embodiments, the second chamber 111 can be referred to as a "spore growth chamber" or a "detection chamber," and can include a volume to be interrogated for spore viability to determine the efficacy of a sterilization process.

The first chamber 109 and the second chamber 111 can be positioned in fluid communication with each other to allow a sterilant and the liquid 122 to move from (i.e., through) the first chamber 109 to the second chamber 111. In some embodiments, the degree of fluid connection between the first chamber 109 and the second chamber 111 (e.g., the size of an opening, such as the opening 117, connecting the first chamber 109 and the second chamber 111) can increase after, simultaneously with, and/or in response to the activation step (i.e., the liquid 122 being released from the container 120). In some embodiments, the control of fluid communication (or extent of fluid connection) between the first chamber 109 (e.g., in the upper portion 116) and the second chamber 111 (e.g., in the lower portion 114) can be provided by at least a portion of the insert 130.

The container 120 can be positioned and held in the first chamber 109 during sterilization and when the container 120 is in a first, unfractured, state. The spores 115 can be housed in the second chamber 111 and in fluid communication with ambience when the container 120 is in the first state. The first chamber 109 and the second chamber 111 can be configured such that the container 120 is not present in the second chamber 111, and particularly, not when the container 120 is in its first, unfractured, state. A sterilant can move into the second chamber 111 (e.g., via the first chamber 109) during sterilization, and the liquid 122 can move into the second chamber 111 (e.g., from the first chamber 109) during activation, when the container 120 is fractured and the liquid 122 is released into the interior of the housing 102.

As a result, when the container 120 is in the first state, the first chamber 109 and the second chamber 111 can be in fluid communication with one another, and with ambience (e.g., during sterilization). For example, the first chamber 109 and the second chamber 111 can be in fluid communication with ambience via the one or more apertures 107. In some embodiments, the first chamber 109 and the second chamber 111 can be in fluid communication with ambience in such a way that the first chamber 109 is positioned upstream of the second chamber 111 when a sterilant is entering the biological sterilization indicator 100. That is, the first chamber 109 can be positioned between the sterilant inlet (e.g., the one or more apertures 107) and the second chamber 111, and the sterilant inlet can be positioned on an opposite side of the first chamber 109 than the second chamber 111.

As shown in FIGS. 2-4, in some embodiments, the first chamber 109 can be defined by one or both of the first portion 104 and the second portion 106, particularly when the container 120 is in the first state. In addition, in some embodiments, the first chamber 109 can include a first end 112 positioned adjacent the open end 101 of the first portion 104 of the housing 102, adjacent the second portion 106 of the housing 102, and/or defined at least partially by the second portion 106 of the housing 102. The first chamber 109 can further include a second end 113 positioned adjacent and in fluid communication with the second chamber 111 and positioned toward the closed end 105 of the housing 102. The first end 112 of the first chamber 109 can be at defined by the first portion 104 and/or the second portion 106 of the housing 102.

As further shown in FIGS. 2-4, in some embodiments, the second chamber 111 can include a first end 124 positioned adjacent and in fluid communication with the first chamber 109 and positioned toward the open end 101 of the housing 102, and a second end 125 at least partially defined by, including, or positioned adjacent the closed end 105 of the housing 102.

Said another way, as shown in FIGS. 2-4, the biological sterilization indicator 100 can include a longitudinal direction $D_L$, and in some embodiments, the first chamber 109 can be positioned longitudinally above the second chamber 111.

In some embodiments, the second chamber 111 can be at least partially defined by, can include, or can be positioned adjacent the closed end 105 of the biological sterilization indicator 100. In addition, in some embodiments, the second chamber 111 can be smaller (e.g., in volume and/or cross-sectional area) than at least one of the first chamber 109 and the volume of the liquid 122 in the container 120 that will be released when the biological sterilization indicator 100 is activated. As a result, in such embodiments, the second chamber 111 can exhibit an air-lock effect where gas (e.g., air) that is present in the second chamber 111 can inhibit fluid movement into the second chamber 111. In some embodiments, as described in greater detail below, a fluid path that allows the second chamber 111 to vent to another portion of the biological sterilization indicator 100 can facilitate fluid movement into the second chamber 111.

In some embodiments, the wall 118 (sometimes referred to as a "separating wall") can be angled or slanted, for example, oriented at a non-zero and non-right angle with respect to a longitudinal direction $D_L$ of the housing 102 (e.g., where the longitudinal direction $D_L$ extends along the length of the housing 102). Such angling or slanting of the wall 118 can facilitate the movement of the liquid 122 from the upper portion 116 to the lower portion 114 after sterilization and after the container 120 has been broken to release the liquid 122.

As shown in FIG. 2, in some embodiments, the wall 118 can be at least partially formed by a change in the inner dimension of the housing 102. For example, as shown, the wall 118 can be formed by a decrease in a cross-sectional area from a first longitudinal position in the first chamber 109 to a second longitudinal position in the second chamber 111. In addition, by way of example only, the internal cross-sectional shape of the housing 102 can change at the transition from the first chamber 109 to the second chamber 111 from being substantially round (e.g., with one flat side that makes up less than 50% of the perimeter) in the first chamber 109 to substantially parallelepipedal (e.g., substantially square) in the second chamber 111.

Furthermore, in some embodiments, the wall 118 can also be at least partially formed by a change in the outer dimension of the housing 102. As shown in FIG. 2, in some embodiments, the housing 102 includes a step (or ledge, overhang, transition, or the like) 123 that is angled consistently with the wall 118 (if the wall 118 is angled), and which includes a change in the outer shape and dimension of the housing 102. However, it should be understood that in some embodiments, even if the inner dimension of the housing 102 changes to create a second chamber 111 that has a different cross-sectional shape or dimension than the first chamber 109, the outer shape and dimension of the housing 102 need not change, or change consistently with the change in the inner shape and/or dimension. For example, in some embodiments, the step 123 can be oriented substantially perpendicularly with respect to the longitudinal direction $D_L$.

In some embodiments, the reservoir 103 has a volume of at least about 0.5 milliliters (mL), in some embodiments, at least about 1 mL, and in some embodiments, at least about 1.5 mL. In some embodiments, the reservoir 103 has a volume of no greater than about 5 mL, in some embodiments, no greater than about 3 mL, and in some embodiments, no greater than about 2 mL.

In some embodiments, the frangible container 120 has a volume of at least about 0.25 mL, in some embodiments, at least about 0.5 mL, and in some embodiments, at least about 1 mL. In some embodiments, the frangible container 120 has a volume of no greater than about 5 mL, in some embodiments, no greater than about 3 mL, and in some embodiments, no greater than about 2 mL.

In some embodiments, the volume of the liquid 122 contained in the frangible container 120 is at least about 50 microliters, in some embodiments, at least about 75 microliters, and in some embodiments, at least about 100 microliters. In some embodiments, the volume of the liquid 122 contained in the frangible container 120 is no greater than about 5 mL, in some embodiments, no greater than about 3 mL, and in some embodiments, no greater than about 2 mL.

In some embodiments, the first chamber 109 (i.e., formed by the upper portion 116 of the first portion 104 of the housing 102) has a volume of at least about 500 microliters (or cubic millimeters), in some embodiments, at least about 1000 microliters, in some embodiments, at least about 2000 microliters, and in some embodiments, at least about 2500 microliters. In some embodiments, the first chamber 109 has a volume of no greater than about 5000 microliters, in some embodiments, no greater than about 4000 microliters, and in some embodiments, no greater than about 3000 microliters. In some embodiments, the first chamber 109 has a volume of about 2790 microliters, or 2800 microliters.

In some embodiments, the second chamber 111 (i.e., formed by the lower portion 114 of the first portion 104 of the housing 102) has a volume of at least about 5 microliters, in some embodiments, at least about 20 microliters, and in some embodiments, at least about 35 microliters. In some embodiments, the second chamber 111 has a volume of no greater than about 250 microliters, in some embodiments, no greater than about 200 microliters, in some embodiments, no greater than about 175 microliters, and in some embodiments, no greater than about 100 microliters. In some embodiments, the second chamber 111 has a volume of about 208 microliters, or 210 microliters.

In some embodiments, the volume of the second chamber 111 is at least about 5% of the volume of the first chamber 109, and in some embodiments, at least about 7%. In some embodiments, the volume of the second chamber 111 is no greater than about 20% of the volume of the first chamber 109, in some embodiments, no greater than about 15%, in some embodiments, no greater than about 12%, and in some embodiments, no greater than about 10%. In some embodiments, the volume of the second chamber 111 is about 7.5% of the volume of the first chamber 109.

In some embodiments, the volume of the second chamber 111 is no greater than about 60% of the volume of the liquid 122 housed in the container 120, in some embodiments, no greater than about 50%, and in some embodiments, no greater than about 25%. In some embodiments, designing the second chamber 111 to have a volume that is substantially less than that of the liquid 122 housed in the container 120 can ensure that the additional liquid volume can compensate for unintended evaporation.

In some embodiments, the first chamber 109 (i.e., formed by the upper portion 116 of the first portion 104 of the housing 102) has a cross-sectional area (or average cross-sectional area) at the transition between the first chamber 109 and the second chamber 111, or at the position adjacent the second chamber 111, of at least about 25 mm$^2$; in some embodiments, at least about 30 mm$^2$; and in some embodiments, at least about 40 mm$^2$. In some embodiments, the first chamber 109 has a cross-sectional area at the transition between the first chamber 109 and the second chamber 111, or at the position adjacent the second chamber 111, of no greater than about 100 mm$^2$, in some embodiments, no greater than about 75 mm$^2$, and in some embodiments, no greater than about 50 mm$^2$ In some embodiments, the second chamber 111 (i.e., formed by the lower portion 114 of the first portion 104 of the housing 102) has a cross-sectional area at the transition between the first chamber 109 and the second chamber 111, or at the position adjacent the first chamber 109, of at least about 5 mm$^2$, in some embodiments, at least about 10 mm$^2$, and in some embodiments, at least about 15 mm$^2$. In some embodiments, the second chamber 111 has a cross-sectional area (or average cross-sectional area) of no greater than about 30 mm$^2$, in some embodiments, no greater than about 25 mm$^2$, and in some embodiments, no greater than about mm$^2$ In some embodiments, the cross-sectional area of the second chamber 111 at the transition between the first chamber 109 and the second chamber 111 can be no greater than about 60% of the cross-sectional area of the first chamber 109 at the transition, in some embodiments, no greater than about 50%, in some embodiments, no greater than about 40%, and in some embodiments, no greater than about 30%.

In some embodiments, the biological sterilization indicator 100 can further include a substrate 119. In some embodiments, as shown in FIGS. 2-4, the substrate 119 can be dimensioned to be positioned adjacent the wall 118, and particularly, to rest atop the wall 118. The substrate 119 can be positioned between the upper portion 116 and the lower portion 114 of the biological sterilization indicator 100 and, in some embodiments, can at least partially define the first chamber 109 and the second chamber 111. As such, in some embodiments, the substrate 119 can be positioned between the container 120 and the spores 115. In some embodiments, the substrate 119 can be positioned in the first chamber 109, or on a first chamber side of the wall 118, such that the substrate 119 is not positioned in the second chamber 111.

In addition, the substrate 119 can be positioned to minimize diffusion of an assay signal (e.g., fluorescence) out of the second chamber 111. In some embodiments, depending on the material makeup of the substrate 119, the substrate 119 can also absorb dyes, indicator reagents, or other materials from solution that may inhibit accurate reading of a signal from the biological sterilization indicator 100 (i.e., "inhibitors"). In some embodiments, as shown in FIG. 2, the substrate 119 can include one or more apertures 121, which can be configured to control (i.e., facilitate and/or limit, depending on number, size, shape, and/or location) fluid movement between the first chamber 109 and the second chamber 111 of the biological sterilization indicator 100, and particularly, which can facilitate movement of the liquid 122 to the spores 115 when the container 120 is fractured. By way of example only, particular benefits or advantages were observed when the aperture 121 was positioned front of (or "forward of") the center of the substrate 119, as shown. In the embodiment illustrated in FIGS. 1-4, the "front" of the biological sterilization indicator 100 or components therein can generally be described as being toward a flat face 126. In general, the "front" of the biological sterilization indicator 100 can refer to the portion of the biological sterilization indicator 100 that will be interrogated by the reading apparatus 12.

In addition, by way of example only, the aperture 121 is illustrated as being circular or round; however, other cross-sectional aperture shapes are possible and within the scope of the present disclosure. Furthermore, by way of example only, and as shown in FIG. 2, the substrate 119 is shaped to substantially fill the first chamber cross-sectional area at the transition between the first chamber 109 and the second chamber 111. However, other shapes of the substrate 119 are possible and can be adapted to accommodate the housing 102, the first chamber 109, the second chamber 111, the wall 118, or another component of the biological sterilization indicator 100.

In some embodiments, the substrate 119 can be formed of a variety of materials to accomplish one or more of the above functions. Examples of substrate materials can include, but are not limited to, cotton, glass wool, cloth, nonwoven polypropylene, nonwoven rayon, nonwoven polypropylene/rayon blend, nonwoven nylon, nonwoven glass fiber or other nonwoven fibers, filter papers, microporous hydrophobic and hydrophilic films, glass fibers, open celled polymeric foams, and semi-permeable plastic films (e.g., particle filled films, thermally induced phase separation (TIPS) membranes, etc.), and combinations thereof. For example, in embodiments in which the substrate 119 can be used to selectively concentrate one more indicator reagents (e.g., bromocresol purple (BCP)), the substrate 119 can be formed of a charged nylon (such as a reprobing, charged transfer membrane available from GE Water & Process Technologies, Trevose, Pa., under the trade designation "MAGNAPROBE" (e.g., 0.45 micron pore size, 30 cm×3 m roll, Catalog No. NPOHY00010, Material No. 1226566)).

The substrate 119 is described in greater detail in PCT Publication Nos. WO2012/061226 and WO2012/061227, each of which is incorporated herein by reference in its entirety. Examples of methods and systems that can employ the substrate 119 are also described in PCT Publication Nos. WO2012/061212, entitled "Method of Detecting a Biological Activity;" and WO2012/061213, entitled "Method of Detecting a Biological Activity," each of which is incorporated herein by reference in its entirety.

In some embodiments, at least a portion of one or more of the insert 130, the wall 118, and/or the substrate 119, or an opening therein, can provide fluid communication between the first chamber 109 (e.g., in the upper portion 116) and the second chamber 111 (e.g., in the lower portion 114), and/or can control the fluid communication between the first chamber 109 and the second chamber 111 (e.g., by controlling the extent of fluid connection between the first chamber 109 and the second chamber 111).

The biological sterilization indicator 100 can include a first fluid path 160 that can be positioned to fluidly couple the first chamber 109 and the second chamber 111, and which can allow sterilant (e.g., during sterilization, when the container 120 is in a first, unfractured state) and/or the liquid 122 (e.g., after sterilization and during activation, when the container 120 is in a second, fractured, state) to reach the spores 115. In the illustrated embodiment the first fluid path 160 can generally be defined by one or more of the following: (1) the insert 130, e.g., via an aperture 177 described below, an opening formed in the insert 130, and/or any open spaces around the insert 130, such as between the insert 130 (e.g., a front portion thereof) and the housing 102; (2) the wall 118, e.g., the aperture 117 defined by the wall 118; (3) the substrate 119, e.g., the aperture 121 formed therein, or any open spaces around the substrate 119, such as between the substrate 119 (e.g., a front portion thereof) and the housing 102; (4) the housing 102, e.g., any openings or spaces formed therein; and combinations thereof. As a result, the first fluid path 160 is generally represented by an arrow, as shown in FIG. 3.

The biological sterilization indicator 100 can further include a second fluid path 162 positioned to fluidly couple the second chamber 111 with another chamber or portion of the biological sterilization indicator 100, such as the first chamber 109. The second fluid path 162 can be further positioned to allow gas that was previously present in the second chamber 111 to be displaced and to exit the second chamber 111, for example, when the sterilant and/or the liquid 122 is moved into the second chamber 111. As such, the second fluid path 162, which is described in greater detail below, can serve as an internal vent in the biological sterilization indicator 100.

In some embodiments, the substrate 119 can provide a physical barrier or blockage between the first chamber 109 and the second chamber 111 which can allow for at least one of the following: controlling the sterilant delivery rate/kill rate at which sterilant is delivered into the second chamber 111; controlling the diffusion of spores 115 and/or detectable products out of the second chamber 111; controlling the delivery rate of the liquid 122 to the second chamber 111 (and to the spores 115) when the container 120 is in the second, fractured, state; or a combination thereof.

Because, in some embodiments, the substrate 119 can provide a physical barrier to delivering the liquid 122 to the second chamber 111 during activation (i.e., when the container 120 is in the second state), aperture 121 in the substrate 119 and/or the angle of the substrate 119 can be controlled to effect a desired liquid delivery rate. In addition, or alternatively, the second fluid path 162 can provide a vent for any gas (e.g., air) that is trapped in the second chamber 111 to facilitate moving the liquid 122 through or past the substrate 119 and into the second chamber 111 when desired.

In addition, or alternatively, the housing 102 can be configured (e.g., formed of an appropriate material and/or configured with microstructured grooves or other physical surface modifications) to facilitate moving the liquid 122 to the second chamber 111 when desired.

In some embodiments, the liquid 122 can include a nutrient medium for the spores, such as a germination medium that will promote germination of surviving spores. In some embodiments, the liquid 122 can include water (or another solvent) that can be combined with nutrients to form a nutrient medium. Suitable nutrients can include nutrients necessary to promote germination and/or growth of surviving spores and may be provided in a dry form (e.g., powdered form, tablet form, caplet form, capsule form, a film or coating, entrapped in a bead or other carrier, another suitable shape or configuration, or a combination thereof) in the reservoir 103, for example, in a region of the biological sterilization indicator 100 near the spores 115.

The nutrient medium can generally be selected to induce germination and initial outgrowth of the spores, if viable. The nutrient medium can include one or more sugars, including, but not limited to, glucose, fructose, cellibiose, or the like, or a combination thereof. The nutrient medium can also include a salt, including, but not limited to, potassium chloride, calcium chloride, or the like, or a combination thereof. In some embodiments, the nutrient can further include at least one amino acid, including, but not limited to, at least one of methionine, phenylalanine, and tryptophan.

In some embodiments, the nutrient medium can include indicator molecules or reagents, for example, indicator molecules having optical properties that change in response to germination or growth of the spores. Suitable indicator molecules or reagents can include, but are not limited to, pH indicator molecules (e.g., bromocresol purple (BCP), bromocresol green (BCG), chlorophenol red (CPR), bromthymol blue (BTB), bromophenol blue (BPB), other sulfonephthalein dyes, methyl red, or combinations thereof), enzyme substrates (e.g., 4-methylumbelliferyl-α-D-glucoside), DNA binding dyes, RNA binding dyes, other suitable indicator molecules, or a combination thereof. In some embodiments, the combination of bromcresol purple and 4-methylumbelliferyl-α-D-glucoside represents an example of a pair of indicator reagents that can be employed together. This combination can be used to detect a first biological activity such as the fermentation of a carbohydrate to acid end products and a second biological activity such as α-D-glucosidase enzyme activity, for example. These activities can indicate the presence or absence of a viable spore following the exposure of a biological sterilization indicator to a sterilization process, for example. The bromcresol purple can be used at a concentration of about 0.03 g/L, for example, in an aqueous mixture. The 4-methylumbelliferyl-α-D-glucoside can be used, for example, at a concentration of about 0.05 to about 0.5 g/L (e.g., about 0.05 g/L, about 0.06 g/L, about 0.07 g/L, about 0.08 g/L, about 0.09 g/L, about 0.1 g/L, about 0.15 g/L, about 0.2 g/L, about 0.25 g/L, about 0.3 g/L, about 0.35 g/L, about 0.4 g/L, about 0.45 g/L, about 0.5 g/L), for example, in an aqueous mixture.

As shown in FIGS. 2-4, the biological sterilization indicator 100 can further include an insert 130. In some embodiments, the insert 130 can be adapted to hold or carry the container 120, such that the container 120 is held intact in a location separate from the spores 115 during sterilization. That is, in some embodiments, the insert 130 can include (or function as) a carrier 132 for the container 120, particularly, before the container 120 is broken during the activation step (i.e., the step in which the liquid 122 is released from the container 120 and introduced to the spores 115, which can occur after a sterilization process). In some embodiments, the insert 130 can be further adapted to allow the container 120 to move at least somewhat in the housing 102, e.g., longitudinally with respect to the housing 102. The insert 130 of the embodiment illustrated in FIGS. 1-4 is described in greater detail below. Examples of other suitable inserts and carriers are described in PCT Publication No. WO2011/011189.

In some embodiments, the biological sterilization indicator 100 can further include a spore carrier 135, as shown in FIGS. 2-4. However, in some embodiments, the insert 130 can be modified to include a portion adapted to house the spores 115. For example, in some embodiments, the insert 130 and the spore carrier 135 can be integrally formed as one insert comprising a first portion adapted to hold and eventually fracture the container 120, when desired, and a second portion adapted to house the spores 115 in a region of the biological sterilization indicator 100 that is separate from the container 120 during sterilization (i.e., prior to fracture).

As shown in FIGS. 2-4, the spore carrier 135 can include a spore reservoir 136 (which can also be referred to as a depression, divot, well, recess, or the like), in which the spores 115 can be positioned, either directly or on a substrate. In embodiments employing a nutrient medium that is positioned to be mixed with the liquid 122 when it is released from the container 120, the nutrient medium can be positioned near or in the spore reservoir 136, and the nutrient medium can be mixed with (e.g., dissolved in) the water when the water is released from the container 120. By way of example only, in embodiments in which the nutrient medium is provided in a dry form, the dry form can be present within the reservoir 103, the spore reservoir 136, on a substrate for the spores, or a combination thereof. In some embodiments, a combination of liquid and dry nutrient media can be employed.

In some embodiments, the spore reservoir 136 has a volume of at least about 1 microliter, in some embodiments, at least about 5 microliters, and in some embodiments, at least about 10 microliters. In some embodiments, the spore reservoir 136 has a volume of no greater than about 250 microliters, in some embodiments, no greater than about 175 microliters, and in some embodiments, no greater than about 100 microliters.

As shown in FIGS. 3 and 4, in some embodiments, the biological sterilization indicator 100 can further include a rib or protrusion 165 that can be coupled to or integrally formed with a wall 108 of the housing 102, which can be positioned to maintain the spore carrier 135 in a desired location in the housing 102 and/or at a desired angle or orientation, for example, with respect to detection systems (e.g., optical detection systems) of the reading apparatus 12.

As shown in FIGS. 2-4, the second portion 106 of the housing 102 can be adapted to be coupled to the first portion 104. For example, as illustrated in FIGS. 1-4, the second portion 106 can be adapted to be coupled to the upper portion 116 (e.g., the first end 101) of the first portion 104 of the housing 102. In some embodiments, as shown in FIGS. 1-4, the second portion 106 can be in the form of a cap that can be dimensioned to receive at least a portion of the first portion 104 of the housing 102.

As shown in FIG. 3, before activation, the second portion 106 can be in a first "unactivated" position 148 with respect to the first portion 104, and the container 120 can be in a first, intact, state. As shown in FIG. 4, the second portion 106 of the housing 102 can be moved to a second "activated" position 150 (e.g., where the second portion 106 is fully depressed) with respect to the first portion 104, and the container 120 can be in a second, fractured, state. For example, after sterilization, the biological sterilization indicator 100 can be activated by moving the second portion 106 from the first position 148 to the second position 150 (i.e., a sufficient amount) to cause fracturing of the container 120 and to release the liquid 122 from the container 120, to allow the liquid 122 to be in fluid communication with the spores 115. The biological sterilization indicator 100 can be activated prior to positioning the biological sterilization indicator 100 in the well 14 of the reading apparatus 12, after positioning the biological sterilization indicator 100 in the well 14, or as the biological sterilization indicator 100 is positioned in the well 14 (i.e., the biological sterilization indicator 100 can be slid into place in the well 14, and the second portion 106 can continue to be pressed until it is in its second position 150, e.g., in which the bottom of the well 14 provides sufficient resistance to move the second portion 106 to its second position 150). The second position 150 can be located closer to the closed end 105 of the first portion 104 of the biological sterilization indicator 100 than the first position 148.

A variety of coupling means can be employed between the first portion 104 and the second portion 106 of the housing 102 to allow the first portion 104 and the second portion 106 to be removably coupled to one another, including, but not limited to, gravity (e.g., one component can be set atop another component, or a mating portion thereof), screw threads, press-fit engagement (also sometimes referred to as "friction-fit engagement" or "interference-fit engagement"), snap-fit engagement, magnets, adhesives, heat sealing, other suitable removable coupling means, and combinations thereof. In some embodiments, the biological sterilization indicator 100 need not be reopened and the first portion 104 and the second portion 106 need not be removably coupled to one another, but rather can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. One of ordinary skill in the art will recognize that some of the permanent or semi-permanent coupling means can also be adapted to be removable, and vice versa, and are categorized in this way by way of example only.

As shown in FIGS. 3-4, the second portion 106 can be movable between a first longitudinal position 148 with respect to the first portion 104 and a second longitudinal position 150 with respect to the first portion 104; however, it should be understood that the biological sterilization indicator 100 could instead be configured differently, such that the first and second positions 148 and 150 are not necessarily longitudinal positions with respect to one or both of the first portion 104 and the second portion 106 of the housing 102.

The second portion 106 can further include a seal 156 (e.g., a projection, a protrusion, a flap, flange, o-ring, or the like, or combinations thereof) that can be positioned to contact the first end 101 of the first portion 104, and particularly, an open upper end 157 of the first portion 104 to close or seal (e.g., hermetically seal) the biological sterilization indicator 100 after the second portion 106 has been moved to the second position 150 and the liquid 122 has been released from the container 120. The seal 156 can take a variety of forms and is shown in FIGS. 3 and 4 by way of example as forming an inner ring or cavity that together with the wall 110 of the second portion 106 is dimensioned to receive the upper end 157 of the first portion 104 of the housing 102 to seal the biological sterilization indicator 100. In some embodiments, one or both of the seal 156 and the upper end 157 can further include a structure (e.g., a protrusion) configured to engage the other of the upper end 157 and the seal 156, respectively, in order to couple the second portion 106 of the housing 102 to the first portion 104 of the housing 102.

In addition, in some embodiments, the second portion 106 of the housing 102 can be coupled to the first portion 104 of the housing 102 to seal the biological sterilization indicator 100 from ambience after activation. Such sealing can inhibit contamination, evaporation, or spilling of the liquid 122 after it has been released from the container 120, and/or can inhibit contamination of the interior of the biological sterilization indicator 100.

The seal 156 can be configured to have a length in the longitudinal direction $D_L$ of the biological sterilization indicator 100 to accommodate different degrees or levels of closure. That is, in some embodiments, the "second position" 150 of the second portion 106 of the housing 102 can be any position in which at least a portion of the seal 156 has engaged a portion (e.g., the upper end 157) of the first portion 104 of the housing 102 such that the interior of the biological sterilization indicator 100 is sealed from ambience. The biological sterilization indicator 100 and the biological sterilization indicator system 10 can correspondingly be configured such that if the reading apparatus 12 detects that the second portion 106 has moved to the second position 150, the user knows that the seal 156 is engaged.

The insert 130 will now be described in greater detail, with particular reference to FIGS. 2-4.

As shown in FIG. 3, before activation, the second portion 106 can be in a first position 148 with respect to the first portion 104. In the first position 148, the container 120 can be held intact in a position separate from the lower portion 114 or the spores 115, and the liquid 122 can be contained within the container 120.

As shown in FIG. 4, after sterilization, the biological sterilization indicator 100 can be activated to release the liquid 122 from the container 120 to move the liquid 122 to the spores 115. That is, the second portion 106 of the housing 102 can be moved to a second position 150 with respect to the first portion 104. When the second portion 106 is moved from the first position 148 to the second position 150, the seal 156 of the second portion 106 of the housing 102 can engage the upper end 157 of the first portion 104 to seal the reservoir 103 of the biological sterilization indicator 100 from ambience. In such embodiments, the second portion 106 can reversibly engage the first portion 104 in the second position 150, and in some embodiments, the second portion 106 can irreversibly engage the first portion 104. However, it should be understood that the structures and coupling means for the first portion 104 and the second portion 106 are shown in FIGS. 3 and 4 by way of example only, and any of the above-described coupling means can instead be employed between the first portion 104 and the second portion 106 of the housing 102.

The insert 130 can be adapted to hold or carry the container 120, such that the container 120 is held intact in a location separate from the spores 115 during sterilization. That is, as mentioned above, in some embodiments, the insert 130 can include (or function as) a carrier 132 for the container 120, particularly, before the container 120 is broken during the activation step (i.e., the step in which the liquid 122 is released from the container 120 and introduced to the spores 115, which typically occurs after a sterilization process).

In addition, the insert 130 can be adapted to hold the container 120 intact in a position in the housing 102 that maintains at least a minimal spacing (e.g., a minimal cross-sectional area of space) between the container 120 and the housing 102 and/or between the container 120 and any other components or structures in the housing 102 (e.g., at least a portion of the insert 130, such as the carrier 132, etc.), for example, to maintain a substantially constant sterilant path 164 in the biological sterilization indicator 100. In some embodiments, the insert 130 can be adapted to hold the container 120 in a substantially consistent location in the housing 102.

In some embodiments, as shown in FIG. 2, at least a portion of the housing 102 can include a tapered portion 146 in which the housing 102 (e.g., the wall 108 and/or an inner surface thereof) generally tapers in the longitudinal direction $D_L$ of the housing 102. As a result, the cross-sectional area in the housing 102 can generally decrease along the longitudinal direction $D_L$.

In some cases, without providing the means to maintain at least a minimal spacing around the container 120 (e.g., between the container 120 and surrounding structure), there can be a possibility that the container 120 can become positioned in the housing 102 (e.g., in the tapered portion 146) in such a way that it obstructs or blocks the sterilant path 164. However, the biological sterilization indicator 100 of the present disclosure is designed to inhibit this from occurring. For example, in the embodiment illustrated in FIGS. 1-4, the insert 130 (and particularly, the carrier 132) can be configured to hold the container 120 out of the tapered portion 146 of the housing 102, such that at least a minimal cross-sectional area is maintained around the container 120 in any orientation of the biological sterilization indicator 100 prior to activation. For example, in the embodiment illustrated in FIGS. 1-4, even if the biological sterilization indicator 100 is tipped upside down, the container 120 may fall away from contact with the insert 130, but in no orientation, is the container 120 moved any closer to the tapered portion 146, or the spores 115 until activation of the biological sterilization indicator 100. In addition, until activation, at least a minimal spacing (and particularly, a cross-sectional area of that spacing) between the container 120 and the housing 102 and/or the insert 130 can be maintained to provide a substantially constant sterilant path 164, for example, around the container 120.

In some embodiments, the relative sizing and positioning of the components of the biological sterilization indicator 100 can be configured such that, before activation, the container 120 is held intact in a substantially consistent location in the biological sterilization indicator 100. Such a configuration can provide a substantially constant sterilant path 164 and can maintain the container 120 in a position such that the container 120 is not able to move substantially, if at all, in the biological sterilization indicator 100 before activation.

In some embodiments, at least a portion of the insert 130 can be adapted to allow the container 120 to move in the housing 102, e.g., longitudinally with respect to the housing 102, between a first (longitudinal) position in which the container 120 is intact and a second (longitudinal) position in which at least a portion of the container 120 is fractured. By way of example only, the insert 130 can include one or more projections or arms 158 (two projections 158 spaced about the container 120 are shown by way of example only) adapted to hold and support the container 120 before activation and to allow the container 120 to move in the housing 102 during activation, for example, when the second portion 106 is moved with respect to the first portion 104 of the housing 102. The projections 158 can also be adapted (e.g., shaped and/or positioned) to fracture the container 120 in a desired manner when the biological sterilization indicator is activated. As a result, the insert 130 can sometimes function to hold the container 120 intact before activation, and can function to break the container 120 during activation. As a result, the insert 130, or a portion thereof, can sometimes be referred to as a "carrier" (e.g., the carrier 132) and/or a "breaker."

By way of example only, the projections 158 are shown in FIGS. 2-4 as being coupled to a base or support 127 adapted to abut the separating wall 118. For example, the base 127 can be dimensioned to be received in the reservoir 103 and dimensioned to sit atop, abut, or otherwise cooperate with or be coupled to the separating wall 118. Such coupling with an internal structure of the biological sterilization indicator 100 can provide the necessary resistance and force to break the container 120 when desired. In some embodiments, however, the insert 130 does not include the base 127, and the projections 158 can be coupled to or form a portion of the housing 102. In some embodiments, the insert 130 is integrally formed with or provided by the housing 102.

As shown in FIGS. 2-4, the insert 130 can further include a sidewall 131 that connects the projections 158 and is shaped to accommodate an inner surface of the housing 102 and/or an outer surface of the container 120. Such a sidewall 131 can provide support and rigidity to the projections 158 to aid in reliably breaking the container 120 in a consistent manner. The sidewall 131 can also be shaped and dimensioned to guide the container 120 in a desired manner as it is moved in the housing 102 during activation, for example, to contact the projections 158 in a desired way to reliably fracture the container 120.

The sidewall 131 and/or the wall 108 of the housing 102 (or an inner surface thereof) can also be shaped to define at least a portion of the second fluid path 162 of the biological sterilization indicator 100, for example, between an outer surface of the insert 130 and an inner surface of the housing 102. In some embodiments, a channel can be formed in one or both of the insert 130 and the housing 102 (e.g., in the wall 108 of the housing 102) that together define the second fluid path 162.

The second fluid path 162 can provide an internal vent within the biological sterilization indicator 100 to allow trapped air to escape the second chamber 111 of the biological sterilization indicator 100 as the liquid 122 is released from the container 120 (1) during activation, to facilitate moving the liquid 122 into the spore chamber 111 of the biological sterilization indicator 100; and/or (2) during sterilization, to facilitate moving a sterilant into the spore chamber 111 (i.e., into contact with the spores 115). The second fluid path 162 is described in greater detail in PCT Publication No. WO2012/061226.

By way of example only, the projections 158 are illustrated as being relatively rigid and stationary. That is, in some embodiments, the projections 158 may not be adapted to substantially flex, distort, deform or otherwise heed to the container 120 as it is moved in the housing 102. Rather, in some embodiments, as shown in FIGS. 2-4, the projections 158 can each be configured to have an upper end 159 atop which the container 120 can be positioned and held intact before activation. As shown in FIG. 3, in some embodiments, the projections 158 can be positioned to fracture the container 120 at its radiused end, for example, when an oblong or capsule-shaped container 120 is employed.

One potential advantage of having the projections 158 form at least a portion of the carrier 132 is that the bottom of the container 120 can be unrestricted when the container 120 is fractured, such that the liquid 122 can be released from the container 120 and moved toward the spores 115 with relative ease and reliability.

In such embodiments, the insert 130 can be used to fracture the container 120 in a direction that is substantially perpendicular to a flat side of the container 120, for example, when an oblong or capsule-shaped container 120 is employed. In such embodiments, fracturing the container 120 along its side can be achieved, along with maintaining some open spaces around the lower end of the container 120 to facilitate moving the liquid 122 from the container 120 to the proximity of the spores 115 when the container 120 is fractured.

As mentioned above, the projections 158 can be adapted to fracture the container 120 as the container 120 is moved with respect to the housing 102 (e.g., along the longitudinal direction $D_L$), for example, in response to the second portion 106 of the housing 102 being moved with respect to the first portion 104 of the housing 102 (e.g., from the first position 148 to the second position 150).

In some embodiments, the projections 158 can include one or more edges (e.g., tapered edges) or points or otherwise be configured to concentrate the crushing force to increase the pressure on the container 120 in the regions adjacent the projections 158, and to facilitate fracturing the container 120 more easily and in one or more desired regions. In some embodiments, such concentration of force can reduce the total effort or force needed to move the second portion 106 with respect to the first portion 104 and to fracture the container 120 (or a portion thereof).

As shown in FIGS. 2-4, the projections 158 are integrally formed with the base 127 of the insert 130; however, it should be understood that the projections 158 can instead be integrally formed with the wall 108 of the housing 102. In addition, in some embodiments, the projections 158 can be coupled to the housing 102, or the projections 158 and the base 127 can be provided by separate inserts. In such embodiments, the projections 158 can each be a separate insert, or multiple projections 158 can be provided by one or more inserts. In addition, the insert 130 can be configured to abut the wall 118 to inhibit movement of the first portion the insert 130 into the proximity of the spores 115 (e.g., the lower portion 114 of the housing 102).

In addition, in some embodiments, as shown in FIGS. 2-4, the projections 158 can extend a distance along the longitudinal direction $D_L$, and the length and/or thickness (e.g., which can vary along the length) of the projections 158 can be tailored to control the fracturing of the container 120 at a desired position in the housing 102 and in a desired manner. The configuration of the projections 158 is shown in FIGS. 2-4 by way of example only.

In general, each of the projections 158 is shown by way of example only as increasing in thickness (e.g., inwardly toward the container 120 or center of the housing 102) along the longitudinal direction $D_L$ toward the spores 115. Such a configuration can decrease the cross-sectional area that is available to the container 120, as the container 120 is moved toward the spores 115, for example, in response to the second portion 106 being moved to the second position 150.

Furthermore, the biological sterilization indicator 100 is shown in FIGS. 2-4 as including two projections 158 and a sidewall 131 by way of example only, but it should understood that one projection 158 or as many as structurally possible, and other configurations, can be employed. In addition, the projections 158 can be shaped and dimensioned as desired, depending on the shape and dimensions of the housing 102, on the shape and dimensions of the container 120, on the shape and dimensions of the insert 130, and/or on the manner and position desired for fracturing the container 120.

As mentioned above, in some embodiments, at least a portion of the housing 102 can be tapered (see, e.g., the tapered portion 146 in FIG. 2). As a result, the cross-sectional area in the housing 102 can generally decrease along the longitudinal direction $D_L$. However, it should be understood that the inner dimensions of the housing 102 can generally decrease in the tapered portion along the longitudinal direction $D_L$ without the outer dimensions of the housing 102 changing. In some embodiments, the outer dimensions of the housing 102 can be uniform along its length, even though the inner portion of the housing 102 tapers along its length. In some embodiments, the one or more projections 158 alone can vary in thickness (i.e., toward the container 120, e.g., in a radial direction) along the longitudinal direction $D_L$, such that the cross-sectional area available to the container 120 generally decreases as the container 120 is moved in the housing 102 during activation, even though the dimensions of the housing 102 do not change (e.g., even if the housing 102 does not include any tapered portion 146, either internally or externally).

As shown in FIGS. 2-4, the upper end 159 of each of the projections 158 includes a rounded, curved or arcuate surface, which can facilitate movement of the container 120 from the first position 148 in which the container 120 sits at least partially above the upper end 159 of the projection 158 to a position in which the container 120 is forced, at least partially, into the smaller cross-sectional area region in between the projections 158 (or between the wall 108 of the housing 102 and one or more projections 158). In addition, the rounded upper end 159 can inhibit premature breakage of the container 120, which can inhibit premature activation of the biological sterilization indicator 100 (i.e., premature release of the liquid 122).

In some embodiments, as shown in FIG. 3, the insert 130 can be sized and shaped to allow the container 120 to be held above the projections 158 and out from the region adjacent any portion of an inwardly-facing surface of one or more of the projections 158 to inhibit accidental or premature activation of the biological sterilization indicator 100. Such a configuration can also inhibit inadvertent breakage due to shock or material expansion (e.g., due to exposure to heat during a sterilization process).

As shown in FIGS. 2-4, the carrier 132, which can be formed at least partially by the upper ends 159 of the projections 158, can be configured to hold a bottom portion of the container 120, and the projections 158 can be positioned to fracture the container 120 at a location near the bottom of the container 120 as it is positioned in the housing 102. Such a configuration can allow the container 120 to be broken near its bottom and can facilitate removal of the liquid 122 from the container 120, which can enhance the availability of the liquid 122 to the spores 115, and can enhance the reliability of releasing the liquid 122 into fluid communication with the spores 115 (e.g., with the spore reservoir 136). Such a configuration is shown by way of example only, however, and it should be understood that the projections 158 can be configured and positioned to fracture the container 120 in any desired manner.

Some embodiments of the present disclosure provide optimal and safe breakage of a frangible container 120 with relatively low force, while enhancing transfer of liquid 122 to the spore region (e.g., the second chamber 111 of the housing 102) of the biological sterilization indicator 100, and/or enhancing containment of the liquid 122 in the spore region of the biological sterilization indicator 100. In addition, some embodiments of the present disclosure operate to drive a liquid to a particular area of the biological sterilization indicator 100, such as a spore detection area (e.g., the second chamber 111) of the biological sterilization indicator 100.

In the embodiment illustrated in FIGS. 1-4, the insert 130 is illustrated as including two projections 158 that are approximately equally spaced about the container 120 and/or about the sidewall 131. However, in some embodiments, the sidewall 131 can include one solid (e.g., substantially annular or semi-annular) projection 158 that extends radially inwardly from the sidewall 131. Furthermore, in some embodiments, the sidewall 131 can extend further around the inner surface of the housing 102 than what is illustrated. However, employing one or more narrower (e.g., in an angular dimension) projections 158, such as those shown in FIGS. 2-4, can provide a substantially constant or substantially unobstructed sterilant path 164 around the container 120.

Whether the insert 130 includes one or more projections 158 or sidewalls 131, the insert 130 can be configured to hold the container 120 in the housing 102 in a consistent location to provide a substantially constant sterilant path 164 during sterilization. For example, rather than allowing the container 120 to move or roll around (e.g., radially and/or longitudinally) in the housing 102 before activation (e.g., during sterilization), the insert 130 can hold the container 120 in a substantially consistent position, which can allow a sterilant a substantially consistent and relatively unobstructed path between an outer surface of the container 120 and an inner surface of the housing 102, with little or no opportunity for inadvertent blockage.

As shown in FIGS. 2-4, the insert 130 can further include one or more projections 161 positioned substantially horizontally or perpendicularly with respect to the longitudinal direction $D_L$ of a biological sterilization indicator (e.g., when the insert 130 is positioned in a biological sterilization indicator). The projections 161 can be referred to as "second projections" or "horizontal projections," while the projections 158 used to hold and/or break the container 120 can be referred to as "first projections" or "vertical projections." The second projections 161 are not angled downwardly like the base 127. As a result, the second projections 161 can be used for a variety of purposes. For example, the second projections 161 can stabilize the insert 130 (e.g., aid in holding the insert 130 in a desired position in the housing 102 of the biological sterilization indicator 100) under the force of fracturing the container 120. In addition, the second projections 161 can function to retain and/or collect fractured portions of the container 120 after it has been fractured to inhibit movement of such portions into the proximity of spores in the biological sterilization indicator, which could negatively affect spore growth and/or detection of spore growth. Other shapes and configurations of the second projections 161 can be employed that still allow for fluid movement down to the spores 115 while inhibiting solid movement down to the spores 115.

In some embodiments, the insert 130 (e.g., the base 127) can be adapted for one or more of facilitating or allowing fluid movement (e.g., movement of the liquid 122) into the second chamber 111 (i.e., the lower portion 114) of the housing 102; minimizing movement of fractions or portions (e.g., solids) of the fractured container 120 into the second chamber 111 of the housing 102, that is, collecting and/or retaining portions of the fractured container 120; and/or minimizing diffusion of the spores 115 and/or signals out of the second chamber 111 of the housing 102. For example, in some embodiments, the base 127 can be configured to function as a grate or filter. In some embodiments, spore growth is determined by fluorescent indicators/molecules (e.g., fluorophores) or other markers. In some embodiments, if the liquid level after activation in the biological sterilization indicator 100 is above the location of the spores 115, such molecules or markers, or the spores 115 themselves, can move or diffuse away from or out of the spore reservoir 136 and, potentially, out of the second chamber 111 of the housing 102. As a result, portions of the biological sterilization indicator 100 (e.g., the insert 130) can be configured to inhibit undesirable diffusion of various indicators, molecules, and/or markers out of the second chamber 111 of the biological sterilization indicator 100. In some embodiments, as described above, the substrate 119 can also inhibit such undesirable diffusion.

In the embodiment illustrated in FIGS. 1-4, the base 127 of the insert 130 is generally U-shaped or horseshoe-shaped and includes a central aperture 177 (see FIG. 2) that facilitates the movement of sterilant toward the spores 115 during sterilization and the movement of the liquid 122 toward the spores 115 during activation. The horseshoe shape of the base 127 can increase the opening between the upper portion 116 (i.e., the first chamber 109) and the lower portion 114 (i.e., the second chamber 111) of the housing 102; however, this shape is shown by way of example only, and other shapes can be employed.

In some embodiments, the insert 130 can be described as including one or more downwardly-extending projections 127 adapted to abut or otherwise couple to the wall 118 or another internal structure of the biological sterilization indicator 100 to provide a base or support for the insert 130, to inhibit movement of the insert 130 and container 120 relative to the housing 102 before activation, and/or to provide resistance or force to aid in breaking the container 120 during activation. As a result, in some embodiments, the base 127 can instead be referred to as "third projections" 127.

As shown in FIGS. 2-4, in some embodiments, the insert 130 can be configured to reside entirely in the first chamber 109 of the biological sterilization indicator 100, such that the insert 130 does not extend into the second chamber 111 where it could potentially interfere with interrogation or detection processes. Furthermore, the insert 130 can be configured to inhibit movement of other portions of the biological sterilization indicator 100 (e.g., the fractured container 120) into the second chamber 111.

The insert 130 illustrated in FIGS. 2-4 is generally symmetrical about a central longitudinal line of symmetry, such that there are two identical first projections 158, two identical second projections 161, and two identical third projections 127. However, the insert 130 need not include any lines of symmetry, and the first projections 158 need not be the same as one another, the second projections 161 need not be the same as one another, and the third projections 127 need not be the same as one another. The insert 130, and the various projections 158, 161 and 127 can be sized and positioned to control the sterilant path 164, for example, to tailor the kill/survival rate of the biological sterilization indicator 100, to inhibit inadvertent fracture of the container 120, to facilitate movement of the container 120 in the housing 120, to mate with or engage the housing 102, and/or to control the breakage of the container 120.

By way of example only, the insert 130 illustrated in FIGS. 2-4 is shown as being a unitary device that includes at least the following: means for holding the container 120 before activation, for fracturing the container 120 during activation; for allowing movement of the container 120 in the housing 102; for providing a substantially constant sterilant path 164, for collecting and/or retaining portions of the fractured container 120 after activation (or at least partially inhibiting movement of portions of the fractured container 120 into the second chamber 111 of the housing 102); and/or for minimizing diffusion of the spores 115 and/or signals from the second chamber 111 to the upper portion 116 of the housing 102 after activation. However, it should be understood that in some embodiments, the insert 130 can include multiple portions that may not be part of a single, unitary device, and each of the portions can be adapted to do one or more of the above functions.

The insert 130 is referred to as an "insert" because in the embodiment illustrated in FIGS. 2-4, the device that performs the above functions is a device that can be inserted into the reservoir 103 (and, particularly, the first chamber 109) of the housing 102. However, it should be understood that the insert 130 can instead be provided by the housing 102 itself or another component of the biological sterilization indicator 100 and need not necessarily be insertable into the housing 102. The term "insert" will be described throughout the present disclosure for simplicity, but it should be understood that such a term is not intended to be limiting, and it should be appreciated that other equivalent structures that perform one or more of the above functions can be used instead of, or in combination with, the insertable insert 130. Furthermore, in the embodiment illustrated in FIGS. 2-4, the insert 130 is both insertable into and removable from the housing 102, and particularly, into and out of the first portion 104 (and the first chamber 109) of the housing 102. However, it should be understood that even if the insert 130 is insertable into the housing 102, the insert 130 need not be removable from the housing 102, but rather can be fixedly coupled to the housing 102 in a manner that inhibits removal of the insert 130 from the housing 102 after positioning the insert 130 in a desired location.

In some embodiments, at least a portion of the housing 102, for example, the lower portion 114 of the housing 102, can be transparent to an electromagnetic radiation wavelength or range of wavelengths (e.g., transparent to visible light when visible-light optical detection methods are employed), which can facilitate detection of spore growth. That is, in some embodiments, as shown in FIGS. 2-4, at least a portion of the housing 102 can include or form a detection window 167.

In addition, in some embodiments, as shown in FIG. 2, at least a portion of the housing 102, for example, the lower portion 114 can include one or more planar walls 168. Such planar walls 168 can facilitate detection (e.g., optical detection) of spore growth. In addition, in the embodiment illustrated in FIGS. 1-5, the wall 108 of the first portion 104 of the housing 102 can include one or more stepped regions, such as the step 123 (described above), a flat-to-round transition, transition zone, or step, 152 (described in greater detail below), and a tapered wall, or step, 170. The tapered wall 170 can function to reduce the overall thickness and size of the lower portion, or detection portion, 114 of the housing 102, such that the outer dimensions of the housing 102 are reduced in addition to the inner dimensions. Such a reduction in size and/or thickness of the lower portion 114 of the biological sterilization indicator 100 can facilitate detection. In addition, having one or more features, such as the steps and/or tapered walls 123, 152, 170 can allow the biological sterilization indicator 100 to be coupled to a reader or detection device (e.g., the well 14 of the reading apparatus 12) in only one orientation, such that the biological sterilization indicator 100 is "keyed" with respect to such a device, which can minimize user error and enhance reliability of a detection process. In some embodiments, one or more portions of the biological sterilization indicator 100 can be keyed with respect to a reading apparatus.

The biological sterilization indicator of the present disclosure generally keeps the liquid 122 and the spores 115 separate but in relatively close proximity (e.g., within the self-contained biological sterilization indicator 100) during sterilization, such that the liquid 122 and the spores 115 can be readily combined after exposure to a sterilization process. The liquid 122 and the spores 115 can be incubated during a detection process (e.g., the reading apparatus 12 can incubate the biological sterilization indicator 100), or the biological sterilization indicator 100 can be incubated prior to a detection process. In some embodiments, when incubating the spores with the liquid 122, an incubation temperature above room temperature can be used. For example, in some embodiments, the incubation temperature is at least about 37° C., in some embodiments, the incubation temperature is at least about 50° C. (e.g., 56° C.), and in some embodiments, at least about 60° C. In some embodiments, the incubation temperature is no greater than about 60° C., in some embodiments, no greater than about 50° C., and in some embodiments, no greater than about 40° C.

A detection process can be adapted to detect a detectable change from the spores 115 (e.g., from within the spore reservoir 136) or the liquid 122 surrounding the spores 115. That is, a detection process can be adapted to detect a variety of characteristics, including, but not limited to, electromagnetic radiation (e.g., in the ultraviolet, visible, and/or infrared bands), fluorescence, luminescence, light scattering, electronic properties (e.g., conductance, impedance, or the like, or combinations thereof), turbidity, absorption, Raman spectroscopy, ellipsometry, or the like, or a combination thereof. Detection of such characteristics can be carried out by one or more of a fluorimeter, a spectrophotometer, colorimeter, or the like, or combinations thereof. In some embodiments, such as embodiments that measure fluorescence, visible light, etc., the detectable change is measured by detecting at a particular wavelength.

The spores and/or the liquid 122 can be adapted (e.g., labeled) to produce one or more of the above characteristics as a result of a biochemical reaction that is a sign of spore viability. As a result, no detectable change (e.g., as compared to a baseline or background reading) can signify an effective sterilization process, whereas a detectable change can signify an ineffective sterilization process. In some embodiments, the detectable change can include a rate at which one or more of the above characteristics is changing (e.g., increasing fluorescence, decreasing turbidity, etc.).

In some embodiments, spore viability can be determined by exploiting enzyme activity. As described in Matner et al., U.S. Pat. No. 5,073,488, entitled "Rapid Method for Determining Efficacy of a Sterilization Cycle and Rapid Read-out Biological Indicator," which is incorporated herein by reference, enzymes can be identified for a particular type of spore in which the enzyme has particularly useful characteristics that can be exploited to determine the efficacy of a sterilization process. Such characteristics can include the following: (1) the enzyme, when subjected to sterilization conditions which would be sufficient to decrease a population of $1 \times 10^6$ test microorganisms by about 6 logs (i.e., to a population of about zero as measured by lack of outgrowth of the test microorganisms), has a residual activity which is equal to "background" as measured by reaction with a substrate system for the enzyme; and (2) the enzyme, when subjected to sterilization conditions sufficient only to decrease the population of $1 \times 10^6$ test microorganisms by at least 1 log, but less than 6 logs, has enzyme activity greater than "background" as measured by reaction with the enzyme substrate system. The enzyme substrate system can include a substance, or mixture of substances, which is acted upon by the enzyme to produce a detectable enzyme-modified product, as evident by a detectable change.

In some embodiments, the biological sterilization indicator 100 can be assayed in a single-side mode, where the biological sterilization indicator 100 includes only one detection window (e.g., detection window 167 of FIG. 2) that is positioned, for example, near the spores 115. In some embodiments, however, the biological sterilization indicator 100 can include more than one detection window (e.g., a window formed by all or a portion of both parallel walls 168 of the lower portion 114 of the housing 102), such that the biological sterilization indicator 100 can be assayed via more than one detection window. In embodiments employing multiple detection windows, the detection windows can be positioned side-by-side (similar to a single-side mode), or the detection windows can be oriented at an angle (e.g., 90 degrees, 180 degrees, etc.) with respect to one another.

In general, the spores 115 are positioned within the spore reservoir 136 which is in fluid communication with the reservoir 103. In some embodiments, the spore reservoir 136 forms a portion of the reservoir 103 (e.g., a portion of the second chamber 111). As shown in FIG. 3, the reservoir 103 is in fluid communication with ambience (e.g., via the aperture 107) during sterilization to allow sterilant to enter the reservoir 103 during a sterilization process to sterilize the spores 115. The container 120 can be configured to contain the liquid 122 during sterilization to inhibit the liquid 122 from being in fluid communication with the spores 115, the reservoir 103, and the sterilant during sterilization.

Various details of the spores 115 and/or spore reservoir 136 will now be described in greater detail.

In some embodiments, the spores 115 can be positioned directly in the lower portion 114 of the housing 102, or the spores 115 can be positioned in a spore reservoir, such as the spore reservoir 136 (e.g., provided by the spore carrier 135 in the embodiment illustrated in FIGS. 2-4). Whether the spores 115 are positioned directly in the lower portion 114 of the housing 102 or in a spore reservoir, the spores 115 can be provided in a variety of ways. In some embodiments, the spores 115 can be in a spore suspension that can be positioned in a desired location in the biological sterilization indicator 100 and dried down. In some embodiments, the spores 115 can be provided on a substrate (not shown) that can be positioned and/or secured in a desired location in the biological sterilization indicator 100. Some embodiments can include a combination of spores 115 provided in a dried down form and spores 115 provided on a substrate.

In some embodiments, the substrate can be positioned to support the spores 115 and/or to help maintain the spores 115 in a desired locus. Such a substrate can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a reflective material (e.g., a metal foil), a glass, a porcelain, a ceramic, a gel-forming material (e.g., guar gum), or combinations thereof. In addition, or alternatively, such a substrate can include or be coupled to a hydrophilic coating to facilitate bringing the liquid 122 into intimate contact with the spores 115 (e.g., when the liquid 122 employed is aqueous). In addition, or alternatively, such a hydrophilic coating can be applied to any fluid path positioned to fluidly couple the liquid 122 and the spores 115. In some embodiments, in addition to, or in lieu of a hydrophilic coating, a hydrophobic coating can be applied to other portions of the housing 102 (e.g., the lower portion 114 of the housing 102) and/or spore reservoir 136, such that the liquid 122 is preferentially moved into contact with the spores 115.

Some embodiments of the biological sterilization indicator 100 do not include the spore carrier 135. Rather, the spore reservoir 136 is provided by the lower portion 114 of the housing 102 itself, and the spores 115 can be positioned in the lower portion 114, adsorbed to an inner surface or wall of the lower portion 114, or combinations thereof. In some embodiments, the spores 115 can be provided on a substrate that is positioned in the lower portion 114 of the housing 102.

In some embodiments, the spores 115 can be positioned in one locus of spores or in a plurality of loci of spores, all of which can be positioned either in the reservoir 103, in the lower portion 114 of the housing 102, and/or in the spore reservoir 136. In some embodiments, having multiple loci of spores can maximize the exposure of the spores to sterilant and to the liquid 122, can improve manufacturing (e.g., placement of the spores can be facilitated by placing each locus of spores in a depression within the biological sterilization indicator 100), and can improve detection characteristics (e.g., because spores in the middle of one large locus of spores may not be as easily detected). In embodiments employing a plurality of loci of spores, each locus of spores can include a different, known number of spores, and/or each locus of spores can include different spores, such that a plurality of spore types can be tested. By employing multiple types of spores, the biological sterilization indicator 100 can be used for a variety of sterilization processes and a specific locus of spores can be analyzed for a specific sterilization process, or the multiple types of spores can be used to further test the effectiveness, or confidence, of a sterilization process.

In addition, in some embodiments, the biological sterilization indicator 100 can include a plurality of spore reservoirs 136, and each spore reservoir 136 can include one or more loci of spores 115. In some embodiments employing a plurality of spore reservoirs 136, the plurality of spore reservoirs 136 can be positioned in fluid communication with the reservoir 103.

In some embodiments, the spores 115 can be covered with a cover (not shown) adapted to fit in or over the spores 115 and/or the spore reservoir 136. Such a cover can help maintain the spores within the desired region of the biological sterilization indicator 100 during manufacturing, sterilization and/or use. The cover, if employed, can be formed of a material that does not substantially impede a detection process, and/or which is at least partially transmissive to electromagnetic radiation wavelengths of interest. In addition, depending on the material makeup of the cover, in some embodiments, the cover can facilitate wicking the liquid 122 (e.g., the nutrient medium) along the spores 115. In some embodiments, the cover can also contain features for facilitating fluid flow into the spore reservoir 136 (or to the spores 115), such as capillary channels, hydrophilic microporous fibers or membranes, or the like, or a combination thereof. In addition, in some embodiments, the cover can isolate a signal, or enhance the signal, which can facilitate detection. Such a cover can be employed whether the spores 115 are positioned within the spore reservoir 136 or directly in the lower portion 114 of the housing 102. In addition, such a cover can be employed in embodiments employing a plurality of loci of spores. The cover can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a glass, a porcelain, a ceramic, a gel-forming material (e.g., guar gum), or combinations thereof.

In some embodiments, the biological sterilization indicator 100 can further include a modified inner surface, such as a reflective surface, a white surface, a black surface, or another surface modification suitable to optimize the optical properties of the surface. A reflective surface (e.g., provided by a metal foil) can be positioned to reflect a signal sent into the spore reservoir 136 from an assaying or detection device and/or to reflect any signal generated within the spore reservoir 136 back toward the assaying device. As a result, the reflective surface can function to improve (e.g., improve the intensity of) a signal from the biological sterilization indicator 100. Such a reflective surface can be provided by an inner surface of the housing 102; a material coupled to the inner surface of the housing 102; an inner surface the spore reservoir 136; a material coupled to the inner surface of the spore reservoir 136; or the like; or the reflective surface can form a portion of or be coupled to a spore substrate; or a combination thereof.

Similarly, in some embodiments, the biological sterilization indicator 100 can further include a white and/or black surface positioned to increase and/or decrease a particular signal sent into the spore reservoir 136 from an assaying device and/or to increase and/or decrease a particular signal generated within the spore reservoir 136. By way of example only, a white surface can be used to enhance a signal, and a black surface can be used to reduce a signal (e.g., noise).

In some embodiments, the spores 115 can be positioned on a functionalized surface to promote the immobilization of the spores 115 on the desired surface. For example, such a functionalized surface can be provided by an inner surface of the housing 102, an inner surface of the spore reservoir 136, can form a portion of or be coupled to a spore substrate, or the like, or a combination thereof.

In some embodiments, the spores 115 are positioned (e.g. applied by coating or another application method) on a microstructured or microreplicated surface (e.g., such microstructured surfaces as those disclosed in Halverson et al., PCT Publication No. WO 2007/070310, Hanschen et al., US. Publication No. US 2003/0235677, and Graham et al., PCT Publication No. WO 2004/000569, all of which are incorporated herein by reference). For example, such a microstructured surface can be provided by an inner surface of the housing 102, can be provided by an inner surface of the spore reservoir 136, can form a portion of or be coupled to a spore substrate, or the like, or a combination thereof.

In some embodiments, the biological sterilization indicator 100 can further include a gel-forming material positioned to be combined with the spores 115 and the liquid 122 when the liquid 122 is released from the container 120. For example, the gel-forming material can be positioned near the spores 115 (e.g., in the spore reservoir 136), in the lower portion 114 of the housing 102, can form a portion of or be coupled to a spore substrate, or the like, or a combination thereof. Such a gel-forming material can form a gel (e.g., a hydrogel) or a matrix comprising the spores and nutrients when the liquid 122 comes into contact with the spores. A gel-forming material (e.g., guar gum) can be particularly useful because it has the ability to form a gel upon hydration, it can aid in localizing a signal (e.g., fluorescence), it can anchor the spores 115 in place, it can help minimize diffusion of the spores 115 and/or a signal from the spore reservoir 136, and/or it can enhance detection.

In some embodiments, the biological sterilization indicator 100 can further include an absorbent or a wicking material. For example, the wicking material can be positioned near the spores 115 (e.g., in the spore reservoir 136), can form at least a portion of or be coupled to a spore substrate, or the like, or a combination thereof. Such a wicking material can include a porous wicking pad, a soaking pad, or the like, or a combination thereof, to facilitate bringing the liquid 122 into intimate contact with the spores.

In some embodiments, the frangible container 120 can be configured to facilitate fracturing of the frangible container 120 in a desired manner. For example, in some embodiments, a lower portion of the frangible container 120 can be formed of a thinner and/or weaker material, such that the lower portion preferentially fractures over another portion of the frangible container 120. In addition, in some embodiments, the frangible container 120 can include a variety of features positioned to facilitate fracturing of the frangible container 120 in a desired manner, including, but not limited to, a thin and/or weakened area, a score line, a perforation, or the like, or combinations thereof.

The frangible container 120 can have a first closed state in which the liquid 122 is contained within the frangible container 120 and a second open state in which the frangible container 120 has fractured and the liquid 122 is released into the reservoir 103 and/or the spore reservoir 136, and in fluid communication with the spores 115.

In some embodiments, the biological sterilization indicator 100 can be activated (e.g., the second portion 106 can be moved to the second position 150) manually. In some embodiments, the biological sterilization indicator 100 can be activated by the reading apparatus 12 (e.g., as the biological sterilization indicator 100 is positioned in the reading apparatus 12). In some embodiments, the biological sterilization indicator 100 can be activated with a device (e.g., an activation device) independent of the reading apparatus 12, for example, by positioning the biological sterilization indicator 100 in the device prior to positioning the biological sterilization indicator 100 in a well 14 of the reading apparatus 12. In some embodiments, the biological sterilization indicator 100 can be activated by a combination of two or more of the reading apparatus 12, a device independent of the reading apparatus 12, and manual activation.

One or both of the biological sterilization indicator 100 and another device, such as the reading apparatus 12 can be further configured to inhibit premature or accidental fracturing of the frangible container 120. For example, in some embodiments, the biological sterilization indicator 100, activation device, or reading apparatus 12 can include a lock or locking mechanism that is positioned to inhibit the second portion 106 of the housing 102 from moving into the second position 150 until desired. In such embodiments, the biological sterilization indicator 100 cannot be activated until the lock is moved, removed or unlocked. In addition, or alternatively, in some embodiments, the biological sterilization indicator 100, activation device, and/or reading apparatus 12 can include a lock or locking mechanism that is positioned to inhibit the second portion 106 of the housing 102 from moving from the second position 150 back into the first position 148 after activation.

In some embodiments, as shown in FIGS. 2-4, at least a portion of the housing can be flat (e.g., the parallel walls 168), and can be substantially planar with respect to the spore reservoir 136, and one or both of the parallel walls 168 or a portion thereof (e.g., the detection window 167) can be sized such that at least one dimension of the wall 168 (or detection window 167) substantially matches at least one dimension of the spore reservoir 136 and/or the locus of spores 115. Said another way, the wall 168 or a portion thereof (e.g., the detection window 167) can include a cross-sectional area that is substantially the same size as the cross-sectional area of the spore reservoir 136 and/or the locus of spores 115. Such size matching between the wall 168/detection window 167 and the spore reservoir 136 and/or the locus of spores 115 can maximize the signal detected during a detection or assaying process. Alternatively, or in addition, the wall 168 or detection window 167 can be sized to match the reservoir 103 (e.g., at least one dimension or the cross-sectional areas can be sized to match). Such size matching between detection zones can improve spore assaying and detection.

The biological sterilization indicator 100 illustrated in FIGS. 2-4, at least the portion of the biological sterilization indicator 100 where the spores 115 are positioned, is relatively thin (i.e., the "z dimension" is minimized), such that an optical path from the spores to the wall 168 (or detection window 167) is minimized and/or any effect of interfering substances in the liquid 122 (or nutrient medium) is minimized In use, the biological sterilization indicator 100 can be placed along with a sterilizing batch for a sterilization process. During sterilization, a sterilant is in fluid communication with the reservoir 103 (i.e., the first chamber 109 and the second chamber 111), the spore reservoir 136, and the spores 115 primarily via the sterilant path 164, such that sterilant can reach the spores to produce sterilized spores. In addition, during sterilization, the frangible container 120 is in a closed state, held intact at least partially by the carrier 132 of the insert 130. When the frangible container 120 is in a closed state, the liquid 122 is protected from the sterilant and is not in fluid communication with the reservoir 103 (particularly, the second reservoir 111 formed at least partially by the lower portion 114 of the housing 102), the spore reservoir 136, the spores 115, or the sterilant path 164.

Following sterilization, the effectiveness of the sterilization process can be determined using the biological sterilization indicator 100. The second portion 106 of the housing 102 can be unlocked, if previously locked in the first position 148, and moved from the first position 148 (see FIG. 3) to the second position 150 (see FIG. 4) to cause activation of the biological sterilization indicator 100. Such movement of the second portion 106 can cause the frangible container 120 to move in the housing 102, for example, along the longitudinal direction $D_L$ from a position above the upper ends 159 of the projections 158 to a position within the interior of the projections 158, which can cause the frangible container 120 to fracture. Fracturing the frangible container 120 can change the frangible container 120 from its closed state to its open state and release the liquid 122 into the reservoir 103, and into fluid communication with the spore reservoir 136 and the spores 115. The liquid 122 can either include nutrient medium (e.g., germination medium) for the spores, or the liquid 122 can contact nutrient medium in a dry form (e.g., in a powdered or tablet form) to form nutrient medium, such that a mixture including the sterilized spores and nutrient medium is formed. The mixture can then be incubated prior to or during a detection or assaying process, and the biological sterilization indicator 100 can be interrogated for signs of spore growth.

To detect a detectable change in the spores 115, the biological sterilization indicator 100 can be assayed immediately after the liquid 122 and the spores 115 have been combined to achieve a baseline reading. After that, any detectable change from the baseline reading can be detected. The biological sterilization indicator 100 can be monitored and measured continuously or intermittently. In some embodiments, a portion of, or the entire, incubating step may be carried out prior to measuring the detectable change. In some embodiments, incubation can be carried out at one temperature (e.g., at 37° C., at 50-60° C., etc.), and measuring of the detectable change can be carried out at a different temperature (e.g., at room temperature, 25° C., or at 37° C.).

The readout time of the biological sterilization indicator 100 (i.e., the time to determine the effectiveness of the sterilization process) can be, in some embodiments, less than 8 hours, in some embodiments, less than 1 hour, in some embodiments, less than 30 minutes, in some embodiments, less than 15 minutes, in some embodiments, less than 5 minutes, and in some embodiments, less than 1 minute.

Biological Sterilization Indicator System

The biological sterilization indicator system 10 will now be described with reference to FIGS. 3-5. FIGS. 3 and 4 illustrate the biological sterilization indicator system 10 of FIG. 1 in cross-section, taken along line 3-3 of FIG. 1, and FIG. 5 illustrates a block diagram of one embodiment of the reading apparatus 12.

The phrase "reading apparatus" generally refers to one or more devices that operate to "read" a biological sterilization indicator 100 to detect whether the spores 115 of the biological sterilization indicator 100 survived a sterilization process, as a means of judging the efficacy of a sterilization process. The phrase "reading apparatus" is meant to encompass any combination of mechanical and electronic components necessary to perform such a detection. In addition, in the present disclosure, the reading apparatus 12, or a portion thereof, is configured to detect whether the biological sterilization indicator 100 has been activated. As a result, a first device, or portion of the reading apparatus 12, can be dedicated to determining an activation status of the biological sterilization indicator 100, and a second device, or another portion of the reading apparatus 12, can be dedicated to determining the efficacy of a sterilization process. When more than one device is employed as the reading apparatus 12, the devices need not be directly coupled together. As a result, even though the phrase "reading apparatus" is used throughout as being configured to detect activation and sterilization efficacy, it should be understood that such a disclosure also includes when a first device, or reading apparatus, is used to detect activation, and a second device, or reading apparatus, is used to detect sterilization efficacy. However, particular advantages can be found when one single device is used to detect both activation and sterilization efficacy.

Figure 5:
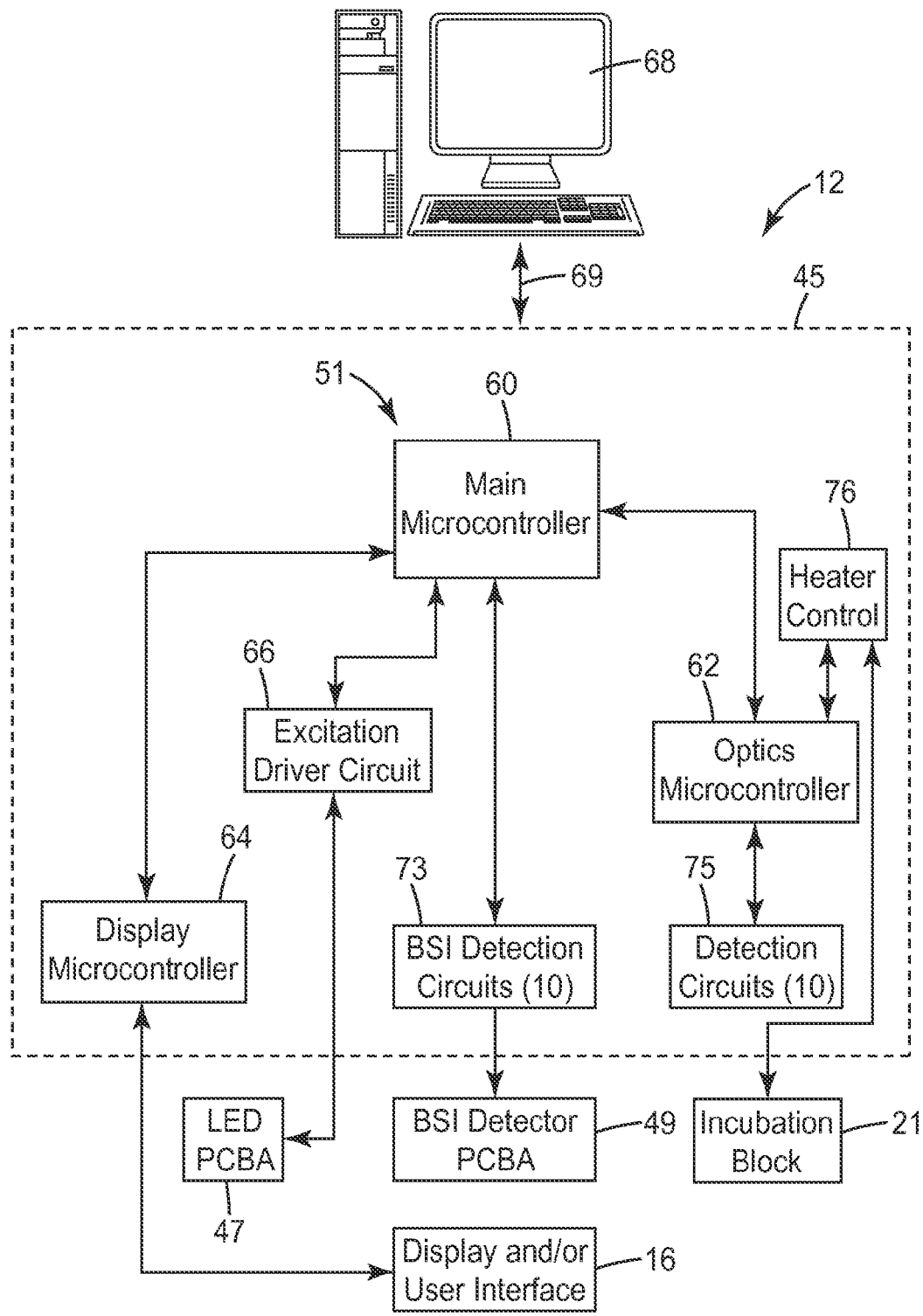
FIG. 5 is a schematic block diagram of the reading apparatus of FIG. 1.

As shown in FIG. 5, in some embodiments, the reading apparatus 12 can synchronously process multiple biological sterilization indicators 100 without user intervention. In addition, the reading apparatus 12 can combine the incubation site and reader site to a common location. Fluorescence values can be read for each well 14 independently. As shown in FIGS. 3-5, in some embodiments, the reading apparatus 12 can include an incubator block 21, which can maintain stable and consistent temperature for incubation of biological sterilization indicators 100 in multiple wells 14. By way of example only, the reading apparatus 12 is illustrated as including ten wells 14 that can each independently process a biological sterilization indicator 100. Each well 14 of the reading apparatus 12 can include a corresponding display area (e.g., an LCD display) on the display 16 of the reading apparatus 12 to display biological sterilization indicator processing results to a user, well 14 number, time remaining, temperature, and/or other general information.

As shown in FIGS. 3 and 4, in some embodiments, the incubator block 21 can be dimensioned and shaped (e.g., "keyed") to accommodate the shape of the biological sterilization indicator 100, or a portion thereof (e.g., especially the outer shape of the lower portion 114 of the biological sterilization indicator 100). Such a design of the incubator block 21 can allow stable and consistent incubation of the biological sterilization indicator 100, which can allow for stable assay or interrogation results (e.g., stable fluorescence readings), while still allowing the biological sterilization indicator 100 to present an unobstructed detection window 167 (e.g., a flat detection window 167) to the optics/detection system(s) of the reading apparatus 12 (e.g., the second sensor 54, described in greater detail below). In some embodiments, the incubator block 21 can be one integrally formed component, with an individual portion or section configured to interact independently with each well 14 of the reading apparatus 12. In some embodiments, each well 14 can be equipped with its own, independent and separate incubator block 21. No matter the mechanical configuration of the incubator block(s) 12 for the entire reading apparatus 12, each incubator block 21 that corresponds to a well 14 of the reading apparatus 12 can be operated independently of adjacent incubator blocks 21 and can be thermally isolated and insulated from such adjacent incubator blocks 21, as needed (e.g., via an air gap).

In some embodiments, the reading apparatus 12 can include three printed circuit board assemblies (PCBAs), namely, a main PCBA 45, a light-emitting diode (LED) PCBA 47, and a biological sterilization indicator (BSI) detector PCBA 49. FIG. 5 shows a breakdown of the primary circuit modules within the main PCBA 45. The main PCBA 45 can provide the control functions for the LED PCBA 47 and the BSI detector PCBA 49, as well as the display 16 and heater (e.g., a resistive flexible heater), and can coordinate their interactions and dependencies. The heater can be thermally coupled to the incubator block 21, which can be thermally coupled to one or more wells 14 of the reading apparatus 12.

In embodiments employing ten wells 14, the LED PCBA 47 can house ten LEDs (e.g., UV LEDs)—one for each sample well 14. The LEDs can serve as an excitation source for a biological sterilization indicator 100. The BSI detector PCBA 49 can include ten first sensors 52, which can be used to detect the presence of a biological sterilization indicator 100 in a corresponding well 14, as well as the approximate position of the second portion 106 of the biological sterilization indicator 100, as described in greater detail below.

As shown in FIG. 5, in some embodiments, the main PCBA 45 can include three microcontrollers: a main microcontroller 60, an optics microcontroller 62, and a display microcontroller 64. The three microcontrollers 60, 62 and 64 can collectively be referred to as the "controller" 51 of the reading apparatus 12.

The controller 51, shown schematically in FIGS. 3 and 4, can be configured to control the various processing and executing portions of the reading apparatus 12. Generally, the controller 51 (or microcontrollers 60, 62 and 64) can be a suitable electronic device, such as, for example, a programmable logic controller ("PLC"), a microprocessor, a personal computer ("PC"), another industrial/personal computing device, or combinations thereof. As such, the controller 51 may include both hardware and software components, and is meant to broadly encompass the combination of such components. The controller 51 is only shown schematically in FIGS. 3 and 4, but one of ordinary skill in the art will understand the various ways in which components of the reading apparatus 12 can interact with the controller 51, for example, via wired or wireless communication. The breakdown of the controller 51 shown in FIG. 5 is shown by way of example only.

The main microcontroller 60 can control an excitation driver circuit 66 for driving excitation sources, such as LEDs, in conjunction with the LED PCBA 47. The excitation driver circuit 66 can include a ten-channel constant current driver in which each channel is controlled individually, and can connect to an array of LEDs (e.g., UV LEDs) on the LED PCBA 47. Each channel of the ten-channel current driver can be calibrated/normalized to accommodate variations from channel to channel. The main microcontroller 60 can also detect insertion and/or activation of biological sterilization indicators 100 by controlling BSI detection circuits 73 (e.g., which can include ten circuits in embodiments employing ten wells 14), in conjunction with the BSI detector PCBA 49. The BSI detection circuits 73 can each include a sensor, such as a proximity sensor (e.g., the first sensors 52, described in greater detail below with reference to FIGS. 3 and 4), that can allow the main microcontroller 60 to monitor the insertion or removal of biological sterilization indicators 100 relative to a corresponding well 14, as well as the detection of activation of the biological sterilization indicators 100. The main microcontroller 60 can also obtain emission readouts from the optics microcontroller 62; control the display microcontroller 64, and communicate with a host computer 68 via an Ethernet communication 69.

The optics microcontroller 62 can provide control of detection circuits 75 (e.g., which can include ten circuits in embodiments employing ten wells 14). Such detection circuits 75 can each include a detector, such as a photodiode, (e.g., a detector 74 of a second sensor 54, as described in greater detail below, with reference to FIGS. 3 and 4). The optics microcontroller 62 can also provide control of the temperature of the incubation block 21 via a heater control 76. The heater control 76 can include a closed-loop system that monitors the temperature of the incubator block 21 and turns the incubator block 21 on and off accordingly.

Furthermore, in some embodiments, the reading apparatus 12 (e.g., the optics microcontroller 62) can be adapted to minimize the effects of temperature variation on various electronic components of the reading apparatus 12, such as the detection circuits 75 (e.g., for fluorescence detection). That is, in some embodiments, temperature variations of various optical components can be determined and eliminated. In such embodiments, the temperature of various optical components and/or ambient temperature can be monitored, a correction factor can be determined, and the correction factor can be used to normalize the output from such optical components (e.g., the detectors 74 of the detection circuits 75). Such adjustments can minimize fluctuations in output that may be the result of temperature variation, and can improve the accuracy of the assay results of the reading apparatus 12 (e.g., regarding sterilization efficacy).

The display microcontroller 64 can receive information from the main microcontroller 60, can generate character sets, and can display information and/or capture information from the display and/or user interface 16. The display 16 can display status information and can provide error codes to a user.

As further shown in FIGS. 3 and 4, the reading apparatus 12 can include a dedicated detection system 55 associated with each of the wells 14 of the reading apparatus 12. In some embodiments, a detection system 55 can be associated with (e.g., receive signals from, deliver electromagnetic radiation to, and/or generally interact with) more than one well 14 of the reading apparatus 12; however, particular benefits have been observed when each well 14 of the reading apparatus 12 is associated with an independent and dedicated detection system 55. The dedicated detection system 55 can include all or a portion of the BSI detection circuits 73, the excitation driver circuit 66, and/or the detection circuits 75.

In FIGS. 3 and 4, one well 14, one biological sterilization indicator 100 and one detection system 55 are shown in cross-section. As shown, in some embodiments, the detection system 55 can include a first sensor 52 positioned to be aligned with the signal-modulating feature 153 of the first portion 104, and a second sensor 54. The first sensor 52 can be calibrated by zeroing out ambient light. In some embodiments, the first sensor 52 can be positioned to detect the presence of the biological sterilization indicator 100 in the well 14, as well as the position of the second portion 106 of the biological sterilization indicator 100 (e.g., to confirm activation of the biological sterilization indicator 100). In some embodiments, the second sensor 54 can be used to confirm that the biological sterilization indicator 100 has been properly positioned (e.g., fully seated) within the well 14 (e.g., to reliably confirm activation), and/or to perform the detection or assaying process by interrogating the lower portion 114 (or the second chamber 111, or a portion thereof) of the housing 102 for spore growth, for example, for a detectable change in the spores 115 or in the liquid surrounding the spores 115. In some embodiments, the first sensor 52 alone is used to confirm activation of the biological sterilization indicator 100.

At least partly because of the design of the biological sterilization indicator 100, the well 14 of the reading apparatus 12, and the second sensor 54, the entire lower portion 114 of the biological sterilization indicator 100 can be interrogated by the second sensor 54, which can result in a faster positive (e.g., spore viability and sterilization cycle failure) result than existing systems. Each well 14 can be independently interrogated by its own corresponding dedicated detection system 55 (e.g., an optical detection system). In some embodiments, the reading apparatus 12 can include one or more baffles positioned to inhibit cross-talk between the wells 14.

In some embodiments, the reading apparatus 12 can include a plurality of parts or elements that can be coupled together to define at least a portion of the well(s) 14 and/or to house the detection systems 55 (e.g., including the first sensors 52, the excitation sources 72 and the detectors 74). As shown in FIGS. 3 and 4 by way of example only, the reading apparatus 12 can include a first frame element 80 dimensioned to receive the incubator block(s) 21, and a second frame element 82 dimensioned to receive the excitation source(s) 72 and the detector(s) 74. As shown in FIGS. 3, 4, 11 and 12, the first and second frame elements 80 and 82 can be configured to be coupled together or to have mating, inter-engaging, or cooperating parts. In addition, in some embodiments, the reading apparatus 12 can further include a third frame element 84, which can couple to at least one of the first and second frame elements 80 and 82, and particularly, which can form a cover for the second frame element 82.

Figure 11:
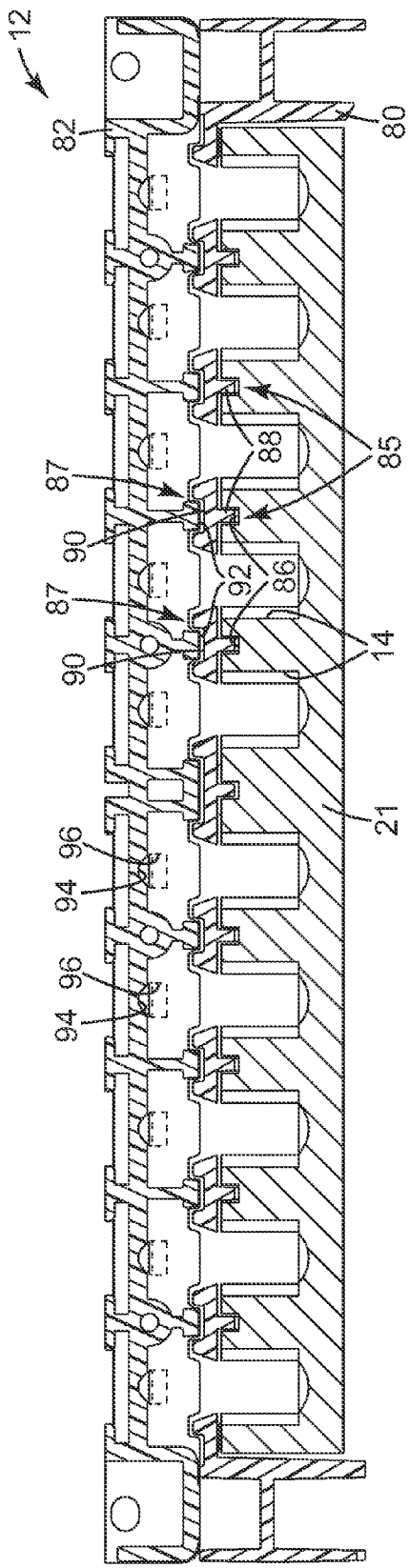
FIG. 11 is a top cross-sectional view of a portion of the reading apparatus of FIGS. 1-5, taken along the line 11-11 shown in FIG. 3, with portions removed for clarity, and with objects beyond the plane defined by the line 11-11 removed for clarity.
Figure 12:
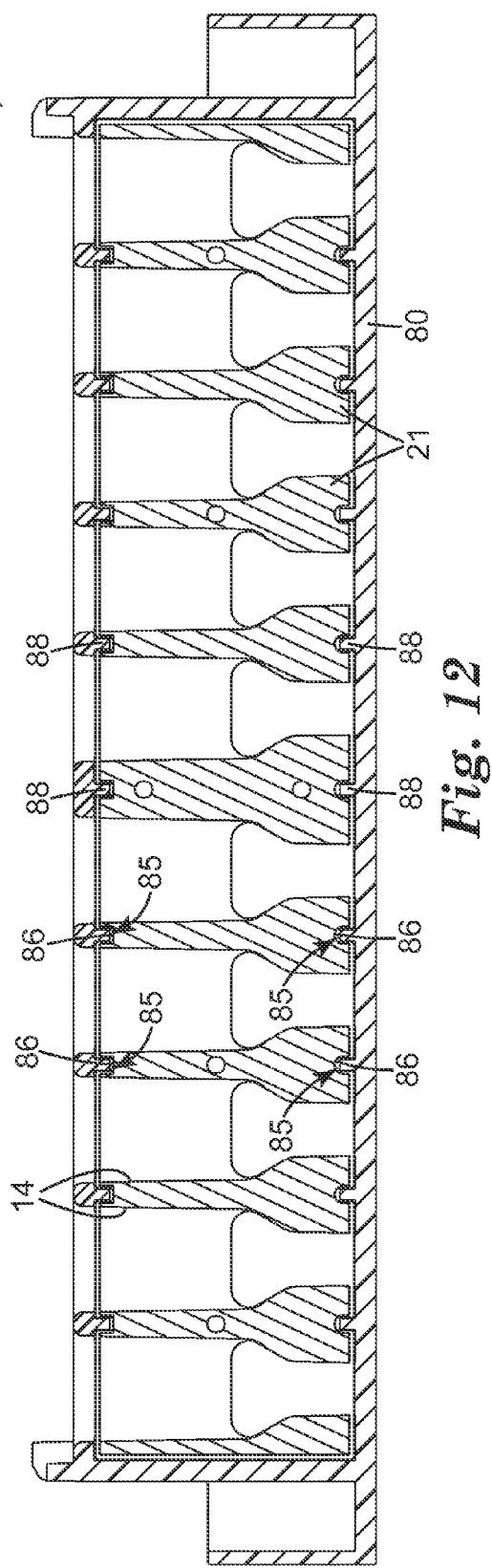
FIG. 12 is a front cross-sectional view of a portion of the reading apparatus of FIGS. 1-5, taken along the line 12-12 shown FIG. 1, with portions removed for clarity, and with objects beyond the plane defined by the line 12-12 removed for clarity.

As shown in FIGS. 11 and 12, which show a horizontal and vertical cross-section planes through the reading apparatus 12 (with the biological sterilization indicator 100 not shown for clarity), in some embodiments, one or more of the incubator block 21, the first frame element 80, the second frame element 82, and the third frame element 84 can include one or more protrusions, recesses, or ribs that are configured to interact with a mating part of an adjacent component (e.g., with one or more of the incubator 21 and the frame elements 80, 82 and 84) to form one or more baffles that are positioned between adjacent wells 14 in order to inhibit cross-talk of electromagnetic radiation (e.g., visible and/or ultraviolet light) between the wells 14.

With reference to FIGS. 11 and 12, in some embodiments, the incubator block 21 can include a plurality of channels 86 that extend along an upper surface, a bottom surface, and a side surface of the incubator block 21. In addition, the first frame element 80 can include a plurality of protrusions or ribs 88, each of which is dimensioned to be received in a channel 86 of the incubator block 21. While the channel(s) 86 and corresponding rib(s) 88 are shown in the illustrated embodiment as extending continuously along three sides or edges of the incubator block(s) 21 and the first frame element 80, it should be understood that in some embodiments, only one or more discrete channels(s) 86 and ribs(s) 88 may be necessary, which may be located on one or more sides or edges of the incubator block(s) 21 and/or the first frame element 80.

With continued reference to FIG. 11, in some embodiments, the first frame element 80 can further include a plurality of channels 90 that are formed in a rear surface. The second frame element 82 can include a plurality of protrusions or ribs 92, each of which is dimensioned to be received in a channel 90 of the first frame element 80. Similar additional coupling between the second frame element 82 and the third frame element 84 can also be present. In addition, as shown in FIG. 11, in some embodiments, the first frame element 80 and the incubator block 21 can at least partially define a plurality of wells 14, and the second frame element 82 can include one or more recesses aligned with a well 14 that are configured to house an excitation source 72 and/or a detector 74 dedicated to the adjacent well 14. For example, as shown in FIG. 11, in some embodiments, the second frame element 82 can include a plurality of first recesses 94, each of which is adapted to house at least a portion of an excitation source 72, and a plurality of second recesses 96, each of which is adapted to house at least a portion of a detector 74.

Such coupling of the incubator block 21, the first frame element 80, and the second frame element 82 allows for the three components to be coupled together to at least partially define the wells 14, to at least partially house the excitation sources 72 and the detectors 74 in line with the wells 14, and to define a first series or plurality of baffles 85 (e.g., defined by one or both of the channels 86 and the ribs 88; see FIGS. 11 and 12) and a second series or plurality of baffles 87 (e.g., defined by one or both of the channels 90 and the ribs 92) positioned between the wells 14. Additional baffling can be employed between wells 14 with mating structures between the second frame element 82 and the third frame element 84.

The reading apparatus 12 is shown in FIGS. 3, 4, 11 and 12 as including an incubator block 21 and three frame elements 80, 82 and 84 to at least partially define the wells 14 and baffling structures between wells 14. However, it should be understood that as few as one frame element or incubator block and as many as necessary can be employed to define the wells 14 and baffling structures. In addition, the channels 86 and 90 and the ribs 88 and 92 can be used interchangeably. For example, in some embodiments, the incubator block 21 can include a plurality of ribs 86 that mate with channels 88, and so on. Any similar inter-engaging structures can be employed to create one or more baffles 85, 87 to inhibit cross-talk between the wells 14 without departing from the spirit and scope of the present disclosure. Furthermore, in some embodiments, the reading apparatus 12 can include only one series of baffles, rather than at least two (i.e., the baffles 85 and 87).

As described above, in some embodiments, sufficient closure of the second portion 106 with respect to the first portion 104 of the biological sterilization indicator (e.g., sufficient cap closure) can be indicative of a successful activation step. In such embodiments, the reading apparatus 12 can include means for detecting the position of the second portion 106. For example, the first sensor 52 can be positioned to detect at least one of the following: (i) when the well 14 corresponding to the first sensor 52 is empty, and output a first signal; (ii) when the biological sterilization indicator 100 is positioned in the well 14 and the second portion 106 is in the first position 148, or at least is not in the second position 150, and output a second signal; and (iii)

when the biological sterilization indicator 100 is positioned in the well 14 and the second portion 106 is in the second position 150. The controller 51 of the reading apparatus 12 can receive the first signal, the second signal, or the third signal, and execute varying actions based on which signal is received.

As mentioned above, in some embodiments, the second position 150 of the second portion 106 can be any position in which the seal 156, or a portion thereof, engages a portion (e.g., the upper end 157) of the first portion 104 of the housing 102. As a result, the reading apparatus 12 (e.g., the controller 51) can include a threshold value that the third signal would need to reach in order to register the second portion 106 as being in a "second position," for example, in which the seal 156 is engaged and the interior of the biological sterilization indicator 100 is sealed from ambience. Such a threshold can accommodate different levels or degrees of closure of the second portion 106. For example, in some embodiments, even when only an edge (e.g., a lower edge) of the second portion 106 is in line with the first sensor 52, or "visible" to the first sensor 52, the threshold can be met, the first sensor 52 can send the third signal to the controller 51, and sufficient activation and sealing of the biological sterilization indicator 100 can be confirmed. This could be the case, for example, when the seal 156 is sized (e.g., has a sufficient length in the longitudinal direction $D_L$ of the biological sterilization indicator 100) and the threshold value is controlled such that when the threshold is met, the seal 156 is engaged. On the other hand, in embodiments in which the seal 156 is not sufficiently engaged when only an edge of the second portion 106 is in line with the first sensor 52, the threshold value can be adjusted such that the third signal would not be sent to the controller 51 until the second portion 106 is moved further onto the first portion 104 to generate a signal that meets or exceeds the threshold value.

In some embodiments, additionally or alternatively to detecting the position of the second portion 106, activation of the biological sterilization indicator 100 can be confirmed by confirming that the liquid 122 has moved into the second chamber 111, which will be described in greater detail below. As described below, in some embodiments, the second sensor 54 can be used to detect whether the liquid 122 is present in the second chamber 111.

If the controller 51 receives the first signal from the first sensor 52, the controller 51 can output to the display 16 an error code or some level of output to indicate to an operator that the well 14 is empty. Similarly, if the controller 51 receives the second signal from the first sensor 52, the controller 51 can output to the display 16 an error code or some level of output to indicate to an operator that a biological sterilization indicator 100 is positioned in the respective well 14, but that the second portion 106 is not in the second position 150, or that the biological sterilization indicator 100 has not been activated. If the controller 51 receives the third signal from the first sensor 52, the controller 51 can begin to initiate a spore growth and/or detection process, or the assay result will be output to the display 16 without an error code.

In some embodiments, the reading apparatus 12 can detect and generate (e.g., the controller 51 can output) only the first signal (i.e., the well 14 is empty) and the third signal (i.e., the biological sterilization indicator 100 is activated). In some embodiments, however, the reading apparatus 12 can generate the first signal, the second signal, and the third signal. As a result, in some embodiments, the reading apparatus 12 can generate at least two of the first signal, the second signal, and the third signal.

As mentioned above, the biological sterilization indicator 100 can be activated while the biological sterilization indicator 100 is positioned in the well 14 of the reading apparatus 12; prior to being positioned in the well 14; and/or as the biological sterilization indicator 100 is positioned in the well 14 by depressing the second portion 106 as the biological sterilization indicator 100 becomes seated in the well 14. The biological sterilization indicator 100 can be activated manually (e.g., prior to, during or after being inserted into the well 14 of the reading apparatus 12), or by using an activation device (e.g., by positioning the biological sterilization indicator 100 into a device separate from the reading apparatus 12).

In some embodiments, whether the biological sterilization indicator 100 is activated in the well 14 or out of the well 14, the reading apparatus 12 can be configured to determine if the second portion 106 is in the second position 150, and not to initiate a spore growth and assay process until activation of the biological sterilization indicator 100 is confirmed. In some embodiments, however, the reading apparatus 12 can perform the spore growth and/or detection process, but an error code or some level of output can be given to a user to inform the user that the biological sterilization indicator 100 is not properly positioned in the well 14, the biological sterilization indicator 100 has not been activated, that the spore growth and/or detection process could not be completed, that the spore growth and/or detection process could not be initiated, that the assay result may be questionable, or the like, or a combination thereof. Such error codes or outputs from the reading apparatus 12 can be displayed in the display 16 of the reading apparatus 12.

In some embodiments, the detection process (e.g., which can be controlled by the optics microcontroller 62 and can include operation of the detection circuits 75) for verifying the efficacy of a sterilization process can employ fluorescence detection in order to interrogate the second chamber 111, or a portion thereof. For example, as shown in FIGS. 3 and 4, in some embodiments, the second sensor 54 can be adapted for fluorescence detection and can include at least one emitter or excitation source (e.g., a light-emitting diode (LED)) 72 configured and positioned to emit electromagnetic radiation at a specific frequency or range of frequencies, and a detector (e.g., an emissions detector, such as a photodiode) 74 configured and positioned to detect certain frequencies of electromagnetic radiation emitted from the second chamber 111, or a portion thereof. The acute angle between the excitation source 72 and the detector 74 is shown by way of example only; however, it should be understood that other configurations are possible, including, but not limited to, a right angle, an obtuse angle, a through-path (e.g., 180 degrees) configuration, etc., or combinations thereof. Various filters known to those of ordinary skill in the art can be employed to achieve the desired frequency emission and/or detection. The excitation source 72 can excite various fluorescent molecules with a first frequency of electromagnetic radiation which can cause the fluorescent molecules to fluoresce and emit electromagnetic radiation at a second frequency, which can then be detected by the detector 74 of the second sensor 54. Other details of fluorescence detection generally known to those of ordinary skill in the art can be employed.

As mentioned above, in some embodiments, at least a portion of the second sensor 54 can be used to confirm that the biological sterilization indicator 100 has been properly positioned (e.g., fully seated) within the well 14. That is, in some embodiments, as shown in FIGS. 3 and 4, the first sensor 52 can be positioned toward the top of the well 14 and adjacent a location on the biological sterilization indicator 100 where the second portion 106 will reside when in the second position 150. In such embodiments, the first sensor 52 can detect whether an upper portion (or region) 15 of the well 14 is empty, but when the upper portion 15 is not empty, the first sensor 52 may not be able to confirm that a lower portion (or region) 17 of the well 14 is not empty. That is, as mentioned above, in some embodiments, the biological sterilization indicator 100 and the well 14 can be "keyed" with respect to one another, such that the biological sterilization indicator 100 can be positioned in the well 14 in only one orientation. If the biological sterilization indicator 100 is positioned in the well 14 at an incorrect orientation (e.g, incorrectly turned around about the longitudinal direction $D_L$), the first sensor 52 may detect that the upper portion 15 of well 14 is not empty, but the biological sterilization indicator 100 may not be fully seated within the well 14. In such embodiments, the first sensor 52 may not be properly aligned with and able to detect any signal-modulating features 153 either of the first portion 104 or the second portion 106. In such cases, at least a portion of the second sensor 54 can be used to confirm that the biological sterilization indicator 100 is positioned in the lower portion 17 of the well 14. As shown in FIGS. 3 and 4, the second sensor 54 can be positioned toward the bottom of the well 14 (i.e., adjacent the lower portion 17 of the well 14) and can be positioned to detect whether the lower portion 17 of the well 14 is empty.

Additionally or alternatively, as mentioned above, the second sensor 54 can be used to detect whether liquid is present in the second chamber 111, thereby confirming that the container 120 has been fractured and that the liquid 122 has been moved into the portion of the biological sterilization indicator 100 that contains the spores 115. In some embodiments, the second sensor 54 can be configured to detect at least one of the following: whether the biological sterilization indicator 100 is positioned in the well 14 (or at least in a portion of the well 14 adjacent the second sensor 54, such as the lower portion 17 of the well 14), and whether the liquid 122 is present in the second chamber 111 of the biological sterilization indicator 100, or in the portion of the biological sterilization indicator 100 that is adjacent the second sensor 54.

For example, in some embodiments, the second sensor 54 can be configured to generate at least one of the following: (i) a first signal when the well 14 (or at least the portion of the well 14 that is adjacent the second sensor 54, such as the lower portion 17) is empty, (ii) a second signal when the biological sterilization indicator 100 is positioned in a portion (e.g., the lower portion 17) of the well 14 and no liquid is present in the biological sterilization indicator 100 (e.g., in the second chamber 111 of the biological sterilization indicator 100), and (iii) a third signal when the biological sterilization indicator 100 is positioned in a portion (e.g., the lower portion 17) of the well 14 and the liquid 122 is present in the biological sterilization indicator 100 (e.g., in the second chamber 111 of the biological sterilization indicator 100).

As a result, in some embodiments, the reading apparatus 12 can be configured to confirm activation of the biological sterilization indicator 100 by generating one or more signals that can indicate that the second portion 106 of the housing 102 is in the second position 150 and/or that the liquid 122 is present in the second chamber 111. That is, in some embodiments, the reading apparatus 12 can generate a signal that is indicative of at least one of (i) the biological sterilization indicator 100 being positioned in the well 14 with the second portion 106 of the housing 102 in the second position 150, and (ii) the biological sterilization indicator 100 being positioned in the well 14 with the liquid 120 being present in the second chamber 111. Said another way, in some embodiments, the reading apparatus 12 can be configured to confirm activation of the biological sterilization indicator 100 by generating (i) a first signal when the second portion 106 of the housing 102 is in the second position 150, and/or (ii) a second signal when the liquid 122 is present in the second chamber 111.

Detection of the liquid 122 in the second chamber 111 can be performed by detecting an optical property of the liquid 122, including but not limited to, electromagnetic radiation (e.g., in the ultraviolet, visible, and/or infrared bands), fluorescence, luminescence, light scattering, turbidity, absorption, Raman spectroscopy, ellipsometry, color, opacity/translucency/transparency, refractive index, optical density, or the like, or a combination thereof. Detection of such characteristics can be carried out by a reading apparatus 12 (or second sensor 54) that employs one or more of an excitation source (e.g., the excitation source 72) and detector (e.g., the detector 74), a fluorimeter, a spectrophotometer, colorimeter, or the like, or combinations thereof. In some embodiments, such as embodiments that measure fluorescence, visible light, etc., the detectable change can be measured by detecting at a particular wavelength.

For example, in some embodiments, the presence of the liquid 122 in the biological sterilization indicator 100 (e.g., in the first portion 104 of the biological sterilization indicator 100) can alter the refractive index of the biological sterilization indicator 100, and the change in refractive index can be detected. The refractive index can either be compared to a predetermined threshold value, or to a previously obtained value either from the empty well 14 (i.e., if a measurement is taken before the biological sterilization indicator 100 is positioned in the well 14) or from the unactivated biological sterilization indicator 100 (i.e., if a measurement is taken before the biological sterilization indicator 100 is activated, e.g., before the second portion 106 is moved to the second position 150).

By way of further example, in some embodiments, the liquid 122, or a component thereof (e.g., an indicator reagent, such as a PH indicator, such as bromocresol purple (BCP)), can be detected optically by measuring, for example, fluorescence or optical density, in which the fluorescence or optical density of the liquid 122 (or a component thereof) is different from an observed "background" fluorescence or optical density when no liquid 122 is present (e.g., in the second chamber 111). The fluorescence or optical density can either be compared to a predetermined threshold value, or to a previously obtained value either from the empty well 14 (i.e., if a measurement is taken before the biological sterilization indicator 100 is positioned in the well 14) or from the unactivated biological sterilization indicator 100 (i.e., if a measurement is taken before the biological sterilization indicator 100 is activated, e.g., before the second portion 106 is moved to the second position 150).

In addition, in some embodiments, the presence of the liquid 122 can alter an optical property of the biological sterilization indicator 100, and the change in optical property of the biological sterilization indicator 100 can be detected. Again, the change in optical property can be compared to a predetermined threshold value, or to a previously obtained value, either from the empty well 14, or from the unactivated biological sterilization indicator 100.

The optical property detected can be any of those mentioned above, such as opacity/translucency/transparency, light scattering, etc., or combinations thereof. For example, in some embodiments, the biological sterilization indicator 100 can include an inner surface, inner wall, or other element or component located in or adjacent the second chamber 111, the spores 115 (or spore carrier 135), and/or another location where detection optics may come into play. Such a wall, surface or element can be etched (e.g., chemically etched, such as by plasma treatment) or otherwise surface-modified, such that the element scatters light when it is dry (i.e., when the liquid 122 is not present in the second chamber 111), but does not scatter light when it is wetted out (i.e., when the liquid 122 is present in the second chamber 111). In some embodiments, one or more of the planar walls 168 (e.g., the detection window 167), or a portion thereof, can include an inner surface that has been etched or otherwise surface-modified to scatter light when dry, but not when wet. In some embodiments, the spore carrier 135, or a portion thereof, can be the modified component. In some embodiments, the biological sterilization indicator 100 can include an additional element or component (e.g., a thin wall) as the modified component that can be provided in the second chamber 111, for example, between the spores 115 and the detection window 167. In some embodiments, such an additional component can be inserted into the second chamber 111, can be integrally formed with the housing 102, or a combination thereof. In some embodiments, any combination of the above configurations can be employed, such that one or more of a planar wall 168, the spore carrier 135, and an additional element or component can be surface-modified to optically distinguish between when such an element is dry and the liquid 122 is not present in the second chamber 111, and when such an element is wet and the liquid 122 is present in the second chamber 111.

In some embodiments, the second sensor 54 can be used both to serve as a backup for the first sensor 52 to confirm that the biological sterilization indicator 100 has been correctly positioned and oriented with respect to the well 14, and to confirm that the biological sterilization indicator 100 has been activated by confirming the presence of the liquid 122 in the second chamber 111. As a result, in some embodiments, the first sensor 52 can be used to detect whether the second portion 106 is in the second "activated" position 150, the second sensor 54 can be used to confirm that the biological sterilization indicator 100 is not improperly oriented in the well 14 (or is fully seated in the well 14), and/or the second sensor 54 can be used to confirm the presence of the liquid 122 in the second chamber 111.

While some embodiments can employ the first sensor 52 and the second sensor 54 to perform all of the above functions, in some embodiments, the reading apparatus 12 can simply detect when the well 14 is empty and when the biological sterilization indicator 100 has been activated. Detection of an empty well 14 can be performed by one or both of the first sensor 52 and the second sensor 54, and both the first sensor 52 and the second sensor 54 need not be employed in all embodiments. In addition, detection or confirmation of activation of the biological sterilization indicator 100 can be performed by one or both of the first sensor 52 and the second sensor 54. That is, in some embodiments, the first sensor 52 is used to detect the position of the second portion 106 of the housing 102 to determine whether the biological sterilization indicator 100 has been activated, and the second sensor 54 is used in addition to the first sensor 52 to confirm that the biological sterilization indicator 100 is properly positioned and oriented in the well 14. In some embodiments, the second sensor 54 is also used to confirm the presence of the liquid 122 in the second chamber 111. In some embodiments, the first sensor 52 is used alone (i.e., without the second sensor 54) to detect the position of the second portion 106 of the housing 102, and this information alone is used to confirm activation of the biological sterilization indicator 100. In some embodiments, the second sensor 54 is used alone (i.e., without the first sensor 52) to detect one or more of the presence of the biological sterilization indicator 100 in the well 14 and/or the presence of the liquid 122 in the second chamber 111.

That is, in some embodiments, the reading apparatus 12 (e.g., the second sensor 54) can be configured to generate at least one of (i) a first signal when the biological sterilization indicator 100 is positioned in the well 14 and the liquid is not present in the second chamber 111; and (ii) a second signal when the biological sterilization indicator 100 is positioned in the well 14 and the liquid is present in the second chamber 111. In such embodiments, the reading apparatus (e.g., the second sensor 54) can be configured to additionally generate a signal (e.g., a third signal) indicative of the well 14 being empty. Furthermore, in such embodiments, the biological sterilization indicator 100 need not include the above-described first portion 104 and second portion 106 of the housing 102, and the movement of the second portion 106 need not be detected by any first sensor 52. Rather, all three signals can be generated by a single sensor, or by multiple sensors positioned adjacent the lower portion 17 of the well 14.

In such embodiments, if the controller 51 receives the first signal from the second sensor 54, the controller 51 can output to the display 16 an error code or some level of output to indicate to an operator that the well 14 is empty. Similarly, if the controller 51 receives the second signal from the second sensor 54, the controller 51 can output to the display 16 an error code or some level of output to indicate to an operator that a biological sterilization indicator 100 is positioned in the respective well 14, but that the liquid 122 is not present in the second chamber 111, or that the biological sterilization indicator 100 has not been activated. If the controller 51 receives the third signal from the second sensor 54, the controller 51 can begin to initiate a spore growth and/or detection process, or the assay result will be output to the display 16 without an error code.

In some embodiments, the reading apparatus 12 can detect and generate (e.g., the controller 51 can output) only the first signal (i.e., the well 14 is empty) and the second signal (i.e., the biological sterilization indicator 100 is activated). In some embodiments, however, the reading apparatus 12 can generate the first signal, the second signal, and the third signal. As a result, in some embodiments, the reading apparatus 12 can generate at least two of the first signal, the second signal, and the third signal.

In embodiments employing both the first sensor 52 and the second sensor 54, first sensor 52 can be positioned to detect at least one of the following: (i) when the well 14 corresponding to the first sensor 52 is empty, and output a first signal; (ii) when the biological sterilization indicator 100 is positioned in the well 14 and the second portion 106 is in the first position 148, or at least is not in the second position 150, and output a second signal; and (iii) when the biological sterilization indicator 100 is positioned in the well 14 and the second portion 106 is in the second position 150. The controller 51 of the reading apparatus 12 can receive the first signal, the second signal, and/or the third signal, and execute varying actions based on which signal or signals are received. In addition, in such embodiments, the second sensor 54 can be positioned to detect at least one of the following: (i) when the well 14 corresponding to the second sensor 54 is empty, and output a fourth signal; (ii) when the biological sterilization indicator 100 is positioned in the well 14 and/or when the liquid 122 is not present in the second chamber 111, and output a fifth signal; and (iii) when the biological sterilization indicator 100 is positioned in the well 14 and the liquid 122 is present in the second chamber 111, and output a sixth signal. The controller 51 of the reading apparatus 12 can receive the fourth signal, the fifth signal, and/or the sixth signal, and execute varying actions based on which signal or signals are received.

In some embodiments, as shown in FIGS. 3 and 4, the well 14 can be elongated and can include a longitudinal direction. The longitudinal direction $D_L$ of the biological sterilization indicator 100 can be oriented substantially along (or substantially aligned with) the longitudinal direction of the well 14 when the biological sterilization indicator 100 is positioned in the well 14. In such embodiments, the upper portion 15 of the well 14 can be a first longitudinal portion or region 15, and the lower portion 17 of the well 14 can be a second longitudinal portion or region 17 that is spaced a longitudinal distance from the first longitudinal portion or region 15.

In such embodiments, as mentioned above, the second sensor 54 can be configured to generate a fourth signal indicative of the lower portion 17 of the well 14 being empty, and a fifth signal indicative of the lower portion 17 of the well 14 not being empty. In some embodiments, the second sensor 54 can be configured to generate a sixth signal indicative of the liquid 122 being present in the lower portion 114 of the biological sterilization indicator 100.

In some embodiments, the second sensor 54 can be configured to generate a sixth signal (or a seventh signal, if the liquid detection function is employed) indicative of spore viability (i.e., sterilization cycle failure) and a seventh signal (or an eighth signal, if the liquid detection function is employed) indicative of spore death (i.e., sterilization cycle success).

In embodiments employing the second sensor 54 to additionally confirm proper positioning of the biological sterilization indicator 100 in the well 14 in order to rely on the signal from the first sensor 52 to confirm activation, in some embodiments, the reading apparatus 12 can initiate a spore growth procedure (or simply not report error codes when the assay results are displayed) when the controller 51 receives the third signal from the first sensor 52 and the fifth signal from the second sensor 54. On the other hand, the reading apparatus 12 can either prevent an assay process from initiating, or report error codes when the assay results are displayed, when the controller 51 receives the first signal or the second signal from the first sensor 52 and the fourth signal from the second sensor 54. The first sensor 52 signals are referred to as the "the first signal," "the second signal," and "the third signal," and the second sensor 54 signals are referred to as "the fourth signal" and "the fifth signal," etc. for clarity purposes only; however, it should be understood that all signal references are for clarity and simplicity only, and other signal references can be used to describe the outputs generated by the first and second sensors 52 and 54 without departing from the spirit and scope of the present disclosure.

As described above, the second sensor 54 can include an excitation source 72 and a detector 74 that can be employed for fluorescence detection, for example, when assaying the biological sterilization indicator 100 for spore viability. In some embodiments, the same excitation source 72 and detector 74 can be used to generate the fourth and/or fifth signals for the purposes of confirming the position of the biological sterilization indicator 100 in the well 14, and/or of confirming activation of the biological sterilization indicator 100. While this configuration of the second sensor 54 is shown and described, it should be appreciated to those of ordinary skill in the art that other configurations and types of sensors (e.g., any of those described below with respect to the first sensor 52) or components can be employed in the second sensor 54 for the purpose of confirming position and/or activation of the biological sterilization indicator 100.

In some embodiments, the first sensor 52 can include at least one of a photointerrupter (e.g., transmissive and/or reflective), a capacitive sensor, another suitable proximity sensor, or a combination thereof. Photointerrupters can detect an object that interrupts a light beam between a sensor and a reflector (i.e., reflective) or between an emitter and a receiver (i.e., transmissive). As a result, in some embodiments, the first sensor 52 can include an excitation source and detector, similar to that described above with respect to the second sensor 54. However, in some embodiments, the excitation source and detector of the first sensor 52 can be located near one another, for example, in the same housing. For example, in embodiments employing a reflective photointerrupter, the first sensor 52 can detect the position of the second portion 106 by emitting electromagnetic radiation into an adjacent portion of the well 14, and sensing the reflected signal. In some embodiments, the first portion 104 and/or the second portion 106 can include one or more signal-modulating features that could modify the signal emitted by the first sensor 52, such that the modulation of the reflected signal would be detected by the first sensor 52. A variety of signal-modulating features can be employed with the first portion 104, the second portion 106, and/or another component of the biological sterilization indicator 100. In the embodiment shown in FIGS. 3 and 4, the first portion 104 can include a signal-modulating feature 153 that can be used to alter the signal received by the first sensor 52 when the electromagnetic radiation is reflected back to the first sensor 52.

By way of example only, the signal-modulating feature 153 is shown in the embodiment of FIGS. 1-4 as being or including the flat-to-round transition, or step, 152. In some embodiments, particularly in those employing reflective sensors, if the first sensor 52 emits a signal into an empty well 14, the signal that is reflected back to the first sensor 52 will be low, relative to other received (e.g., reflected) signals. Furthermore, if the first sensor 52 emits a signal onto a smooth portion (e.g., a smooth flat surface or a smooth rounded surface) of the first portion 104 or the second portion 106, the received (e.g., reflected) signal will be high, relative to other signals. On the other hand, if the first sensor 52 detects the flat-to-round transition 152, the reflected signal received by the first sensor 52 will be intermediate that of the relatively low signal and the relatively high signal, such that substantially and significantly different signals will be received by the first sensor 52, and will be indicative of different scenarios.

With reference to the embodiment of FIGS. 3 and 4, if the well 14 is empty, the first sensor 52 will receive a low signal and will send the first signal to the controller 51. If the biological sterilization indicator 100 is positioned in the well 14 but the second portion 106 is not in the second position 150, as shown in FIG. 3, the first sensor 52 will receive an intermediate signal because at least a portion of the signal emitted by the first sensor 52 will be deflected by the exposed signal-modulating feature 153 (i.e., the flat-to-round transition 152) of the first portion 104. The first sensor 52 will then send the second signal to the controller 51. However, if the second portion 106 has been moved to the second position 150 (or when the second portion 106 is moved to the second position 150), as shown in FIG. 4, the first sensor 52 will receive a high signal because the second portion 106 will have moved a sufficient amount to cover or obscure the signal-modulating feature 153 of the first portion 104 from being detected by the first sensor 52. When the signal-modulating feature 153 is obscured by the second portion 106 and no longer exposed to or aligned with the first sensor 52, the signal from the first sensor 52 is not deflected by the signal-modulating feature 153. Rather, the first sensor 52 would receive a relatively high signal from the smooth outer surface of the second portion 106 when the second portion 106 is in the second position 150. In such embodiments, the reading apparatus 12 can be configured such that the relatively high signal results in the first sensor 52 sending the third signal to the controller 51, because the biological sterilization indicator 100 is positioned in the well 14 and the second portion 106 has been moved to the second position 150.

That is, in the embodiment illustrated in FIGS. 1-4, the first portion 104 of the biological sterilization indicator 100 includes a signal-modulating feature 153 that can be exposed to, accessible by, readable by and/or detectable by the reading apparatus 12 when the second portion 106 is in the first position 148 (or not in the second position 150) but not when the second portion 106 is in the second position 150 (i.e., the second portion 106 obscures the signal-modulating feature 153 when in its second position 150). As a result, in the embodiment of FIGS. 1-4, the first sensor 52 can generate: a first signal when the well 14 is empty; a second signal that is significantly different from the first signal, based on the exposed signal-modulating feature 153 of the first portion 104, when the biological sterilization indicator 100 is positioned in the well 14 and the second portion 106 of the biological sterilization indicator 100 is not in the second position 150, e.g., is in the first position 148 (see FIG. 3); and a third signal that is significantly different from the first signal and the second signal, when the biological sterilization indicator 100 is positioned in the well 14, the second portion 106 is in the second position 150, and the signal-modulating feature 153 is no longer exposed (see FIG. 4).

Figure 6:
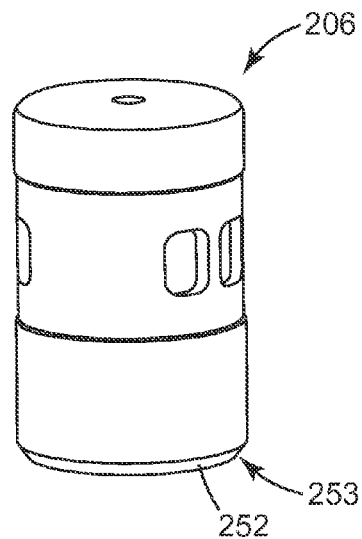
FIG. 6 is a perspective view of a second portion of the housing of the biological sterilization indicator according to another embodiment of the present disclosure.

Additionally, or alternatively, in some embodiments, the second portion 106 can include a signal-modulating feature. FIG. 6 illustrates a second portion 206 of the housing of a biological sterilization indicator according to another embodiment of the present disclosure. As shown in FIG. 6, the second portion 206 can be similar to the second portion 106 of FIGS. 2-4, except that the second portion 206 can include a signal-modulating feature 253. By way of example, the signal-modulating feature 253 includes an inwardly-extending angled surface, wall, or deflection zone 252 located adjacent the bottom edge of the second portion 206. That is, the angled surface 252 can be adapted to deflect light differently than adjacent portions of the outer surface of the second portion 206. In some embodiments, the angled surface 252 can be referred to as a recess. Such a signal-modulating feature 253 can be positioned to be sensed by the first sensor 52, for example, when the second portion 206 is in its second position.

Figure 7:
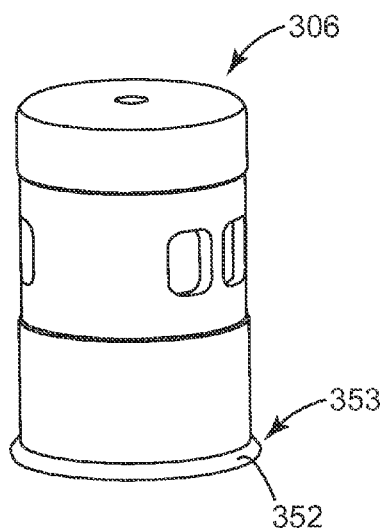
FIG. 7 is a perspective view of a second portion of the housing of the biological sterilization indicator according to another embodiment of the present disclosure.

Similarly, FIG. 7 illustrates a second portion 306 of the housing of a biological sterilization indicator according to another embodiment of the present disclosure. As shown in FIG. 7, the second portion 306 can be similar to the second portions 106 and 206, except that the second portion 306 of FIG. 7 can include a signal-modulating feature 353. By way of example, the signal-modulating feature 353 includes an outwardly-extending angled surface, wall, or deflection zone 352 located adjacent the bottom edge of the second portion 352. The angled surface 352 can be adapted to deflect light differently than adjacent portions of the outer surface of the second portion 306. In some embodiments, the angled surface 352 can be referred to as a protrusion, flange, or ledge. Again, such a signal-modulating feature 353 can be positioned to be sensed by the first sensor 52, for example, when the second portion 306 is in its second position.

Figure 8:
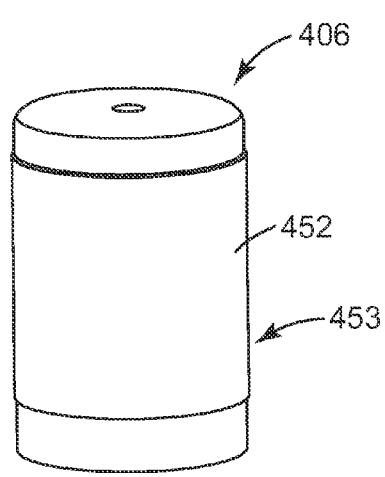
FIG. 8 is a perspective view of a second portion of the housing of the biological sterilization indicator according to another embodiment of the present disclosure.

FIG. 8 illustrates a second portion 406 of the housing of a biological sterilization indicator according to another embodiment of the present disclosure. As shown in FIG. 8, in some embodiments, the second portion 406 can include a signal-modulating feature 453. By way of example, the signal-modulating feature 453 includes a label 452 or other color or surface modification that presents a signal that is unique to the second portion 406, e.g., a uniquely high or uniquely low signal (i.e., relative to an empty well or a first portion of a biological sterilization indicator) to the first sensor 52 when the second portion 406 is in its second position. The label 452 can include a color, dye, and/or surface finish that produces the uniquely high or uniquely low signal, for example, relative to a first portion of the housing of a biological sterilization indicator. In addition, or alternatively, the label 452 can include a pattern, barcode, or other identifying feature unique to the second portion 406, such that the label 452, or a portion thereof, produces the unique signal, for example, relative to a first portion of the housing of the biological sterilization indicator. In such embodiments, a sensor (e.g., the first sensor 52 of the reading apparatus 12 of FIGS. 1-5) can be configured to align with the label 452, or a desired portion thereof, when the second portion 406 is in its second, or closed, position, such that the sensor can confirm (i.e., via the signal that is unique to the label 452) that the second portion 406 has moved a sufficient amount to cause fracturing of a container, and to cause activation (and/or sealing) of the biological sterilization indicator. In other embodiments, a first portion of the biological sterilization indicator can include such a label that provides a unique signal when the second portion 406 is in its first position but which is obscured by the second portion 406 when the second portion 406 is in its second position.

In embodiments such as those shown in FIGS. 6-8, the second portion 206, 306, 406 can include a signal-modulating feature 253, 353, 453 instead of the first portion 104 including a signal-modulating feature, and the signal-modulating feature 253, 353, 453 can be positioned on the second portion 206, 306, 406 such that the signal-modulating feature 253, 353, 453 is aligned with the first sensor 52 when the second portion 206, 306, 406 is in the second position 150. In such embodiments, the first sensor 52 can generate: a first signal when the well 14 is empty; a second signal that is significantly different from the first signal when the biological sterilization indicator 100 is positioned in the well 14 and the second portion 206, 306, 406 is not in the second position 150 (e.g., is in the first position 148); and a third signal that is significantly different from the first signal and the second signal, based on the exposed signal-modulating feature 253, 353, 453 of the second portion 206, 306, 406, when the biological sterilization indicator 100 is positioned in the well 14 and the second portion 206, 306, 406 of the biological sterilization indicator 100 is in the second position 150. In some embodiments, as described below with reference to FIG. 10, both the first portion 104 and the second portion 106 can include a signal-modulating feature, and in such embodiments, more than one first sensor 52 can be employed.

As illustrated by FIGS. 6-8, the second portion 106, 206, 306, 406 can include a variety of signal-modulating features (such as signal-modulating features 253, 353 and 453). That is, the second portion 106, 206, 306, 406 can include any of the signal-modulating features described above with respect to the signal-modulating feature 153 of the first portion 104 of FIGS. 2-4, or a combination thereof.

The reading apparatus 12 (e.g., the first sensor 52) can be configured to sense a variety of signal-modulating features of the biological sterilization indicator 100. As mentioned above, in some embodiments, the first portion 104 and/or the second portion 106 of the biological sterilization indicator 100 can include a signal-modulating feature that can be detected or sensed by the reading apparatus 12, for example, to indicate whether the biological sterilization indicator 100 has been activated. However, in some embodiments, another portion of the biological sterilization indicator 100 can include a signal-modulating feature that can generate a uniquely different second signal and third signal. For example, in some embodiments, the container 120, the insert 130, and/or another portion of the biological sterilization indicator 100 can include one or more signal-modulating features. Other examples of signal-modulating features that can be employed are described in greater detail below with reference to FIGS. 9-10.

The signal-modulating feature 153, and particularly, the flat-to-round transition 152, that is illustrated in FIGS. 2-4 is shown by way of example only; however, it should be understood that a variety of signal-modulating features 153 can be employed instead, or in addition to, the signal-modulating feature 153 shown in FIGS. 2-4. For example, in some embodiments, the signal-modulating feature 153, no matter which component(s) of the biological sterilization indicator 100 include, provide or are coupled to the signal-modulating feature 153, can include, but is not limited to, a protrusion, flange, ledge, recess, or other surface shape change or deflection region or zone, such as the flat-to-round transition 152 of FIGS. 2-4, an angled surface, such as the angled surfaces 252 and 352 of FIGS. 6 and 7, etc.; a label or color or surface change that provides either a uniquely high or uniquely low signal in reflection, such as the label 452 of FIG. 8; a surface modification, such as that shown in FIG. 9 and described below; material makeup or additive (e.g., a metal-filled resin) that provides a unique signal; another suitable signal-modulating feature; or a combination thereof. A surface modification can provide deflection, absorbance, diffraction, and/or diffusion of a signal, similar to other signal-modulating features, and can include, but is not limited to, one or more of an etched surface (e.g., formed by a chemical etching process, such as plasma etching, e.g., corona etching, or the like), an abraded surface (e.g., formed by a mechanical (e.g., an abrasion process, sandblasting, etc., or combinations thereof) or optical (e.g., laser) process), a microstructured or microreplicated surface (e.g., formed by a microreplication process), an otherwise textured surface or surface finish (e.g., formed by a molding or manufacturing process), another suitable surface modification, or a combination thereof. In some embodiments, the signal-modulating feature 153 can include an optical property (e.g., color, opacity/translucency, refractive index, etc.) that is different from adjacent regions of the biological sterilization indicator 100.

Figure 9:
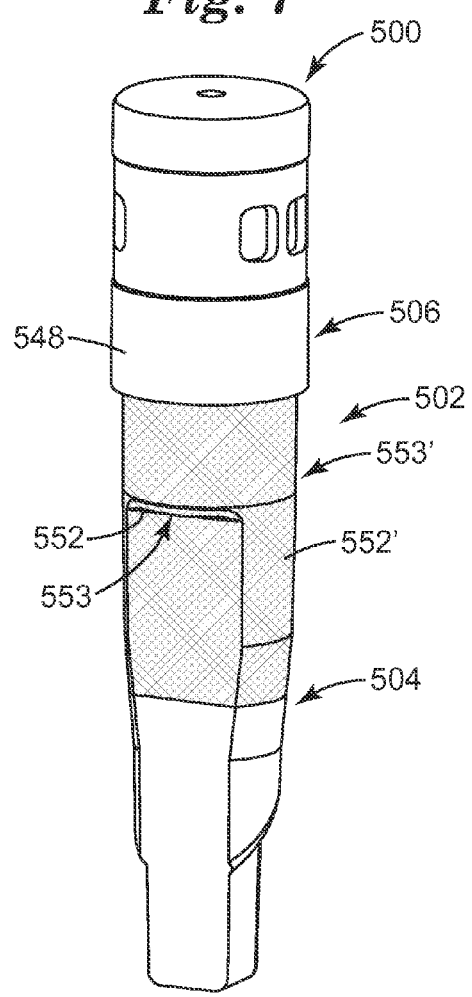
FIG. 9 is a perspective view of a biological sterilization indicator according to another embodiment of the present disclosure.

FIG. 9 illustrates a biological sterilization indicator 500 according to another embodiment of the present disclosure. Elements and features corresponding to elements and features in the illustrated embodiment of FIGS. 2-4 are provided with the same reference numerals in the 500 series. Reference is made to the description above accompanying FIGS. 2-4 for a more complete description of the features and elements (and alternatives to such features and elements) of the embodiment illustrated in FIG. 9.

The biological sterilization indicator 500 includes a housing 502 formed of a first portion 504 and a second portion 506 that are movable relative to one another, for example, to activate (and seal) the biological sterilization indicator 500 after sterilization. The biological sterilization indicator 500 is similar to the biological sterilization indicator 100 of FIGS. 2-4, except that the biological sterilization indicator 500 includes a first signal-modulating feature 553 in the form of a flat-to-round transition 552 and a second signal-modulating feature 553' in the form of a surface modification 552'. Particularly, the surface modification 552' is in the form of a textured surface, but it should be understood that a variety of other signal-modulating features, such as those mentioned above, can be employed as the second signal-modulating feature 553'. By way of example only, the textured surface of the embodiment illustrated in FIG. 9 can be formed by a texture that is called out by a molding guide, e.g., MT 11010 with a D-2 finish, such that the texture is formed during the manufacturing (e.g., molding) process used to form the housing 502, and particularly, to form the first portion 504 of the housing 502.

Such a combination or multiplication of signal-modulating features 553, 553' on the first portion 504 of the biological sterilization indicator 500 can be used, for example, to ensure that the first sensor 52 receives a signal from the first portion 504 when the second portion 506 is in its first position 548 that is significantly different from the signal received from the second portion 506 when the second portion 506 is in its second position (not shown). In addition, in some embodiments, the surface modification 552' can give a more reliable failure mode when the biological sterilization indicator 100 is incorrectly oriented in the well 14, for example, because the back of the biological sterilization indicator 100 would not give a similar signal as the smooth second portion 106. As a result, a first sensor (e.g., the first sensor 52 of the reading apparatus 12 of FIGS. 1-5) would receive a unique intermediate signal from the surface modification 552' (e.g., if the biological sterilization indicator 100 were incorrectly turned around in the well 14), and a unique high signal from the smooth second portion 106. As a result, an incorrectly oriented biological sterilization indicator 100 would not give the same signal to the first sensor as the second portion 106 in its second position, and it would be clear when the biological sterilization indicator 100 was simply incorrectly oriented in the well 14.

The surface modification 552' can also provide a means for minimizing or inhibiting ambient light from reaching a detection chamber, or region to be interrogated, of the biological sterilization indicator 500 (e.g., a second chamber, such as the second chamber 111 of FIGS. 2-4). The surface modification 552' is illustrated and described above by way of example only as being a textured surface. However, other surface modifications that include one or more of any of the above signal-modulating features can also employed to inhibit ambient light from reaching certain portions of the biological sterilization indicator 500. For example, the surface modification could additionally or alternatively include a color (e.g., a dye), a reflective surface, could be opaque, could include other suitable optical properties for inhibiting ambient light from entering the biological sterilization indicator 500, or combinations thereof.

In some embodiments, ambient light can affect assaying or detection techniques, such as fluorescence detection, that are employed to assay for growth or viability of a source of biological activity. By modifying at least a portion of a surface (e.g., an outer surface or an inner surface) of the housing 502, such ambient light can be scattered and inhibited from being transmitted along the biological sterilization indicator 500 to a region that may affect assay results. The configuration and location of the surface modification 552' is shown by way of example only, and could be employed, such that when the second portion 506 of the housing 502 is in a second or closed position, any ambient light around the biological sterilization indicator 500 would encounter the surface modification 552' on the first portion 504 of the housing 502, and be sufficiently scattered by the surface modification 552', such that the ambient light is inhibited from entering the biological sterilization indicator 500 and reaching a lower portion (e.g., the lower portion 114 of FIGS. 2-4) or detection chamber (e.g., the second chamber 111 of FIGS. 2-4) of the biological sterilization indicator 500. In some embodiments, such as the embodiment shown in FIG. 9, the surface modification 552' can be positioned on the first portion 504. In such embodiments, any ambient light entering the biological sterilization indicator 500, through any path, would be scattered by the surface modification 552'; for example, light passing through the second portion 506 (e.g., if the second portion 506 is not completely opaque); light passing through apertures in the second portion 506, such as apertures 107 of FIG. 2 (e.g., through a barrier or filter positioned over the apertures); light passing just below the second portion 206 (e.g., between the biological sterilization indicator 500 and a well of a reading apparatus that the biological sterilization indicator 500 is positioned in during detection); or combinations thereof.

Other similar surface modification means can be employed for inhibiting ambient light from reaching certain portions of the biological sterilization indicator 500 where such ambient light may interfere with assaying or detection processes. A method for testing whether ambient light is reaching certain portions of the biological sterilization indicator 500 can include turning off any excitation sources, such as the excitation source 72 of FIGS. 3-4 (e.g., LEDs) of a reading apparatus, and using a detector, such as the detector 74 of FIGS. 3-4 to see if any ambient light is being detected by the detector (e.g., if the detector registers a non-zero lighting condition) at a frequency (e.g., at 450 nm) that may correspond to and interfere with the detection process.

Figure 10:
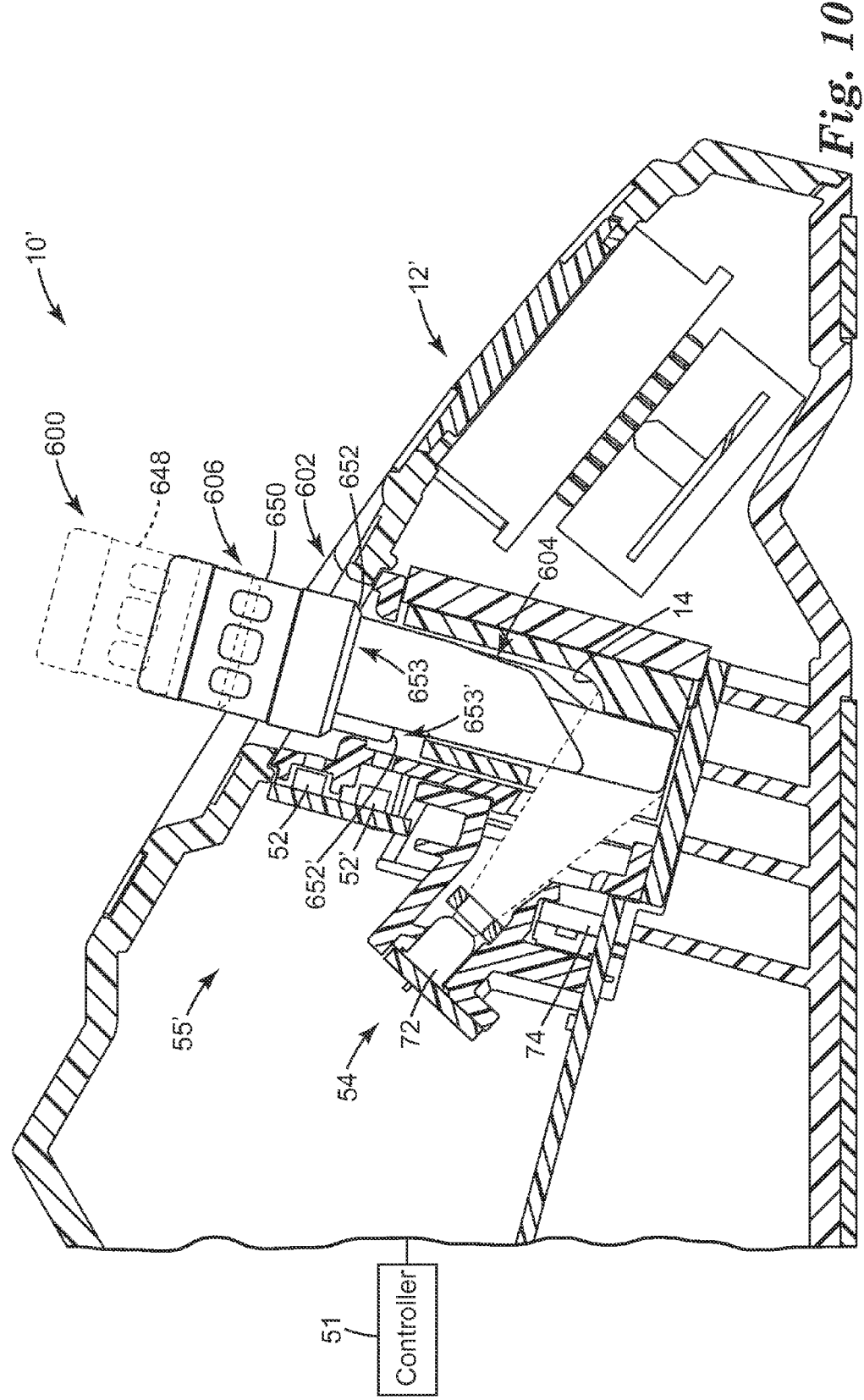
FIG. 10 is a partial cross-sectional side view of a biological sterilization indicator system according to another embodiment of the present disclosure, the biological sterilization indicator system including a biological sterilization indicator shown in a perspective view.

FIG. 10 illustrates a biological sterilization indicator system 10' according to another embodiment of the present disclosure. The biological sterilization indicator system 10' includes a reading apparatus 12' and a biological sterilization indicator 600. The reading apparatus 12' is similar to the reading apparatus 12 of FIGS. 1-4, and therefore, the reading apparatus 12' is provided with substantially the same reference numerals as the reading apparatus 12, with additional or different elements referenced with a "prime" symbol after the number. Elements and features of the biological sterilization indicator 600 corresponding to elements and features in the illustrated embodiment of FIGS. 1-4 are provided with the same reference numerals in the 600 series. Reference is made to the description above accompanying FIGS. 1-4 for a more complete description of the features and elements (and alternatives to such features and elements) of the embodiment illustrated in FIG. 10.

The biological sterilization indicator 600 includes a housing 602 formed of a first portion 604 and a second portion 606 that are movable relative to one another (e.g., to activate (and seal) the biological sterilization indicator 600 after sterilization) between a first position 648 (shown in phantom lines) and a second position 650 (shown in solid lines). As shown in FIG. 10, the second portion 606 includes a signal-modulating feature 653 in the form of an inwardly-extending surface 652 adjacent a bottom edge of the second portion 606 (similar to the second portion 206 of FIG. 6). In addition, the first portion 604 includes a signal-modulating feature 653' in the form of a flat-to-round transition 652', similar to that of the biological sterilization indicator 100 of FIGS. 2-4 described above.

The biological sterilization indicator system 10' of FIG. 10 can function similarly as the biological sterilization indicator system 10 of FIGS. 1-5, and can include similar components, except that the reading apparatus 12' includes a third sensor (or additional "first" sensor) 52'. As shown in FIG. 10, in some embodiments, the first sensor 52 can be positioned adjacent the signal-modulating feature 653 of the second portion 606 when the second portion 606 is in the second position 650, such that when the second portion 606 is in the first position 648, the smooth outer wall (i.e., not in the region of the flat-to-round transition 652') of the first portion 604 will present a uniquely high signal to the first sensor 52, but when the second portion 606 is in the second position 650, the second portion 606 will obscure such a uniquely high signal and will present a unique signal (e.g., a uniquely intermediate signal) to the first sensor 52. The third sensor 52', on the other hand, can be positioned to be adjacent the signal-modulating feature 653' of the first portion 604 when the biological sterilization indicator 600 is fully seated in the well 14 of the reading apparatus 12', such that the unique modified signal from the signal-modulating feature 653' can be detected by the third sensor 52' when the second portion 606 is in the first position 648 or the second position 650.

In such embodiments, the first sensor 52 can generate (and the controller 51 can receive): a first signal (e.g., relatively low) when the well 14 is empty; a second signal, based on the smooth outer wall/surface of the exposed first portion 604, that is significantly different from the first signal, when the biological sterilization indicator 600 is positioned in the well 14 and the second portion 606 is not in the second position 650 (e.g., is in the first position 648); and a third signal, based on the signal-modulating feature 653 of the second portion 206, that is significantly different from the first signal and the second signal, when the biological sterilization indicator 600 is positioned in the well 14 and the second portion 606 is in the second position 650.

In addition, the third sensor 52' can generate (and the controller 51 can receive) a first signal (e.g., relatively low) when the well 14 is empty; and a second signal that is significantly different from the first signal, based on the signal-modulating feature 653' of the first portion 604. In addition, the third sensor 52' will indicate when the biological sterilization indicator 600 is incorrectly positioned in the well 14, because in some embodiments, the third sensor 52' can generate a third signal that is significantly different from the first signal and the second signal when the biological sterilization indicator 600 is turned around (i.e., positioned incorrectly) in the well 14. For example, if the biological sterilization indicator 600 were incorrectly oriented in the well 14, the third sensor 52' would no longer line up with the signal-modulating feature 653' of the first portion 604 to confirm that the biological sterilization indicator 600 is fully seated in the well 14, but rather the third sensor 52' would line up with a different portion of the biological sterilization indicator 600 (e.g., the smooth outer wall opposite the signal-modulating feature 653') and produce a relatively high signal, compared to the unique signal of the signal-modulating feature 653'. As a result, when the third sensor 52' sends the second signal and the first sensor 52 sends the third signal to a controller 51, the controller 51 can begin to initiate a spore growth and/or detection process, or the assay result will be output to the display 16 without an error code.

The first sensor 52 and the third sensor 52' can form a portion of a dedicated detection system 55' that is dedicated to the well 14 illustrated in FIG. 10, and which can further include the second sensor 54. As described above, the second sensor 54 can include the excitation source 72 and the detector 74, and can be used to confirm that the biological sterilization indicator 600 is fully seated in the well 14 (e.g., to reliably confirm activation of the biological sterilization indicator 600), and/or to perform the detection or assaying process by interrogating the biological sterilization indicator 600 for spore growth.

While the biological sterilization indicator systems 10 and 10', the biological sterilization indicators 100, 500, and 600, and the second portions 106, 206, 306, 406, 506, and 606 are described above as individual embodiments, it should be understood that a biological sterilization indicator system of the present disclosure can include any combination of the various features and elements described above and shown in FIGS. 1-10 that accomplishes the desired biological sterilization indicator system functions.

Furthermore, even though only one first sensor 52 is shown and described with respect to the reading apparatus 12 and the biological sterilization indicator system 10, and two first sensors 52, 52' are shown and described with respect to the reading apparatus 12' and the biological sterilization indicator system 10', it should be understood from the present disclosure that as many such first sensors 52 as necessary can be employed to detect a variety of signal-modulating features on various components of a biological sterilization indicator 100, 600 in order to confirm that the second portion 106, 606 of the biological sterilization indicator 100, 600 has moved a sufficient amount, and to confirm activation of the biological sterilization indicator 100, 600.

Embodiments

Embodiment 1 is a biological sterilization indicator system, the system comprising:
a biological sterilization indicator comprising:
a housing including
a first portion, and
a second portion adapted to be coupled to the first portion, the second portion being movable with respect to the first portion, when coupled to the first portion, between a first position and a second position; and
a container containing a liquid and being dimensioned to be positioned in the housing, at least a portion of the container being frangible, the container having a first state in which the container is intact when the second portion of the housing is in the first position, and a second state in which the container is fractured when the second portion of the housing is in the second position;
a first chamber within the housing in which the container is positioned when the container is in the first state; and
a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state; and
a reading apparatus comprising a well, the well dimensioned to receive at least a portion of the biological sterilization indicator, the reading apparatus configured to detect at least one of the following conditions:
when the biological sterilization indicator is positioned in the well with the second portion of the housing in the second position, and
when the biological sterilization indicator is positioned in the well with the liquid being present in the second chamber.

Embodiment 2 is a method for detecting an activation status of a biological sterilization indicator, the method comprising:
providing a biological sterilization indicator comprising:
a housing including
a first portion, and
a second portion adapted to be coupled to the first portion, the second portion being movable with respect to the first portion between an first position and a second position;
a container containing a liquid and dimensioned to be positioned in the housing, at least a portion of the container being frangible, the container having a first state in which the container is intact when the second portion of the housing is in the first position, and a second state in which the container is fractured when the second portion of the housing is in the second position;
a first chamber within the housing in which the container is positioned when the container is in the first state; and
a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state; and
providing a reading apparatus comprising a well dimensioned to receive at least a portion of the biological sterilization indicator; and
detecting at least one of the following conditions:
when the biological sterilization indicator is positioned in the well with the second portion of the housing in the second position, and
when the biological sterilization indicator is positioned in the well with the liquid being present in the second chamber.

Embodiment 3 is the system of embodiment 1 or the method of embodiment 2, wherein the biological sterilization indicator is confirmed as being activated when at least one of the conditions is detected.

Embodiment 4 is the system of embodiment 1 or 3, wherein the reading apparatus is further configured to detect when the well of the reading apparatus is empty.

Embodiment 5 is the system of any of embodiments 1, 3 and 4, wherein the reading apparatus is further configured to detect when the biological sterilization indicator is positioned in the well with the second portion of the housing in the first position.

Embodiment 6 is the system of any of embodiments 1 and 3-5, wherein the reading apparatus is further configured to detect when the biological sterilization indicator is positioned in the well with the liquid not being present in the second chamber.

Embodiment 7 is the system of any of embodiments 1 and 3-6, wherein the reading apparatus is further configured to detect at least one of the following conditions:
  when the well is empty,
  when the biological sterilization indicator is positioned in the well with the second portion of the housing in the first position, and
  when the liquid is not present in the second chamber.

Embodiment 8 is the system of any of embodiments 1 and 3-7, wherein the reading apparatus is configured to generate at least one of:
  a first signal when the biological sterilization indicator is positioned in the well with the second portion of the housing in the second position, and
  a second signal when the biological sterilization indicator is positioned in the well with the liquid being present in the second chamber.

Embodiment 9 is the system of any of embodiments 1 and 3-8, wherein the reading apparatus is configured to generate a signal indicative of at least one of the detected conditions.

Embodiment 10 is the system of embodiment 9, wherein the signal confirms activation of the biological sterilization indicator.

Embodiment 11 is the system of embodiment 9 or 10, wherein the signal is a second signal, and wherein the reading apparatus is further configured to generate a first signal indicative of the well being empty.

Embodiment 12 is the system of embodiment 9 or 10, wherein the signal is a second signal, and wherein the reading apparatus is further configured to generate a first signal indicative of the biological sterilization indicator being positioned in the well with the second portion of the housing in the first position.

Embodiment 13 is the system of embodiment 9 or 10, wherein the signal is a second signal, and wherein the reading apparatus is further configured to generate a first signal indicative of the liquid not being present in the second chamber.

Embodiment 14 is the system of embodiment 9 or 10, wherein the signal is a second signal, and wherein the reading apparatus is further configured to generate a first signal indicative of at least one of:
  the well being empty,
  the biological sterilization indicator being positioned in the well with the second portion of the housing in the first position, and
  the liquid not being present in the second chamber.

Embodiment 15 is the system of embodiment 9 or 10, wherein the signal is a third signal, and wherein the reading apparatus includes:
  a first sensor positioned adjacent a first region of the well, the first sensor configured to generate at least one of:
    a first signal indicative of the first region of the well being empty,
    a second signal indicative of the biological sterilization indicator being positioned in the first region of the well with the second portion of the housing in the first position, and
    the third signal being indicative of the biological sterilization indicator being positioned in the first region of the well with the second portion of the housing in the second position; and
  a second sensor positioned adjacent a second region of the well, the second sensor configured to generate at least one of:
    a fourth signal indicative of the second region of the well being empty,
    a fifth signal indicative of the biological sterilization indicator being positioned in the second region of the well and the liquid not being present in the second chamber, and
    a sixth signal indicative of the biological sterilization indicator being positioned in the second region of the well and the liquid being present in the second chamber.

Embodiment 16 is the system of embodiment 9 or 10, wherein the signal is a sixth signal, and wherein the reading apparatus includes:
  a first sensor positioned adjacent a first region of the well, the first sensor configured to generate at least one of:
    a first signal indicative of the first region of the well being empty,
    a second signal indicative of the biological sterilization indicator being positioned in the first region of the well with the second portion of the housing in the first position, and
    a third signal indicative of the biological sterilization indicator being positioned in the first region of the well with the second portion of the housing in the second position; and
  a second sensor positioned adjacent a second region of the well, the second sensor configured to generate at least one of:
    a fourth signal indicative of the second region of the well being empty,
    a fifth signal indicative of the biological sterilization indicator being positioned in the second region of the well and the liquid not being present in the second chamber, and
    the sixth signal being indicative of the biological sterilization indicator being positioned in the second region of the well and the liquid being present in the second chamber.

Embodiment 17 is the system of any of embodiments 1 and 3-16, wherein the reading apparatus further includes
  a first sensor positioned to detect the position of the second portion of the housing, and
  a second sensor positioned to detect whether the liquid is present in the second chamber.

Embodiment 18 is the system of embodiment 17, wherein the first sensor is positioned adjacent a first region of the well and the second sensor is positioned adjacent a second region of the well.

Embodiment 19 is the system of embodiment 17 or 18, wherein the reading apparatus is configured to generate a signal indicative of at least one of the detected conditions, wherein the signal is a third signal and is indicative of the biological sterilization indicator being positioned in the well with the second portion of the housing in the second position, and wherein the first sensor is configured to generate at least one of:
  a first signal when at least a portion of the well is empty,
  a second signal when the biological sterilization indicator is positioned in at least a portion of the well and the second portion of the housing is in the first position, and
  the third signal.

Embodiment 20 is the system of any of embodiments 17-19, wherein the first sensor is configured to detect at least one of:
  when at least a portion of the well is empty,
  when the biological sterilization indicator is positioned in at least a portion of the well and the second portion of the housing is in the first position, and
  when the biological sterilization indicator is positioned in at least a portion of the well and the second portion of the housing is in the second position.

Embodiment 21 is the system of any of embodiments 17-20, wherein the reading apparatus is configured to generate a signal indicative of at least one of the detected conditions, wherein the signal is a third signal and is indicative of the biological sterilization indicator being positioned in the well with the liquid being present in the second chamber, and wherein the second sensor is configured to generate at least one of:
  a first signal when a portion of the well adjacent the second sensor is empty,
  a second signal when biological sterilization indicator is positioned in the portion of the well adjacent the second sensor and the liquid is not present in the second chamber, and
  the third signal.

Embodiment 22 is the system of any of embodiments 17-21, wherein the second sensor is further configured to detect at least one of:
  when at least a portion of the well is empty,
  when the biological sterilization indicator is positioned in the well and the liquid is not present in the second chamber, and
  when the biological sterilization indicator is positioned in the well and the liquid is present in the second chamber.

Embodiment 23 is the system of any of embodiments 15-22, wherein the first sensor includes a photointerrupter.

Embodiment 24 is the system of any of embodiments 15-23, wherein the second sensor includes a fluorescence detection system including an excitation light source and a detector.

Embodiment 25 is the method of embodiment 2 or 3, further comprising positioning the biological sterilization indicator in the well of the reading apparatus.

Embodiment 26 is the method of any of embodiments 2, 3 and 25, further comprising generating a signal indicative of at least one of the detected conditions.

Embodiment 27 is the method of embodiment 26, wherein generating a signal includes generating a second signal, and further comprising generating a first signal indicative of at least one of:
  the well being empty,
  the biological sterilization indicator being positioned in the well with the second portion of the housing in the first position, and
  the liquid not being present in the second chamber.

Embodiment 28 is the system of any of embodiments 1 and 3-24 or the method of any of embodiments 2, 3 and 25-27, wherein the presence of the liquid in the second chamber is detected by at least one of a change in refractive index and a change in optical density.

Embodiment 29 is a biological sterilization indicator system, the system comprising:
  a biological sterilization indicator comprising:
    a housing;
    a container containing a liquid and being dimensioned to be positioned in the housing, at least a portion of the container being frangible, the container having a first state in which the container is intact and the liquid is not in fluid communication with an interior of the housing and a second state in which the container is fractured and the liquid is in fluid communication with the interior of the housing;
    a first chamber within the housing in which the container is positioned when the container is in the first state; and
    a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state; and
  a reading apparatus comprising a well, the well dimensioned to receive at least a portion of the biological sterilization indicator, the reading apparatus configured to detect when the biological sterilization indicator is positioned in the well and the liquid is present in the second chamber.

Embodiment 30 is the system of embodiment 29, wherein the reading apparatus is further configured to detect when the well of the reading apparatus is empty.

Embodiment 31 is the system of embodiment 29, wherein the reading apparatus is further configured to detect at least one of the following conditions:
  when the well is empty, and
  when the liquid is not present in the second chamber.

Embodiment 32 is the system of any of embodiments 29-31, wherein the reading apparatus is further configured to generate a signal indicative of when the biological sterilization indicator is positioned in the well and the liquid is present in the second chamber.

Embodiment 33 is the system of embodiment 32, wherein the signal is a second signal, and wherein the reading apparatus is further configured to generate a first signal indicative of at least one of:
  the well being empty, and
  the liquid not being present in the second chamber.

Embodiment 34 is the system of embodiment 32, wherein the signal is a third signal, and wherein the reading apparatus is further configured to generate at least one of:
  a first signal indicative of at least a portion of the well being empty,
  a second signal indicative of the biological sterilization indicator being positioned in at least a portion of the well and the liquid not being present in the second chamber, and
  the third signal.

Embodiment 35 is the system of any of embodiments 29-34, wherein the reading apparatus includes a sensor positioned to detect whether the liquid is present in the second chamber.

Embodiment 36 is the system of embodiment 35, wherein the sensor is configured to generate a signal indicative of at least one of:
- when at least a portion of the well is empty,
- when the biological sterilization indicator is positioned in the well and the liquid is not present in the second chamber, and
- when the biological sterilization indicator is positioned in the well and the liquid is present in the second chamber.

Embodiment 37 is the system of any of embodiments 29-36, wherein the reading apparatus includes a sensor positioned adjacent the well, the sensor configured to generate at least one of:
- a first signal indicative of at least a portion of the well being empty,
- a second signal indicative of the biological sterilization indicator being positioned in at least a portion of the well and the liquid not being present in the second chamber, and
- a third signal indicative of the biological sterilization indicator being positioned in at least a portion of the well and the liquid being present in the second chamber.

Embodiment 38 is the system of embodiment 37, wherein the sensor is positioned adjacent the second chamber of the biological sterilization indicator.

Embodiment 39 is the system of any of embodiments 35-38, wherein the sensor is further configured to detect whether the at least one source of biological activity survived a sterilization process.

Embodiment 40 is the system of any of embodiments 35-39, wherein the sensor includes a photointerrupter.

Embodiment 41 is the system of any of embodiments 35-40, wherein the sensor includes a fluorescence detection system including an excitation light source and a detector.

Embodiment 42 is a method for detecting an activation status of a biological sterilization indicator, the method comprising:
- providing a biological sterilization indicator comprising:
  - a housing;
  - a container containing a liquid and being dimensioned to be positioned in the housing, at least a portion of the container being frangible, the container having a first state in which the container is intact and the liquid is not in fluid communication with an interior of the housing and a second state in which the container is fractured and the liquid is in fluid communication with the interior of the housing;
  - a first chamber within the housing in which the container is positioned when the container is in the first state;
  - a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state;
- providing a reading apparatus comprising a well dimensioned to receive at least a portion of the biological sterilization indicator; and
- detecting when the biological sterilization indicator is positioned in the well and the liquid is present in the second chamber.

Embodiment 43 is the method of embodiment 42, further comprising positioning the biological sterilization indicator in the well of the reading apparatus.

Embodiment 44 is the method of embodiment 42 or 43, further comprising detecting when the well of the reading apparatus is empty.

Embodiment 45 is the method of any of embodiments 42-44, further comprising detecting at least one of the following conditions:
- when the well is empty, and
- when the liquid is not present in the second chamber.

Embodiment 46 is the method of any of embodiments 42-45, further comprising generating a signal when the biological sterilization indicator is detected as being positioned in the well and the liquid is present in the second chamber.

Embodiment 47 is the method of embodiment 46, wherein generating a signal includes generating a second signal, and further comprising generating a first signal indicative of at least one of:
- the well being empty, and
- the liquid not being present in the second chamber.

Embodiment 48 is the system or method of any of embodiments 29-47, wherein the presence of the liquid in the second chamber is detected by detecting at least one of refractive index and optical density.

Embodiment 49 is the system or method of any of embodiments 29-48, wherein the housing of the biological sterilization indicator includes:
- a first portion, and
- a second portion adapted to be coupled to the first portion, the second portion being movable with respect to the first portion, when coupled to the first portion, between a first position and a second position.

Embodiment 50 is the system of any of embodiments 1, 3-24, 28 and 49 or the method of any of embodiments 2, 3, 25-28 and 49, wherein the first portion of the housing includes an open end and a closed end, and wherein the second portion of the housing is adapted to be coupled to the open end of the first portion of the housing.

Embodiment 51 is the system or method of embodiment 50, wherein the second position is located closer to the closed end of the first portion of the housing than the first position.

Embodiment 52 is the system of any of embodiments 1, 3-24, 28 and 49-51 or the method of any of embodiments 2, 3, 25-28 and 49-51, wherein the biological sterilization indicator is open to ambience when the second portion of the housing is in the first position, and wherein the biological sterilization indicator is sealed from ambience when the second portion of the housing is in the second position.

Embodiment 53 is the system of any of embodiments 1, 3-24, 28 and 49-52 or the method of any of embodiments 2, 3, 25-28 and 49-52, wherein the housing includes a longitudinal direction, and wherein the second portion of the housing is movable in the longitudinal direction with respect to the first portion between the first position and the second position.

Embodiment 54 is the system of any of embodiments 1, 3-24, 28 and 49-53 or the method of any of embodiments 2, 3, 25-28 and 49-53, wherein the container is in the first state when the second portion of the housing is in the first position, and wherein the container is in the second state when the second portion of the housing is in the second position.

Embodiment 55 is the system of any of embodiments 1, 3-24, 28 and 49-54 or the method of any of embodiments 2, 3, 25-28 and 49-54, wherein the second portion of the housing is movable with respect to the first portion of the housing when the biological sterilization indicator is positioned in the well of the reading apparatus, and when the biological sterilization indicator is located outside of the well of the reading apparatus.

Embodiment 56 is the system of any of embodiments 1, 3-24, 28 and 49-55 or the method of any of embodiments 2, 3, 25-28 and 49-55, wherein the housing includes a longitudinal direction, and wherein the container is movable in the longitudinal direction of the housing in response to movement of the second portion of the housing between the first position and the second position.

Embodiment 57 is the system of any of embodiments 1, 3-24, 28 and 49-56 or the method of any of embodiments 2, 3, 25-28 and 49-56, wherein the second portion of the housing is in the first position during sterilization, and wherein the second portion of the housing is in the second position after activation.

Embodiment 58 is the system of any of embodiments 1, 3-24, 28 and 49-57 or the method of any of embodiments 2, 3, 25-28 and 49-57, wherein the first portion of the housing includes at least one substantially planar outer wall positioned adjacent the second chamber of the housing.

Embodiment 59 is the system or method of embodiment 58, wherein the at least one substantially planar wall includes two substantially parallel walls.

Embodiment 60 is the system or method of embodiment 59, wherein the at least one substantially planar wall includes a detection window.

Embodiment 61 is the method of any of embodiments 2, 3, 25-28 and 49-60, further comprising moving the second portion of the housing from the first position to the second position.

Embodiment 62 is the method of embodiment 61, wherein the housing includes a longitudinal direction, and wherein moving the second portion of the housing includes moving the second portion of the housing in the longitudinal direction.

Embodiment 63 is the method of embodiment 61 or 62, wherein moving the second portion of the housing from the first position to the second position occurs before positioning the biological sterilization indicator in the well, such that when the biological sterilization indicator is positioned in the well, the liquid is detected as being present in the second chamber of the biological sterilization indicator.

Embodiment 64 is the method of any of embodiments 61-63, wherein moving the second portion of the housing from the first position to the second position occurs after positioning the biological sterilization indicator in the well, such that when the biological sterilization indicator is positioned in the well, the liquid is not detected as being present in the second chamber of the biological sterilization indicator, and when the second portion of the housing is moved to the second position, the liquid is detected as being present in the second chamber of the biological sterilization indicator.

Embodiment 65 is the method of any of embodiments 61-64, further comprising moving the container in the housing in response to moving the second portion of the housing from the first position to the second position.

Embodiment 66 is the method of any of embodiments 61-65, wherein moving the container in the housing causes the container to fracture.

Embodiment 67 is the method of any of embodiments 61-66, wherein moving the second portion of the housing from the first position to the second position causes the container to fracture.

Embodiment 68 is the method of any of embodiments 2, 3, 25-28 and 42-67, further comprising fracturing the container to move the liquid into the second chamber.

Embodiment 69 is the method of embodiment 68, further comprising detecting that the liquid is present in the second chamber of the biological sterilization indicator in response to moving the liquid into the second chamber.

Embodiment 70 is the system of any of embodiments 1, 3-24, 28-41 and 48-60 or the method of any of embodiments 2, 3, 25-28 and 42-69, wherein the reading apparatus is further configured to incubate the biological sterilization indicator.

Embodiment 71 is the system of any of embodiments 1, 3-24, 28-41, 48-60 and 70 or the method of any of embodiments 2, 3, 25-28 and 42-70, wherein the biological sterilization indicator is keyed with respect to the well, such that the biological sterilization indicator is positioned fully within the well in only one orientation.

Embodiment 72 is the system of any of embodiments 1, 3-24, 28-41, 48-60 and 70-71 or the method of any of embodiments 2, 3, 25-28 and 42-71, wherein the container is in the first state during sterilization, and wherein the container is in the second state after activation.

Embodiment 73 is the system of any of embodiments 1, 3-24, 28-41, 48-60 and 70-72 or the method of any of embodiments 2, 3, 25-28 and 42-72, wherein the first chamber and the second chamber are separated in the housing by a partial wall that is oriented with respect to a longitudinal direction of the housing at a non-zero and non-right angle.

Embodiment 74 is the system of any of embodiments 1, 3-24, 28-41, 48-60 and 70-73 or the method of any of embodiments 2, 3, 25-28 and 42-73, wherein the second chamber has a smaller volume than the first chamber.

Embodiment 75 is the system of any of embodiments 1, 3-24, 28-41, 48-60 and 70-74 or the method of any of embodiments 2, 3, 25-28 and 42-74, wherein the second chamber has a smaller cross-sectional area than the first chamber.

Embodiment 76 is the system of any of embodiments 1, 3-24, 28-41, 48-60 and 70-75 or the method of any of embodiments 2, 3, 25-28 and 42-75, wherein the second chamber is formed by the first portion of the housing.

Embodiment 77 is the system of any of embodiments 1, 3-24, 28-41, 48-60 and 70-76 or the method of any of embodiments 2, 3, 25-28 and 42-76, wherein the first chamber is formed at least partially by the first portion of the housing.

Embodiment 78 is the system of any of embodiments 1, 3-24, 28-41, 48-60 and 70-77 or the method of any of embodiments 2, 3, 25-28 and 42-77, wherein the reading apparatus includes a sensor configured to detect an optical signal in the biological sterilization indicator.

Embodiment 79 is a biological sterilization indicator system, the system comprising:
  a biological sterilization indicator comprising:
    a housing including
      a first portion, and
      a second portion adapted to be coupled to the first portion, the second portion being movable with respect to the first portion, when coupled to the first portion, between a first position and a second position; and
    a container containing a liquid and being dimensioned to be positioned in the housing, at least a portion of the container being frangible, the container having a first state in which the container is intact when the second portion of the housing is in the first position, and a second state in which the container is fractured when the second portion of the housing is in the second position;

a first chamber within the housing in which the container is positioned when the container is in the first state; and a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state; and a reading apparatus comprising a well, the well dimensioned to receive at least a portion of the biological sterilization indicator, the reading apparatus configured to generate a signal indicative of at least one of:

the biological sterilization indicator being positioned in the well with the second portion of the housing in the second position, and the biological sterilization indicator being positioned in the well with the liquid being present in the second chamber.

Embodiment 80 is a method for detecting an activation status of a biological sterilization indicator, the method comprising:

providing a biological sterilization indicator comprising:
a housing including
a first portion, and
a second portion adapted to be coupled to the first portion, the second portion being movable with respect to the first portion between a first position and a second position;

a container containing a liquid and dimensioned to be positioned in the housing, at least a portion of the container being frangible, the container having a first state in which the container is intact when the second portion of the housing is in the first position, and a second state in which the container is fractured when the second portion of the housing is in the second position;

a first chamber within the housing in which the container is positioned when the container is in the first state; and a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state; and providing a reading apparatus comprising a well dimensioned to receive at least a portion of the biological sterilization indicator;

positioning the biological sterilization indicator in the well of the reading apparatus; and generating a signal indicative of at least one of:
the biological sterilization indicator being positioned in the well with the second portion of the housing in the second position, and
the biological sterilization indicator being positioned in the well with the liquid being present in the second chamber.

Embodiment 81 is a biological sterilization indicator system, the system comprising:

a biological sterilization indicator comprising:
a housing;
a container containing a liquid and being dimensioned to be positioned in the housing, at least a portion of the container being frangible, the container having a first state in which the container is intact and the liquid is not in fluid communication with an interior of the housing and a second state in which the container is fractured and the liquid is in fluid communication with the interior of the housing;
a first chamber within the housing in which the container is positioned when the container is in the first state; and
a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state; and a reading apparatus comprising a well, the well dimensioned to receive at least a portion of the biological sterilization indicator, the reading apparatus configured to generate at least one of:
a first signal when the biological sterilization indicator is positioned in the well and the liquid is not present in the second chamber, and
a second signal when the biological sterilization indicator is positioned in the well and the liquid is present in the second chamber.

Embodiment 82 is a method for detecting an activation status of a biological sterilization indicator, the method comprising:

providing a biological sterilization indicator comprising:
a housing;
a container containing a liquid and being dimensioned to be positioned in the housing, at least a portion of the container being frangible, the container having a first state in which the container is intact and the liquid is not in fluid communication with an interior of the housing and a second state in which the container is fractured and the liquid is in fluid communication with the interior of the housing;
a first chamber within the housing in which the container is positioned when the container is in the first state;
a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state;

providing a reading apparatus comprising a well dimensioned to receive at least a portion of the biological sterilization indicator;

positioning the biological sterilization indicator in the well of the reading apparatus; and generating at least one of the following signals:
- a first signal when the biological sterilization indicator is positioned in the well and the liquid is not present in the second chamber, and
- a second signal when the biological sterilization indicator is positioned in the well and the liquid is present in the second chamber.

Embodiment 83 is the system or method of any of the above embodiments, wherein at least a portion of the housing of the biological sterilization indicator includes a surface modification.

Embodiment 84 is a biological sterilization indicator comprising:
- a housing;
- a container containing a liquid and being dimensioned to be positioned in the housing, at least a portion of the container being frangible, the container having a first state in which the container is intact and the liquid is not in fluid communication with an interior of the housing and a second state in which the container is fractured and the liquid is in fluid communication with the interior of the housing;
- a first chamber in the housing in which the container is positioned when the container is in the first state; and
- a second chamber in the housing in which the container and the liquid are not positioned when the container is in the first state, the second chamber comprising a source of biological activity that is not in fluid communication with the liquid when the container is in the first state and that is in fluid communication with the liquid when the container is in the second state; and
- wherein at least a portion of the housing includes a surface modification positioned to inhibit ambient light from reaching the second chamber of the biological sterilization indicator.

Embodiment 85 is the biological sterilization indicator of embodiment 84, wherein the surface modification includes a textured surface.

Embodiment 86 is the biological sterilization indicator of embodiment 84 or 85, wherein the housing of the biological sterilization indicator includes:
- a first portion, and
- a second portion adapted to be coupled to the first portion, the second portion being movable with respect to the first portion, when coupled to the first portion, between a first position and a second position; and
- wherein the first portion of the housing includes the surface modification.

Embodiment 87 is the biological sterilization indicator of embodiment 86, wherein the surface modification is located on an upper portion of the first portion of the housing.

Embodiment 88 is the biological sterilization indicator of any of embodiments 84-87, wherein the surface modification is configured to scatter ambient light.

Embodiment 89 is the biological sterilization indicator of any of embodiments 84-88, wherein the surface modification is positioned to inhibit ambient light from reaching the second chamber of the biological sterilization indicator when the biological sterilization indicator is positioned in a well of a reading apparatus.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A method for detecting an activation status of a biological sterilization indicator, the method comprising:
    providing a biological sterilization indicator comprising:
        a housing including
            a first portion, and
            a second portion adapted to be coupled to the first portion, the second portion being movable with respect to the first portion between an first position and a second position;
        a container containing a liquid and dimensioned to be positioned in the housing, at least a portion of the container being frangible, the container having a first state in which the container is intact when the second portion of the housing is in the first position, and a second state in which the container is fractured when the second portion of the housing is in the second position;
        a first chamber within the housing in which the container is positioned when the container is in the first state; and
        a second chamber within the housing in which the container and the liquid are not positioned when the container is in the first state, and into which the liquid moves when the container is in the second state, the second chamber comprising at least one source of biological activity that is not in fluid communication with the liquid when the container is in the first state and that is in fluid communication with the liquid when the container is in the second state; and
    providing a reading apparatus comprising a well dimensioned to receive at least a portion of the biological sterilization indicator; and
    detecting an activation status of the biological sterilization indicator, with the reading apparatus, separately from detection of sterilization efficacy, by detecting whether the liquid is present in the second chamber when at least a portion of the biological sterilization indicator is positioned in the well.

2. The method of claim 1, wherein detecting whether the liquid is present in the second chamber includes detecting at least one of a change in refractive index and a change in optical density.

3. The method of claim 1, wherein the reading apparatus includes:
    a sensor positioned adjacent the well, and
    wherein detecting an activation status of the biological sterilization indicator includes detecting, with the sensor, at least one of a presence and an absence of the liquid in the second chamber when the biological sterilization indicator is positioned in the well.

4. The method of claim 1, wherein detecting an activation status of the biological sterilization indicator, with the reading apparatus, further includes detecting a position of the second portion of the housing when the biological sterilization indicator is positioned in the well.

5. The method of claim 1, wherein the reading apparatus includes:
    a sensor positioned adjacent the well; and
    wherein detecting an activation status of the biological sterilization indicator further includes detecting, with the sensor, a position of the second portion of the housing when the biological sterilization indicator is positioned in the well.

6. The method of claim 1, wherein the housing includes at least one substantially planar outer wall positioned adjacent the second chamber of the housing.

7. The method of claim 1, wherein the biological sterilization indicator is keyed with respect to the well, such that the biological sterilization indicator is positioned fully within the well in only one orientation.

8. The method of claim 1, wherein the reading apparatus includes a sensor positioned adjacent the well, and wherein detecting an activation status of the biological sterilization indicator includes detection by the sensor.

9. The method of claim 8, wherein detecting whether the liquid is present in the second chamber when at least a portion of the biological sterilization indicator is positioned in the well includes detecting, with the sensor, at least one of:

when the liquid is not present in the second chamber when at least a portion of the biological sterilization indicator is positioned in the well; and when the liquid is present in the second chamber when at least a portion of the biological sterilization indicator is positioned in the well.

10. The method of claim 8, further comprising detecting sterilization efficacy, wherein detecting sterilization efficacy includes detection by the sensor.

11. The method of claim 1, further comprising using the activation status to confirm or deny a sterilization efficacy result.

12. The method of claim 1, further comprising generating a signal, with the reading apparatus, indicative of the activation status.

13. The method of claim 1, further comprising at least one of:
(i) using the reading apparatus to determine a sterilization efficacy result if the liquid is detected in the second chamber, and
(ii) using the reading apparatus to determine a sterilization efficacy result and output an error code if the liquid is not detected in the second chamber.

14. The method of claim 1, further comprising using the reading apparatus to output an error code if the liquid is not detected in the second chamber.

* * * * *